United States Patent [19]

Seale

[11] Patent Number: 4,771,792

[45] Date of Patent: * Sep. 20, 1988

[54] NON-INVASIVE DETERMINATION OF MECHANICAL CHARACTERISTICS IN THE BODY

[76] Inventor: Joseph B. Seale, 44 Puritan Rd., Buzzards Bay, Mass. 02532

[*] Notice: The portion of the term of this patent subsequent to Mar. 3, 2004 has been disclaimed.

[21] Appl. No.: 930,366

[22] PCT Filed: Feb. 19, 1986

[86] PCT No.: PCT/US86/00351

§ 371 Date: Oct. 16, 1986

§ 102(e) Date: Oct. 16, 1986

[87] PCT Pub. No.: WO86/04801

PCT Pub. Date: Aug. 28, 1986

Related U.S. Application Data

[63] Continuation-in-part of Ser. No. 702,833, Feb. 19, 1985, Pat. No. 4,646,754.

[51] Int. Cl.4 .................................................. A61B 5/10
[52] U.S. Cl. ..................................... 128/774; 128/649; 128/677; 73/575; 364/508
[58] Field of Search ............... 128/630, 649, 672, 677, 128/739, 744, 774; 73/570, 573, 575, 579, 584, 648, 659, 668, 702

[56] References Cited

U.S. PATENT DOCUMENTS

| | | | |
|---|---|---|---|
| 3,836,757 | 9/1974 | Nachtigal et al. | 73/575 X |
| 3,842,663 | 10/1974 | Harting et al. | 73/659 X |
| 3,882,718 | 5/1975 | Kriebel | 128/648 |
| 4,418,573 | 12/1983 | Madigosky et al. | 73/584 X |
| 4,646,754 | 3/1987 | Scale | 128/774 |

Primary Examiner—Francis J. Jaworski

[57] ABSTRACT

A non-invasive system and method for inducing vibrations in a selected element of the human body and detecting the nature of responses for determining mechanical characteristics of the element are provided. The method comprises the steps of: inducing multiple-frequency vibrations, including below 20 KHz, in a selected element of the body by use of a driver; determining parameters of the vibration exerted on the body by the driver; sensing variations of a dimension of the element of the body over time, including in response to the driver; correlating the variations with frequency components of operation of the driver below 20 KHz to determine corresponding frequency components of the variations; resolving the frequency components into components of vibration mode shape; and determining the mechanical characteristics of the element on the basis of the parameters of vibration exerted by the driver and of the components of vibration mode shape.

7 Claims, 13 Drawing Sheets

MAJOR SYSTEM COMPONENTS

ULTRASOUND TRANSDUCERS

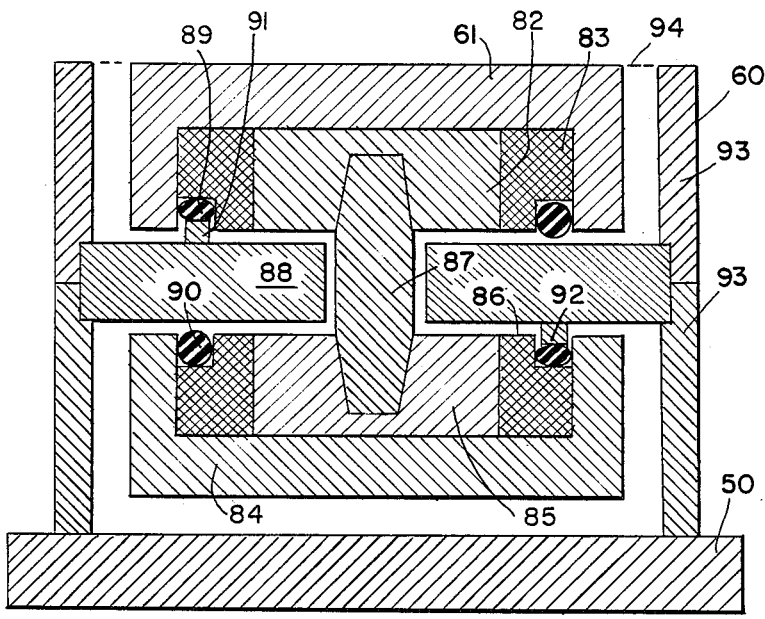
FIG. 4 VIBRATION DRIVER
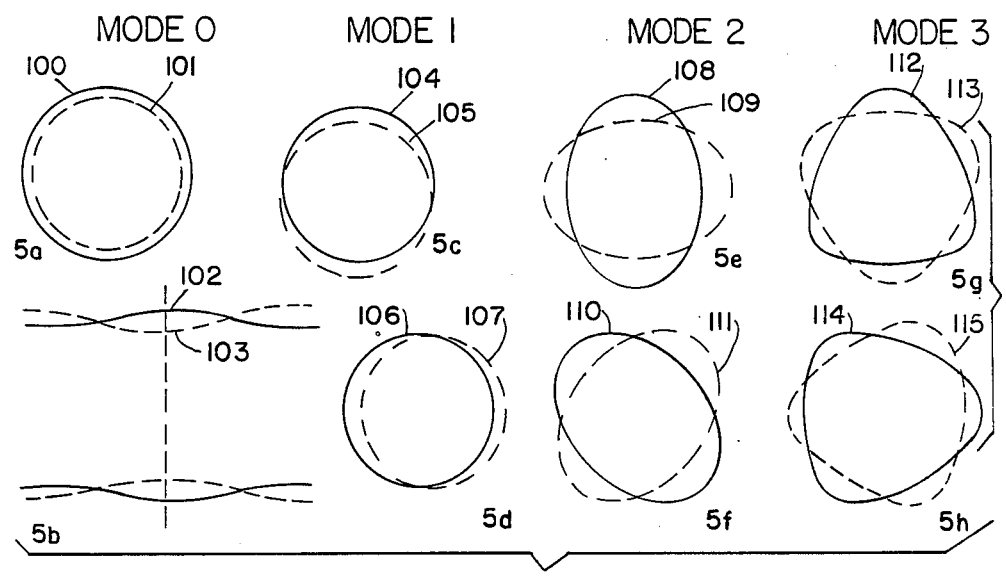
FIG. 5 ARTERIAL VIBRATION MODES

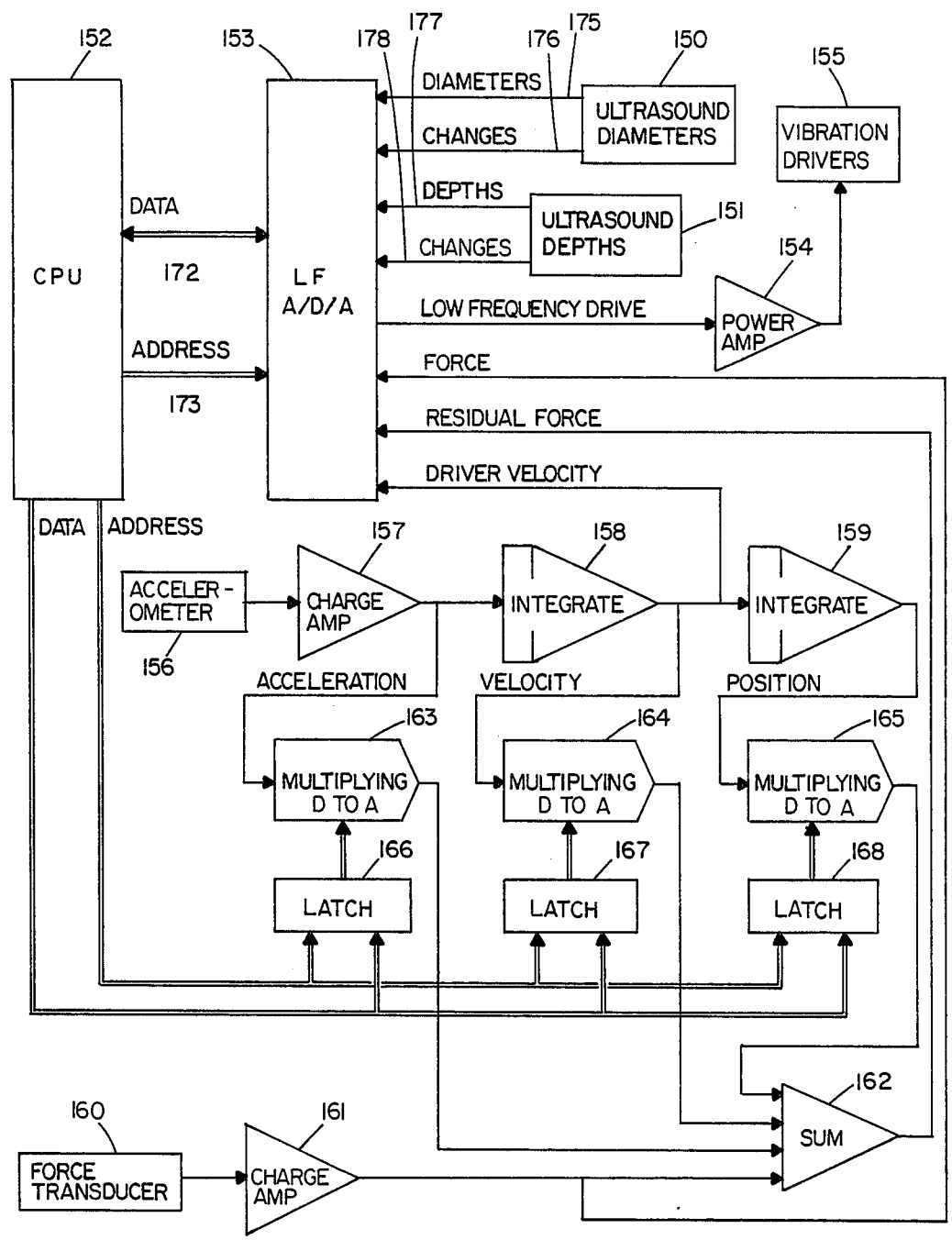
FIG. 6 LOW FREQUENCY A/D/A AND CONTROL

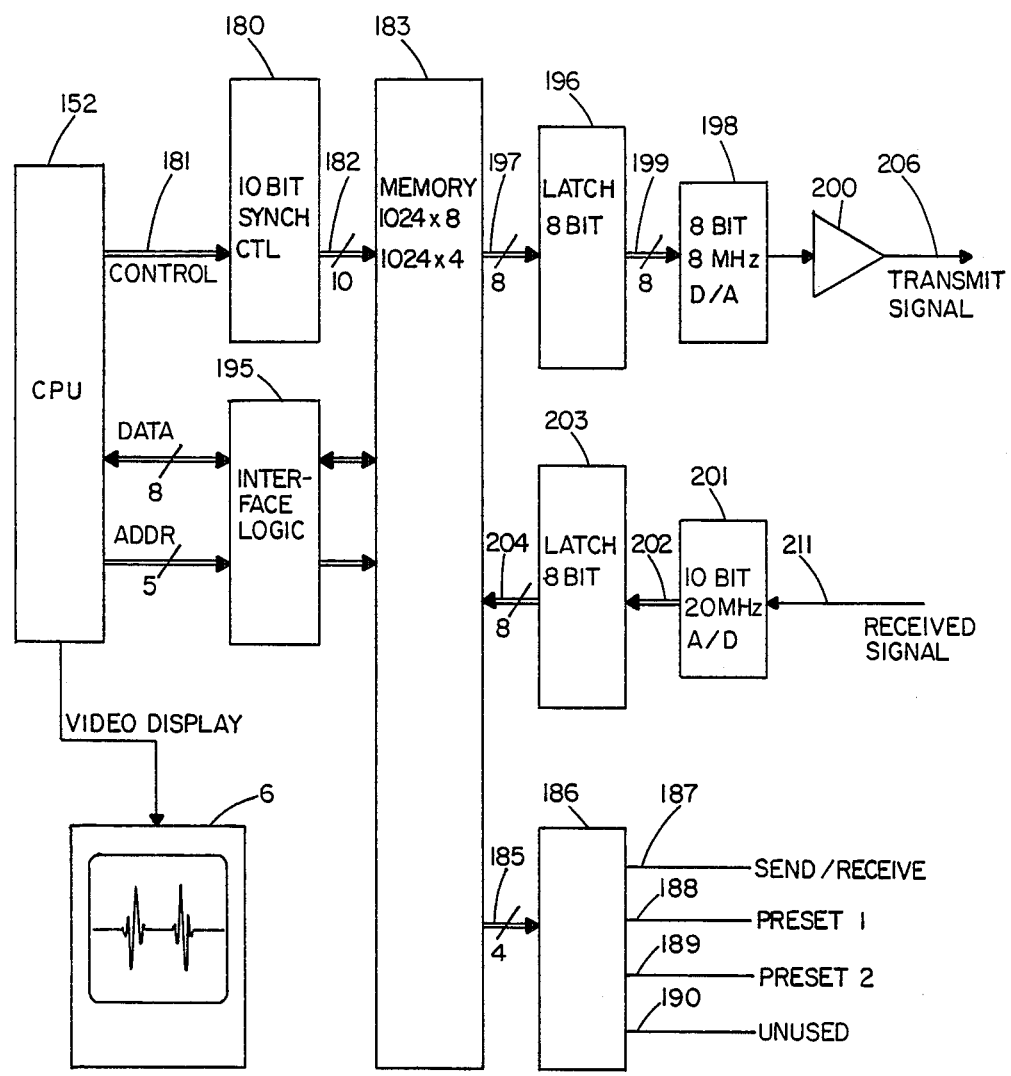
FIG. 7 ULTRASOUND A/D/A AND CONTROL

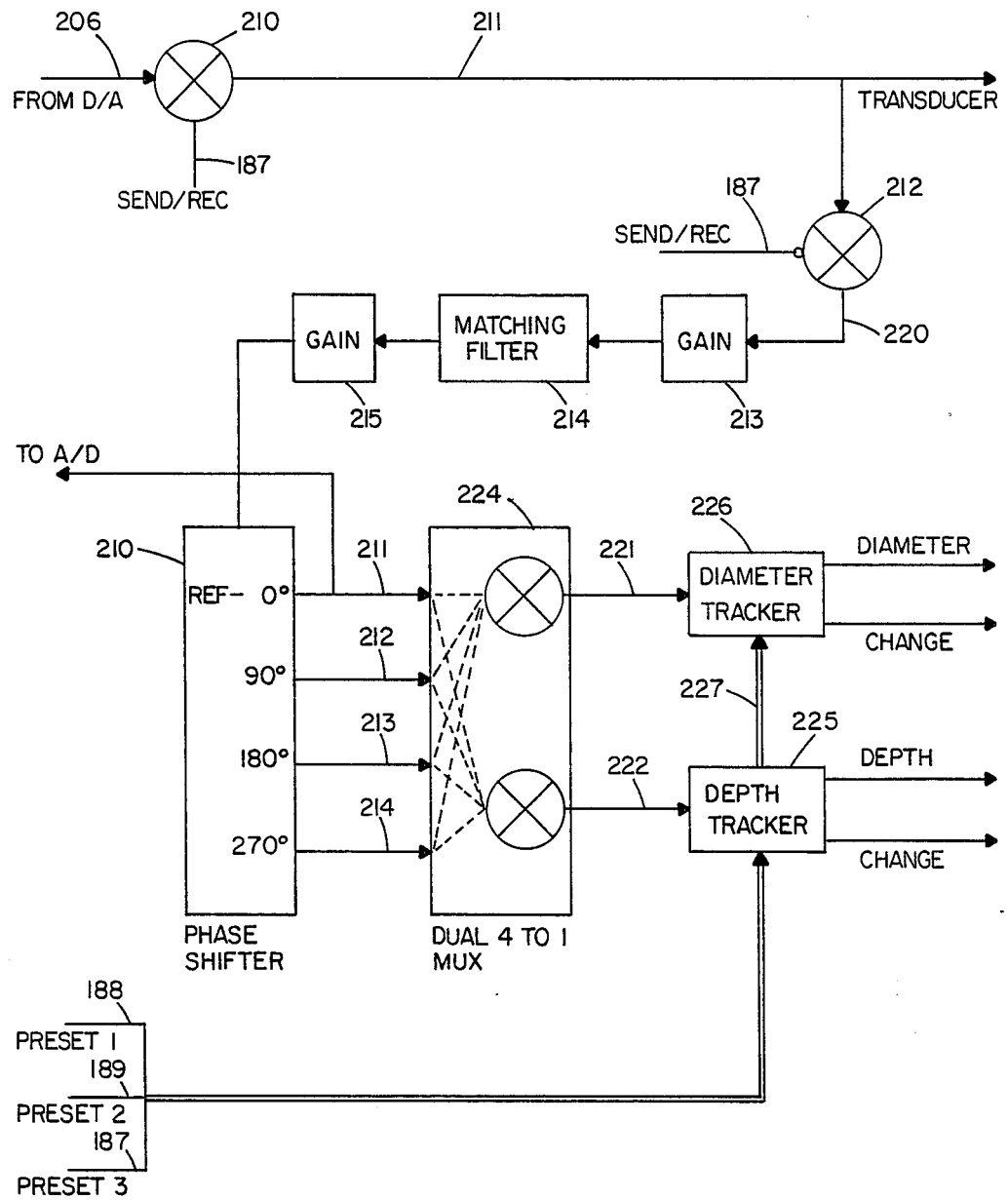
FIG. 8 ULTRASOUND TRACKING

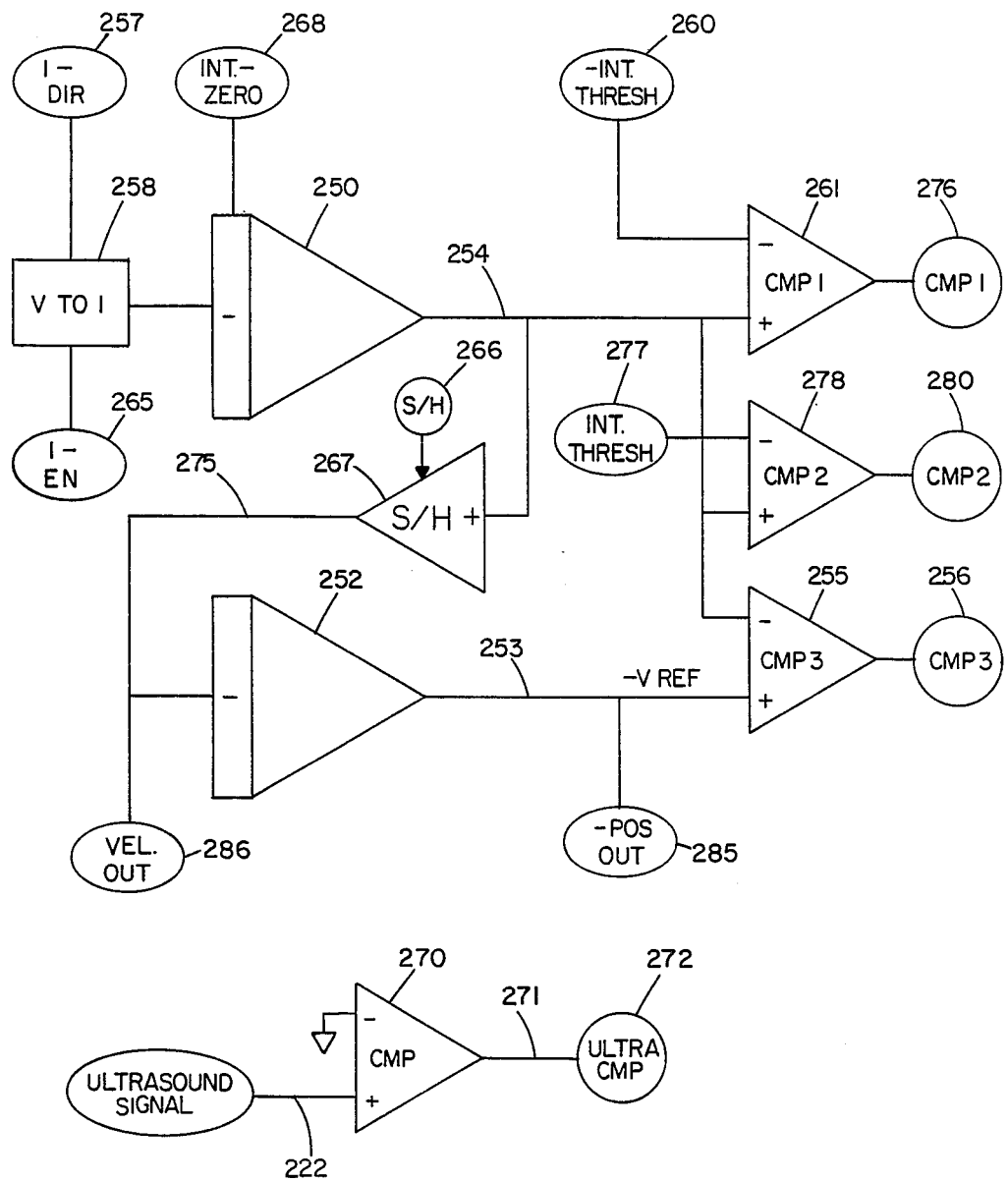
FIG. 9 ULTRASOUND TRACKER

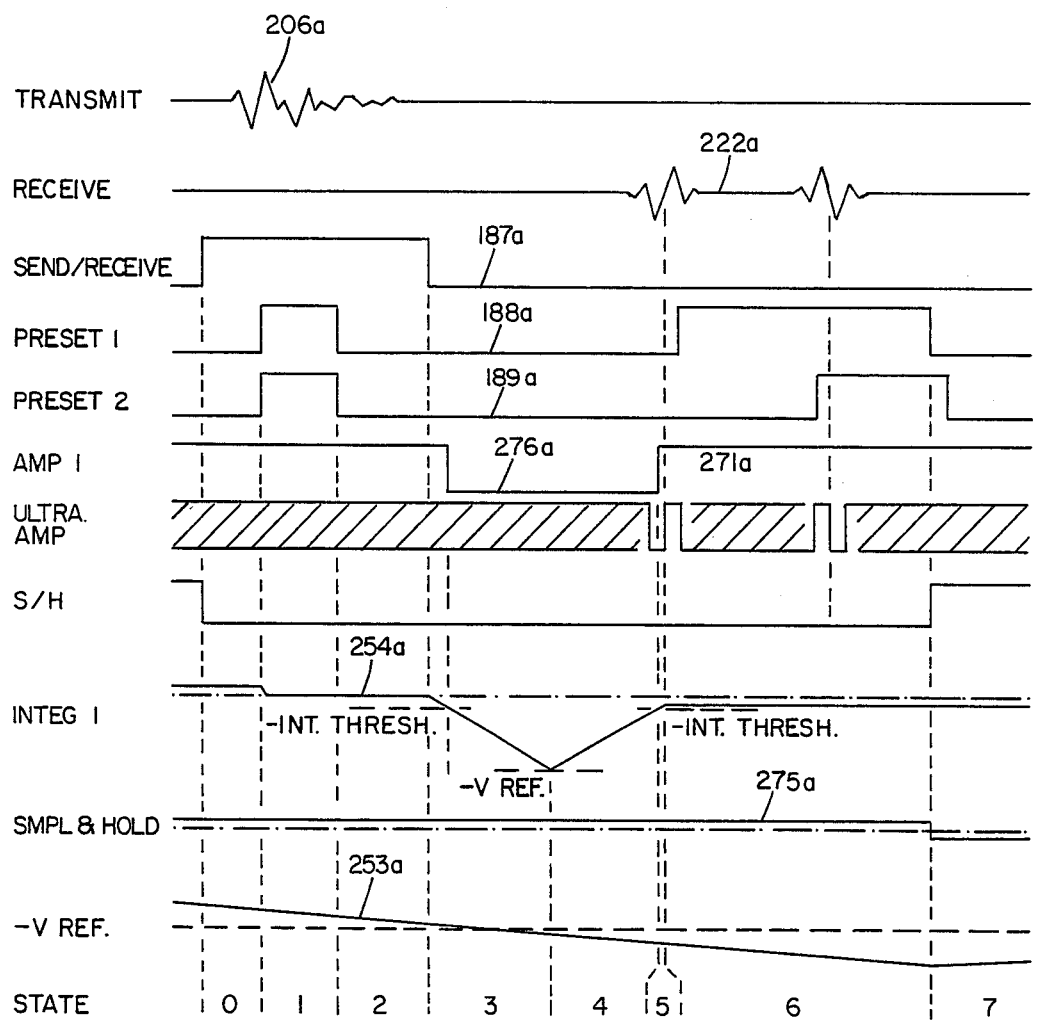
FIG. 10 TIMING DIAGRAM

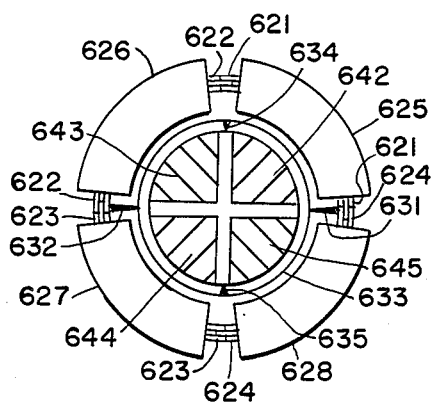
FIG. 12a
FIG. 12b
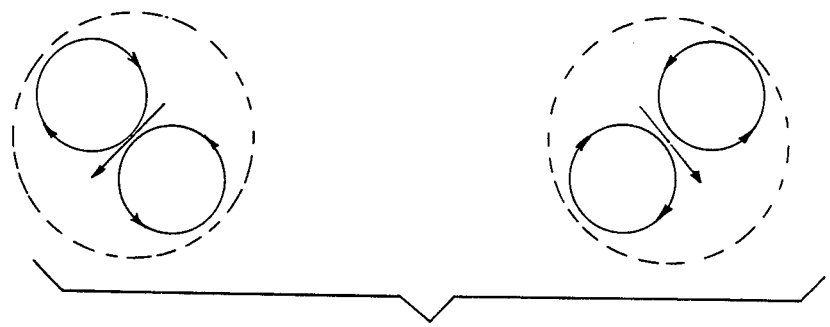
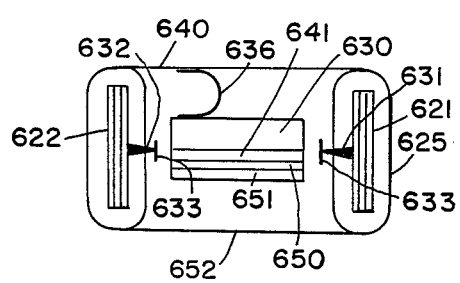
FIG. 12c

NON-INVASIVE DETERMINATION OF MECHANICAL CHARACTERISTICS IN THE BODY

This is a continuation-in-part of application Ser. No. 702,833, filed Feb. 19, 1985, now U.S. Pat. No. 4,646,754.

BACKGROUND OF THE INVENTION

This invention relates to non-invasive, small-perturbation measurements of macroscopic mechanical properties of organs and blood vessels to evaluate tissue pathology and body function.

Pathological tissue changes are often correlated with changes in density, elasticity and damping. While microscopic mechanical changes are sometimes correlated with ultrasound transmission and reflection properties, many important mechanical changes are manifested most clearly on a large scale at low frequencies. For these, manual palpation remains almost the sole diagnostic tool. Considerable effort has gone into blood pressure measurement methods, but not by analyzing small-perturbation mechanical properties of the pressurized vessel. Intraocular pressure is sensed by causing small eyeball shape perturbations, either by flattening a predetermined area of the sclera against an instrument surface, or by distorting the eyeball with a calibrated puff of air and measuring the deflection of a light beam reflected off the eye. The current invention similarly induces small shape perturbations, but obtains better data with greater patient comfort through a sophisticated use of vibrational excitation and mechanical response measurement and analysis.

Blood pressure measurement methods are commonly invasive or cause temporary occlusion of blood flow. A common measurement involves a catheter inserted into the radial artery and advanced to the aorta. Pulmonary arterial and capillary pressures are measured by the Swan Ganz method, whereby a catheter is advanced via a large vein and through heart valves into the right atrium, through the right ventricle, into the pulmonary trunk and up to the T-branching of right and left pulmonary arteries. Pulmonary arterial pressure is measured through the catheter, while pulmonary capillary pressure is obtained by inflating a balloon at the catheter tip to occlude flow to one lung while measuring the fall in pressure distal to the balloon, approaching capillary pressure. The trauma and risk of these invasive methods is apparent.

Non-invasive occlusive blood pressure methods commonly employ a pressurized cuff surrounding an arm or leg to collapse an underlying artery. The moments of collapse and reinflation, marking the times when blood pressure drops below and rises above cuff pressure, are sensed from blood flow noise (by stethoscope or contact microphone), by ultrasound doppler flow detection or from a sudden change in limb cross-section (sensed by monitoring of pressure or volume in the occluding cuff or a sensing cuff placed distal to the occluding cuff). The result is usually an estimate of systolic and diastolic extremes of pressure. Where cuff pressure pulsations are sensed as average cuff pressure is varied, mean arterial pressure can be estimated. These cuff methods depend on a steady heartbeat and cannot follow irregular beat-to-beat pressure fluctuations.

Recent servo cuff methods overcoming some of the above difficulties include those described by Aaslid and Brubakk, *Circulation*, Vol. 4, No. 4 (ultrasound doppler monitors brachial artery flow while a servoed cuff maintains fixed, reduced flow) and Yamakoshi et al, "Indirect Measurement of Instantaneous Arterial Blood Pressure in the Human Finger by the Vascular Unloading Technique", *IEEE Trans. on Biomedical Eng.*, Vol. BME-27, No. 3, March 1980 (a similar system optically monitors capillary blood volume in the finger while a servoed cuff maintains a constant optical reading). The former method yields a continuous pressure reading but blocks venous return flow so that monitoring must be interrupted frequently. The finger pressure waveform of the latter method is distorted relative to the important pressure waveform loading the heart and central arteries.

D. K. Shelton and R. M. Olson, "A Nondestructive Technique To Measure Pulmonary Artery Diameter And Its Pulsatile Variations", *J. Appl. Physiol.*, Vol. 33, No. 4, Oct. 1972, used an ultrasound transducer in the esophagus to track canine pulmonary artery diameter. They reported approximate short-term pressure/diameter correlation, but Itzchak et al, "Relationship of Pressure and Flow to Arterial Diameter", *Investigative Radiology*, May–June, 1982, using ultrasound to track canine systemic arterial diameter, found no useful longterm pressure/diameter correlation. Hence, it is doubtful that blood pressure can be calibrated against measured vessel diameter for purposes of continuous monitoring.

In other areas of the human body, Kahn, U.S. Pat. No. 3,598,111, describes a mechanically and acoustically tuned pneumatic system, useful at a single frequency, for measuring the impedance of the air passages and tissues of human lungs to obtain a two-component trace (representing resistive and reactive impedance) as a function of time.

SUMMARY OF THE INVENTION

The object of the invention is to induce low frequency vibrations in an organ or blood vessel using a surface vibration driver, measure what the driver "feels" at the surface (e.g. mechanical impedance), and measure the vibrational motion induced in the organ or vessel (e.g. by ultrasound). These measurements are typically analyzed at several frequencies and correlated with a mathematical model of the vibrating system, to determine significant unknowns. If the organ or vessel has internal pressure that changes with time, then analysis of data at two or more pressures results in a much tighter correlation with the mathematical model, so that absolute pressure and tissue properties such as artery wall stiffness can be determined quite accurately.

The system uses a driver to induce vibrations below 20 KHz into underlying body structures, including organs, fluid-filled organs and segments of blood vessels. The driver includes apparatus for determining parameters of the vibrational excitation applied to the patient, e.g. applied forces or velocities, usually both. Means are provided for sensing structure vibrational motions, e.g. ultrasound, or visual impressions of a stroboscopic display for an ocular approach. Structure dimensions may also be sensed. A computer-controller includes signal-processing equipment and signal interfaces with the sensors. The system obtains sufficient response data related to differing frequencies and, in some cases, to differing pressures, to infer data about the mechanical impedance of the body structure in its local surroundings, and utilizing that impedance data, to infer mechanical parameters of the structure. These parameters may include such intensive tissue or fluid parameters as density, shear modulus, rate of decay of shear modulus due to creep, shear viscosity, and internal pressure; and may also include such extensive or whole-structure parameters as effective vibrating mass or the stiffness of an artery wall.

The computer-controller includes algorithms to infer physical parameters of the structure from the performance and data of the driver and sensing apparatus. These algorithms include at least one of the following:

(1) Network Algorithm, derived from linear network theorems, particularly the Theorem of Reciprocity, which provides there is a useful symmetry for vibration transfer from driver to structure and structure to driver. This algorithm can be applied where time-variation in internal pressure generates at least two distinguishable vibration response patterns at a single frequency.

(2) Simulation Algorithm, including a mathematical simulation model of a structure and its surrounding environment, and sometimes also of the coupling between the driver/sensor assembly and the structure. Parameters of the model are adjusted to optimize the fit between simulated and measured responses. The spectrum of data used for a simulation algorithm is derived at least in part from differing frequencies of driver excitation.

(3) Analytic Function Fit Algorithm, an abstracted simulation approach ignoring structural detail, uses frequency variation data to deduce mass per-unit-length and pressure in a cylindrical vessel, or total mass and the product of pressure times radius in a spherical organ.

Where a network algorithm can be applied, simulation is simplified. Network analysis provides an accurate model for the transfer of vibration energy between driver and structure, substantially independent of the detailed structure of the organ, the driver and intervening tissues. The network analysis reveals the mechanical vibrational impedance of the structure in its local surroundings. Impedance determinations at several frequencies are then incorporated into a simulation analysis without need to model the complicated coupling between the driver and structure. Network results are frequently applied to the analytic function fit algorithm, avoiding the more difficult generalized simulation algorithm.

Where vessel wall stiffness mimics internal pressure, analysis of two different vibration modes aids in distinguishing the separate effects of stiffness and fluid pressure.

Four embodiments of the system illustrate combinations of measurements that determine the mechanical impedance of an organ or vessel in its local surroundings, permitting determinations of pressure and/or tissue properties. Simplified systems taking fewer measurements sometimes yield useful data, while added measurement capabilities often yield better data.

In one aspect of the invention for measuring systemic arterial blood pressure, an elongated vibration driver is disposed in contact with the skin, the long axis parallel to the artery. The vibrational velocity of the driver surface is measured, as is the applied vibrational force over a central segment of the driver. A pulsed ultrasound system measures the time-varying depths of the near and far walls of the artery segment under test, along three cross-arterial axes in the same plane. Circuits correlate ultrasound depth variations with the audio driver vibration signals, to determine the amplitudes and phases of vibrational velocities associated with the three changing diameters and center-depths. These multi-axis vibration correlations are resolved into components of vibration mode shapes. Blood pressure variation over time alters the response phases and amplitudes of these modes. These vibration response alterations in turn affect the surface vibration force and velocity measurements. This blood-pressure-induced change data enables the computer, via a network algorithm, to deduce arterial impedance for one or more mode shapes. The network algorithm is applied repeatedly at different frequencies, to determine the frequency-dependence of an arterial mode impedance at a single pressure. The impedance versus frequency data enter a simulation algorithm, which infers absolute pressure. It is usually necessary to use simulation results to correct the network solution, leading to an iterative simultaneous solution of network and simulation algorithms. For an individual patient, the system establishes a table of pressures and vibration parameters, all expressed as functions of arterial radius. For rapid computation of a pressure waveform point, the system interpolates from the table the reference pressure and vibration parameters for the currently-measured radius. The difference between tabulated and current vibration parameters reveal, via the network algorithm, the difference between tabulated pressure and actual current pressure. In this way, a graph of pressure is plotted as a function of time.

If the artery can be excited at close range, it is possible to resolve both two- and three-lobed arterial vibration mode amplitudes and phases from the ultrasound data. The dual-mode data are analyzed to yield two pressure values, one for the two-lobe mode and one for the three-lobe mode. The three-lobe pressure is more sensitive than the two-lobe pressure to wall stiffness artifacts. The difference between the two computed pressures is therefore used to discern true fluid pressure and a wall stiffness parameter.

In another aspect, the invention is configured primarily to determine the impedance of whole vibrating organs. (In the artery-pressure aspect just described, only a segment of a cylindrical vessel was excited. Analysis was based on force at the driver center and a substantially two-dimensional cross-sectional response.) According to this aspect, the driver induces vibrations while its velocity and total applied force are inferred from driver electrical responses. An ultrasound system whose beam is aimed in two dimensions measures vibrational velocities of the near and far walls of an organ. For fluid-filled organs, e.g. a urinary bladder, the system determines internal pressure. The system also discerns pressure gradients in organ tissues, e.g. from edema. If pressure changes significantly over time, e.g. from urine accumulation or changing tonus of the muscular wall of the bladder, the system uses a network algorithm to compute an especially accurate organ vibrational impedance, leading to a correspondingly accurate internal pressure.

In the absence of pressure-change data, the system infers organ vibrational impedance through detailed simulations. Parameters of the simulated structure are adjusted until mathematical performance substantially matches actual measured data at several frequencies. Adjusted simulation parameters indicate corresponding properties of the underlying organ. Where internal pressure is present, it can be inferred from simulation results.

For organs that are not hollow, some simulation parameters correspond to average intensive tissue parameters of the organ: density, shear modulus, viscosity, and sometimes even frequency-variations of modulus and viscosity. Where changes of clinical interest affect these tissue parameters, this aspect has applications as a diagnostic tool, e.g. in instances of cirrhosis of the liver or cystic kidney disease.

Still another aspect of the invention, useful for measuring intraocular pressure, is similar to the last-described aspect of the invention, except that visual impressions and user feedback replace ultrasound as a means of sensing vibrational motions in the eye. In one preferred embodiment, vibrations are induced from the driver through the lower eyelid, avoiding uncomfortable direct contact with the eye surface. Eyelid surface forces and velocities are inferred from driver electrical responses over a wide frequency range. Resonance of the eyeball is measured by a combination of eyelid surface responses and user feedback. The user watches a time-varying display, e.g. on which a horizontal line on a black background strobes, alternately, red and blue-green, at points 180° out-of-phase on the vibrator applied-force sinusoid. For a computer-determined phase setting, the user adjusts frequency until the strobing lines appear to converge into a single white line, indicating synchronization of the strobe with eyeball vibrations. If the lines pulsate perceptably in and out of convergence with each heartbeat, the user is instructed to adjust the frequency to the two outer limits where convergence is just barely achieved at the maximum fluctuations. These settings tell the system the frequency at which a specified vibrational phase is achieved, and how much that frequency varies with intraocular pressure pulsations. The system also strobes a dot whose perceived image is split maximally when the lines are converged. The user adjusts driver amplitude to match the perceived dot spacing to a pair of reference dots, strobed at the zero-displacement times of the line flashes. This amplitude adjustment tells the system the excitation level needed to achieve a reference response. A final spacing adjustment of the reference dot pair gives convergence of these dots at the moment of maximum pulsatile separation from convergence of the strobed lines, telling the system the change in amplitude response due to pulsations in intraocular pressure.

Analysis of these data follows similar lines to the last described aspect, the content of the visual data being comparable to the content of the ultrasound data. The system infers the product of pressure times average ocular radius. For more accuracy and if a separate pressure determination is desired, the user measures eyeball radius, e.g. by looking into a mirror, observing reflections of two lights on the sclera (white of the eye), and matching two cursors to the reflections. It is noted that the radius-pressure product is perhaps a better indicator of glaucoma danger than pressure alone.

Another aspect of the invention is suited for measuring pressure in the pulmonary artery. In preferred embodiments, the patient swallows a cylindrical probe, which is held by a cable partway down the esophagus to rest behind the the right pulmonary artery.

The ends of the probe vibrate axially, driven by transducers that move against a gas volume inside the probe, like acoustic-suspension speaker drivers. Driver expansion/contraction and output pressure vibrations are inferred from changes in driver electrical response. Acceleration sensors detect lateral vibrations at the center and ends of the probe. The lateral movement is caused by asymmetry of the probe surroundings, which include the spinal column just behind the probe. Driver response motion, pressure and lateral movement data are combined to simulate the excitatory field geometry. Ultrasound transducers just above and below the artery-crossing level measure three angularly-displaced diameters. Time variations in the diameter data are analyzed to determine the amplitudes and phases of arterial vibration modes next to the probe. A pressure sensor facing the artery samples the local vibrational pressure field, as well as low-frequency pressure pulsations caused by the artery. This pressure sensing permits refinement of the excitatory vibration field model, which is used to extrapolate mode-excitation strength over the strongly-affected length of artery. Vibration-energy integrals over that length lead to a total energy model, permitting network algorithm solution and subsequent analytic function fit algorithm solution for pressure. By interpreting the decay of the diastolic pressure curve, the system infers pulmonary capillary pressure.

According to another aspect of the invention, a method for inducing vibrations in a selected element of the human body and detecting the nature of responses for determining mechanical characteristics of the element non-invasively, comprises steps of: inducing multiple-frequency vibrations, including below 20 KHz, in a selected element of the body by use of a driver means, determining parameters of the vibration exerted on the body by the driver means, sensing variations of a dimension of the element of the body over time, including in response to the driver means, correlating the variations with frequency components of operation of the driver means below 20 KHz to determine corresponding frequency components of the variations, resolving the frequency components into components of vibration mode shape, and interpreting the parameters of vibration exerted by the driver means and the components of vibration mode shape in a manner to determine the mechanical characteristics of the element.

In preferred embodiments determination of parameters of vibration exerted by driver means includes determining force, or determining velocity; a mechanical characteristic determined is pressure; the method further comprises the step of detecting change in components of vibration mode shape due to pressure change in the element, change being included in determination of the mechanical characteristics of the element; the multiple-frequency vibrations are generated by changing the operation frequency of the driver means over time; the multiple-frequency vibrations are generated by operation of the driver means at multiple frequencies simultaneously; the body element includes a wall, and the method further comprises the steps of: resolving the components of vibration mode shape for at least two modes, and comparing the determined mechanicl characteristics of the elements respectively determined on the basis of the components of vibration mode shape for at least two modes in a manner to provide an indication of element wall stiffness; the method comprises sensing the variations of a dimension of the element of the body by means of ultrasound echo signals; a mechanical characteristic determined is systemic arterial blood pressure and the body element is a segment of the arterial system; a mechanical characteristic determined is the mechanical impedance of a body element and the body element is an entire organ; a mechanical characteristic determined is intraocular pressure and the body element is an eyeball, preferably the step of sensing variations of dimension comprises sensing variations of a dimension of the eyeball wherein the method comprises incorporating user feedback in response to visual impressions of a time-varying display, the visual impressions being representative of the response of the eyeball induced by the driver means; a mechanical characteristic determined is pulmonary blood pressure and the body element is a segment of the pulmonary arterial system; in addition to the step of sensing varitions of a dimension of the element, the method further comprises sensing a dimension of the element, the sensed dimension being included in determination of the mechanical characteristics of the element, preferably the dimension of the element is sensed by interpreting ultrasound echo signals, and preferably the dimension of the element is sensed optically; and the method further comprises applying a known pressure to the element in a manner to permit calibration, preferably the method further comprises applying the known pressure by means of a pressure cuff.

Other features and advantages of the invention will be understood from the following description of the presently preferred embodiments, and from the claims.

PREFERRED EMBODIMENTS

FIG. 3 is a sectional view of the vibration driver and sensor assembly of FIG. 2 taken along the line 3—3, while

FIG. 4 is a sectional view of a vibration driver assembly;

FIG. 5 is a diagrammatic representation of arterial vibration modes;

FIG. 6 is a block flow diagram of low-frequency data acquisition and control;

FIG. 7 is a block flow diagram of ultrasound data acquisition and control;

FIG. 8 is a block flow diagram of the ultrasound depth-tracking;

FIG. 9 is a simplified circuit diagram of the depth-tracker subassembly of FIG. 8;

FIG. 10 is a representation of electronic waveform traces of FIG. 9;

FIG. 11a is a representation of the vibration drivers and sensors in a whole-organ measurement aspect of the invention viewed from above, while

FIG. 12a is an enlarged view of the ultrasound-transducer aiming system of FIG. 11 from above, while FIG. 12b represents magnetic fields of FIG. 12a and FIG. 12c is a side section view;

HARDWARE AND OPERATION OF THE INVENTION

Essential Hardware

Figure 1:
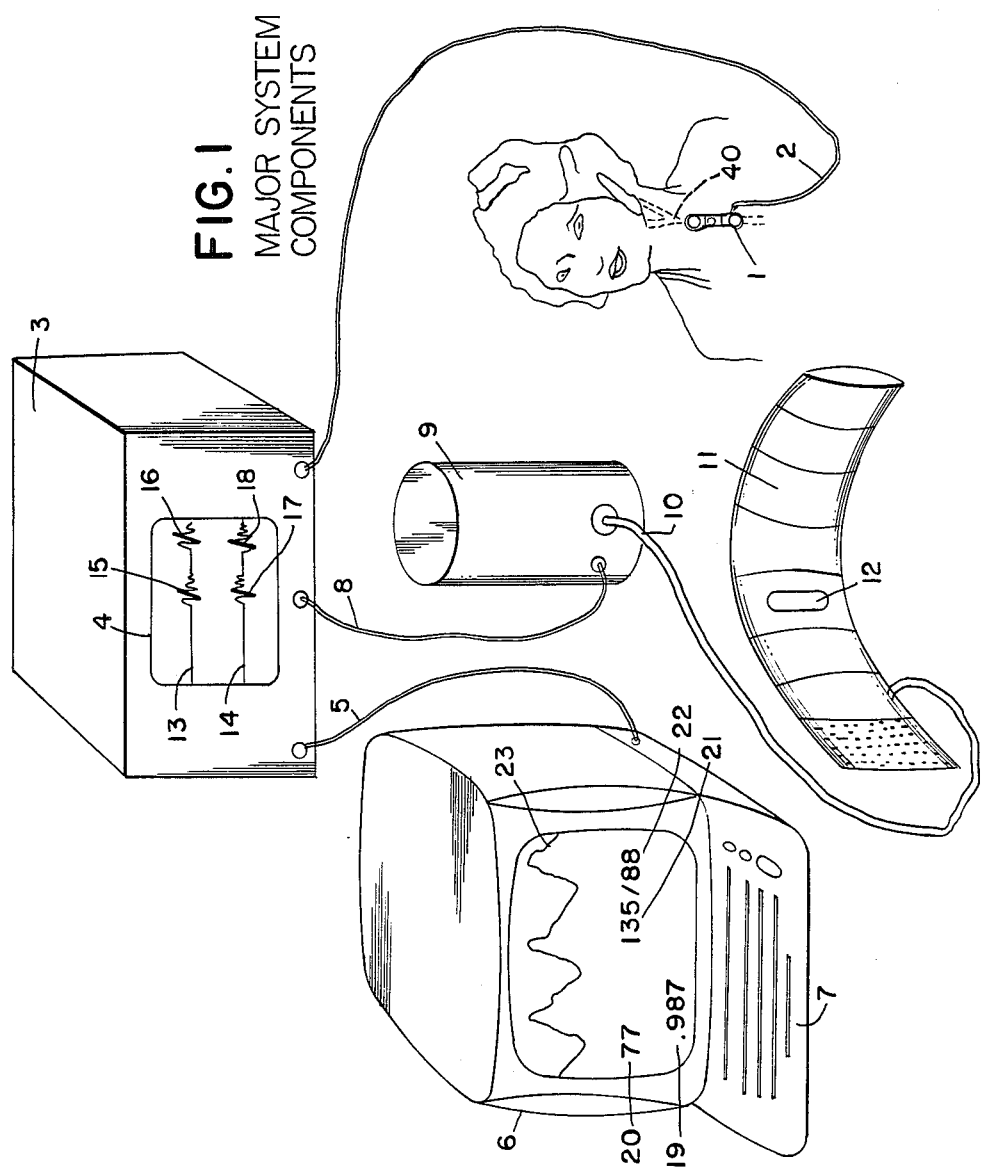
FIG. 1 is a diagrammatic perspective view of the system according to a preferred embodiment of the invention for measuring systemic arterial pressure.

The principal subassemblies of the invention in an aspect for measuring systemic arterial pressure are illustrated in FIG. 1. Vibration driver and sensor assembly 1 is adapted to be affixed to the skin of the patient, e.g. above left common carotid artery 40 shown in dashed outline. Cable 2 connects assembly 1 to computer-controller 3, which includes oscilloscope display 4 for observing ultrasound depth signals. Cable 5 couples computer-controller 3 to video display terminal 6, including keyboard 7. Cable 8 couples computer-controller 3 to pressure-regulating air pump 9, which is coupled in turn by tube 10 to inflatable pressure cuff 11. This cuff includes inset 12 on its inner surface, allowing it to fit over assembly 1, around the neck. The cuff is for optional calibration, to verify or improve system accuracy by applying a known tine-varying pressure perturbation, typically much less than diastolic pressure. The correlation slope relating cuff pressure change and vibration-determined pressure change indicates scaling accuracy. Oscilloscope traces 13 and 14 show ultrasound echoes taken from two angles across artery 40. Intensified segments 15 and 16 show echo regions being tracked, corresponding to near- and far-wall artery depths, for one ultrasound angle. Segments 17 and 18 show the corresponding tracked depths for the other ultrasound angle. On the display of terminal 6, the decimal number indicated by 19, e.g. the value 0.987 as shown, is an indication of the average of the squares of the signal trace slopes for echo segments 15, 16, 17 and 18. This signal strength indication is referenced to unity for the strongest signal previously encountered, so that it can be used to compare current alignment of assembly 1 with the "best" previous ultrasound alignment. The number indicated by 20, e.g. the value 77 as shown, is heart rate per minute, derived from blood pressure pulsations and averaged e.g. over the ten most recent pulses. The numbers indicated by 21 and 22 and separated by a slash mark, e.g. 135/88 as shown, indicate systolic and diastolic blood pressure in mm Hg, averaged e.g. over the ten most recent cardiac cycles. Optionally, the system can display arrhythmia count over a specified time period ending at the present time, again derived from blood pressure data. Finally, trace 23, which moves from right to left as the trace is extended on the right, displays the blood pressure waveform determined by the system.

Figure 2:
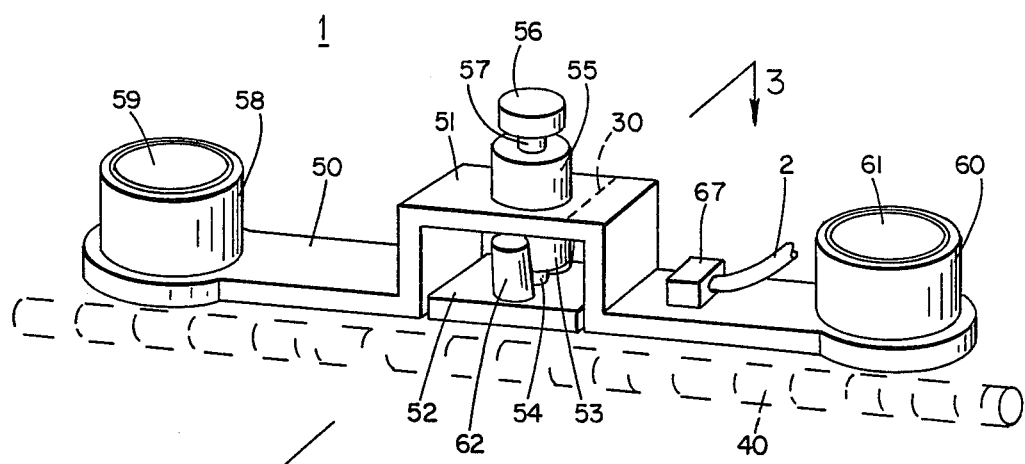
FIG. 2 is an enlarged perspective view of the vibration driver and sensors of FIG. 1.

Assembly 1 is illustrated in greater detail in FIG. 2. Vibrator plate 50 extends the full length of the assembly and includes a central elevated bridge section 51. Plate 50 is configured to contact the skin surface except over the elevated central section. Plate segment 52 fills the gap under segment 51, except for small decoupling gaps at the left and right ends, to contact the skin and provide continuity to the contact area of plate 50. Segment 52 is held substantially rigidly with respect to bridge section 51 of plate 50 by axial post 54 from load cell 53. Using a stiff piezoelectric ceramic strain gauge with a charge amplifier, load cell 53 measures the axial force along post 54 with negligible compliance at audio frequencies and with the forces involved. Load cell 55 is similar to cell 53 and measures axial force exerted by electronic assembly 56 on post 57. Assembly 56 serves as a countermass, so that the combination of parts 55, 56 and 57 acts as a transducer for accelerations along the vertical axis common to posts 54 and 57.

Positive and negative DC supply voltages arriving through cable 2 into junction box 67 drive strain gauge charge amplifiers in load cells 53 and 55. Output signals from the charge amplifiers of cells 53 and 55 are coupled to two wires in cable 2, via junction box 67. These signals are received by computer/controller 3 for further processing and digital conversion. Part of the force reading comes from the inertial mass of plate segment 52 and post 54, while the remaining force signal comes from the reaction of vibrated tissues in the patient over the left-to-right length of segment 52. The acceleration signal in computer/controller 3 is integrated over the frequency band of vibration driver excitation, resulting in a signal that closely approximates velocity over that frequency band. Highpass filtering to cut off frequencies below about 20 Hz results in a zero-average velocity signal.

The vibration driver consists of open-ended cylindrical housings 58 and 60, containing respective internal driver and reaction mass assemblies 59 and 61, the housings being affixed to the ends of plate 50. Wires in cable 2 provide AC excitation for parallel-wired assemblies 59 and 61. The excitation signal originates from a digital function generator in computer-controller 3. This generator produces a periodic waveform having typically six harmonic sinusoidal components. The waveform is stored digitally and played out cyclically and repetitively into a D to A converter, whose analog output goes to a power amplifier with lowpass filtering. In response to this excitation, assemblies 59 and 61 vibrate up and down together, exerting a reaction force via housings 58 and 60 on plate 50. Plate 50 and instrumented segment 52 vibrate together, substantially as a rigid body, transmitting force through the contacting skin area and inducing vibrations in the shape of underlying artery 40, as illustrated in the cross-section of FIG. 3.

Figure 3:
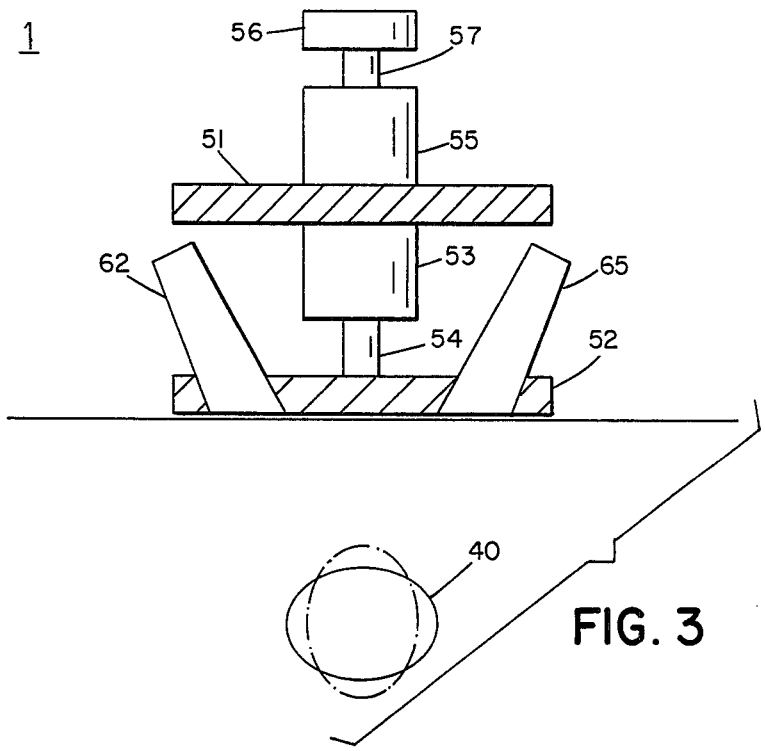

Matched ultrasound transducer assemblies 62 and 65 lie on either side of segment 52, aiming down through the segment so that the beams cross at a typical artery depth. Assembly 65 is obscured in FIG. 2 but is shown in FIG. 3. Cable 2, via junction box 67, provides coupling of ultrasound electrical signals to and from assembly 1. Assembly 56, besides serving as an accelerometer countermass, contains ultrasound electronics for receiving a drive signal from Cable 2, boosting that signal to drive a selected transducer, switching to select alternate transducers on alternate transmit cycles, switching both transducers to receive mode after pulse transmission by one of the transducers, preamplifying return echo signals from both transducers, and driving those signals into cable 2. The DC power supply voltages used for the strain gauge charge amplifier are also used to power the ultrasound electronics in segment 52. Cable 2 carries DC supply voltages, an ultrasound output signal, two ultrasound receive signals, ultrasound control signals, the low frequency vibration drive signal, and the strain gauge signals representing detected low frequency force and acceleration. Finally, Cable 2 provides grounding and shielding between wire groups, as needed to prevent signal interference.

Figure 3A:
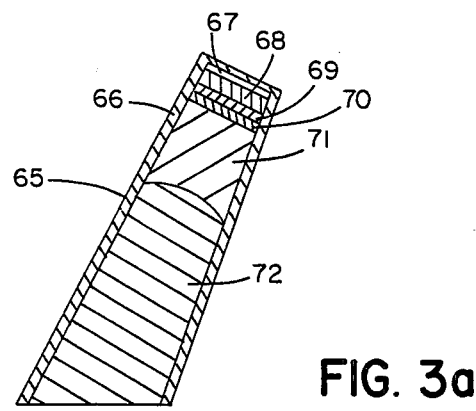
FIG. 3a is an enlarged side section view of one of the ultrasound transducer assemblies of FIG. 3.

Vibration plate 50 is oriented with its long axis parallel to artery 40. Ultrasound assemblies 62 and 65 detect arterial diameter at two angles, as shown in FIG. 2 and in the cross-sectional perspective of FIG. 3, top. The sectional plane is parallel to the ultrasound plane defined by the axes of transducers 62 and 65, which includes the vertical axis common to load cells 53 and 55. The section in FIG. 3 is taken just to the right of load cells 53 and 55, along line 3—3 and dashed line 30 of FIG. 2, so that it cuts through segment 52 and bridge section 51 of plate 50. In FIG. 3, an ellipse-mode vibration in artery 40 is indicated by the solid and dashed elliptical coutours. FIG. 3a shows a cross-section of ultrasound transducer assembly 65. The internal details of transducers 62 and 65, discussed later, are the same, since the two assemblies are matched.

Basic Operation

A preliminary description of system operation follows. In a typical application, the patient's neck is lubricated with an ultrasound transmission gel and assembly 1 applied above a common carotid artery. Oscilloscope display 4 initially shows the operator two ultrasound echo traces, displayed one above the other, corresponding to the alternating transmit-receive cycles of assemblies 62 and 65. Horizontal displacement across screen 4 represents echo delay time or, equivalently, depth, while the vertical deflections represent reflected acoustic pressure. The ultrasound signal has been subjected to phase and amplitude correction to maximize depth resolution.

The transducer assembly is manually centered over the artery by matching the depths of the two echo traces. The operator adjusts rotational alignment so that the artery axis lies, as nearly as possible, perpendicular to the ultrasound plane defined by the two ultrasound beam axes. (If the artery axis does not lie parallel to the skin surface, this causes an irreducible angle error.) This alignment is achieved by maximizing the amplitudes of the two pairs of wall echo traces while maintaining matched depths.

As the operator approaches correct transducer position and alignment, pattern recognition programs in the computer/controller identify the echo complexes of the near and far artery walls for the two displayed ultrasound signals. The machine-recognizable artery echo identification patterns are: (1) approximate depth matching of the two pairs of wall echoes, assured by operator adjustments; (2) expected ranges of average depth and spacing for each near-far wall echo pair, based on typical human anatomy; and (3) pulsating echo spacing, resulting from pulsating artery diameter. When the wall echo complexes are machine-identified, the vibration driver is activated and the computer fine-tunes the depths sampled. Specifically, the controller includes phase-lock loop circuitry capable of tracking the depth (i.e., the ultrasound signal delay) of a rapidly-repeated echo signal zero-crossing in a wall echo complex. The computer intervenes in the phase-lock circuit operation to select the zero-crossing to be tracked. A zero-crossing is sought that has a relatively steep slope and whose vibrational motion is large, such that the product of slope times vibration response amplitude is maximized. More specifically, the vibration amplitude to maximize is amplitude relative to the opposite artery wall, so that ultimately the zero-crossing selection is for a pair of zero crossings with large relative motion. The vicinities of the selected zero-crossings are highlighted by oscilloscope beam intensity modulation, as illustrated at 15, 16, 17 and 18.

A digital readout of average wall echo signal strength appears on the screen of terminal 6, to assist the operator in fine-tuning the alignment. The decimal fraction displayed (at 19) becomes 1.000 whenever response amplitude matches or exceeds all previous values. As amplitude declines, the reading indicates response strength as a fraction of the largest achieved. The operator thus learns the best alignment by crossing it, and then returns to the position of maximum signal strength.

Ultimately, the system locks onto three pairs of wall-depth signals, representing three angles across the artery: one for assembly 62, one for assembly 65, and the final pair for a transverse signal where assembly 62 sends the pulse and assembly 65 receives the echo (or vice versa). Trigonometric computer operations give a scaling correction factor for the transverse echo, so that the depth sensitivities of the three depth pairs are computationally matched.

If extended monitoring is contemplated, assembly 1 is now affixed more permanently to the skin. The position is marked with ink dots on the skin, the assembly is removed, and the ultrasound gel is wiped off. A specially cut and marked piece of double-stick surgical adhesive tape is placed on the skin, aligned to the marks. Assembly 1 is applied to the upper adhesive surface of the tape, in the original position and alignment. The tape makes an efficient ultrasound and audio vibration interface.

If extended monitoring is not contemplated, the transducer assembly may be held in place manually.

Once in place and operating, assembly 1 induces vibrations through the skin into the underlying artery. The surface vibration velocity is derived, over the driver frequency band, from the acceleration signal of load cell 55, as described above, while the corresponding force, sampled over the known length of segment 52, is derived from the output of load cell 53. Plate 50, including the gap-filling segment 52, is of constant width in the middle and widens at both ends to minimize vibrational "end effects", so that the vibration field under segment 52 extending down through the artery depth shows minimal axial variation. Thus, all vibrational motions below segment 52 lie nearly parallel to the ultrasound plane (defined by the axes of transducers 62 and 65). The ultrasound plane should lie substantially perpendicular to the artery axis. Hence, for an arterial segment directly below driver segment 52, and whose length equals the length of segment 52, the vibrational energy coupled to and from that artery segment should correspond closely to the energy coupled to and from driver segment 52. This symmetry permits a proper scaling of sensed parameters to infer blood pressure. The measured force and velocity for driver segment 52 define the instant-by-instant energy flow through this segment. The ultrasound measurements through the three angularly-displaced diameters of artery 40 suffice to define the significant vibration mode responses induced in the artery. Blood pressure variations alter the vibrational properties of the artery. The resulting changes in the signal measurements reveal coupling coefficients characterizing the dissipative and reactive components of force and energy transfer between driver segment 52 and the corresponding artery segment. Further analysis reveals the mechanical impedance of the artery and nearby coupled tissues. Frequency analysis of this arterial mechanical impedance reveals blood pressure, as perturbed by artery wall stiffness. Analysis of two separate vibration modes for apparent pressure reveals separated wall stiffness pressure artifacts and true fluid pressure.

Ultrasound Transducer Details

Referring to FIG. 3a, housing 66 includes air space 67 behind piezoelectric ceramic transducer disk 68, fabricated e.g. of lead titanate zirconate, metallized on the flat surfaces and axially poled, e.g. as manufactured by Edo Corp., Western Division, 2645 South 300 West, Salt Lake City, Utah 84115. (The same material is appropriate for use in low-frequency strain gauge assemblies 53 and 55.) The metallizations on the front and back of the disk are typically coupled to the higher-impedance winding of one of the torroidal transformers in assembly 56. Bonded to the front surface of disk 68 are two acoustic interface layers, 69 and 70, which present a graduated change in acoustic impedance from the high impedance of the disk to the low impedance human tissues. The thickness of each layer is approximately ¼ wavelength at the design center frequency of the transducer. Layer 69 may consist of quartz, and layer 70 of acrylic plastic. The ultrasound transducer acoustic interface layers and electrical matching circuitry are constructed in a manner familiar to engineers in the medical ultrasound field, e.g. as in "The Design of Broad-Band Fluid-Loaded Ultrasonic Transducers", *IEEE Trans. on Sonics and Ultrasonics,* Vol. SU-26, No. 6, November 1979.

Adjoining the front surface of interface layer 70 is an astigmatic, divergent acoustic lens. It consists of material layers 71 and 72, with an interface between them that curves relatively strongly in the "ultrasound plane" mentioned above, i.e. the plane of the cross-sectional diagram being examined, and curves weakly in the other direction. Both layers have approximately the acoustic impedance of human tissue (close to the impedance of water), and are made of a polymer of lower acoustic impedance than water, e.g. room temperature vulcanizing (RTV) silicone rubber, loaded with a fine powder of high acoustic impedance. The powder concentration is chosen to raise the low impedance of the polymer up to the desired tissue impedance value. Layer 71 is loaded with high-density powder, e.g. tungsten carbide, while layer 72 is loaded with low-density powder, e.g. graphite. The light powder raises the acoustic impedance of the polymer largely by raising the modulus, while a lesser volume concentration of the heavy powder achieves the same impedance largely by raising the density. As a result of the differing ratios of modulus to density, the speed of sound is higher in the relatively high-modulus, low density layer 72 than in the relatively low-modulus, high density layer 71. The curvature of the interface between the layers, convex away from layer 72 towards layer 71, creates the desired divergent acoustic lens. While the modulus/density ratios are caused to differ, giving differing sound speeds, the modulus-density products of the layers are matched, resulting in matched acoustic impedances and minimal interface reflections. The matched impedances are made close to that of human tissue, to minimize reflections at the lower sloping interface of layer 72 to the patient.

Powder loading of uncured silicone in layers 71 and 72 is achieved without introducing bubbles by mixing powder and uncured silicone and molding in a vacuum. Brief centrifuging settles the mixture into the mold and collapses large voids, but is not extended long enough to settle the fine particles. Upon restoration of atmospheric pressure, remaining vacuum-filled voids collapse, leaving a bubble-free mixture. Housing 66 is part of the mold, and is porous to allow air curing of the contents. After layers 71 and 72 are fabricated and cured, the surface of housing 66 is sealed by impregnation with a polymer resin.

The divergent lenses in the transducers allow the ultrasound system to tolerate differing depths of arteries in various patients. Due to the astigmatic design and low divergence outside the ultrasound plane, the system is relatively sensitive to misalignment whereby the ultrasound plane fails to cut perpandicular to the artery axis.

The ultrasound system is not intended for point-by-point imaging. Instead, the system primarily "sees" surfaces of discontinuity in acoustic impedance in the regions where those surfaces lie approximately tangent to the spreading wavefronts from the ultrasound assembly. Thus, the ultrasound system "sees" near and far artery wall depths, averaged over a significant wall surface area. This spatial averaging minimizes sensitivity to roughness and irregularity of the artery walls. The design also avoids ultrasound "hot spots" where the beam might otherwise expose a small area of tissue for prolonged periods at relatively high intensity. Apparent ultrasound-measured diameters are slightly distorted by arterial wall curvature, since effective echo averaging extends over a finite angle of curvature. Computer algorithms correct for this distortion as necessary.

Vibration Driver Details

FIG. 4 illustrates the internal construction of housing 60 and driver/mass assembly 61. Housing 58 and driver/mass assembly 59 are the same. The circular surface 61, visible in FIG. 2, in FIG. 4 is seen as the top surface of an inverted cup-shaped magnetic pole piece, viewed now in cross-section. This cup consists of annealed transformer-grade silicon steel. Inside cup 61 is permanent magnet 82, which may be a rare-earth cobalt magnet consisting, e.g. of material Crucore 18 from Colt Industries, Crucible Magnetics Division, Route #2, Elizabethtown, KY 42701. The polarization of magnet 82 is axial. An electric current in winding 83 will either reinforce or oppose the permanent field, depending on polarities. A similar electrically-variable magnetic field source is set up by silicon steel cup 84, permanent magnet 85 and winding 86. These two magnetic sources are spaced by rigid post 87, of non-ferromagnetic material. Silicon steel washer 88 sits in the gap between the two magnetic field sources. The north-south polarizations of magnets 82 and 85 are parallel and matched, so that the magnetic flux primarily follows a donut-shaped path. The dominant flux path can be traced from magnet 82 down, through an air gap, into the inner area of washer 88, through a second air gap into magnet 85, down into cup 84, up from the "rim" of cup 84, across an air gap to the outer area of washer 88, up through an air gap to the "rim" of cup 61, and finally full circuit back into the top of magnet 82.

When washer 88 is centered and no current flows through the windings, the magnetic forces on washer 88 substantially balance. Coils 83 and 86 are wound and connected so that an electrical signal that strengthens the fields crossing the upper air gap will correspondingly weaken the fields crossing the lower air gap. This will unbalance the attractive forces, creating a net axial force between washer 88 and the driver/mass assembly.

The axial position of washer 88 relative to the driver/mass assembly is restored by silicone rubber o-rings 89 and 90. The o-rings rest in grooves in windings 83 and 86, with the outer walls of the grooves being the inner surfaces of cups 61 and 84. The windings are resin-impregnated and cured for dimensional stability. The o-rings contact washer 88 only at a circularly-arrayed set of teeth or ridges, illustrated landing in the cross-section of the diagram at 91 and 92. The contact areas of the teeth are curved to follow the round surface of the o-ring, to provide a radial centering force for the washer. The tooth area is chosen to provide the desired restoring force on the washer, enough to overcome the destabilizing influence of the magnetic field and achieve resonance with the inertial load at a desired frequency. When shocked, the washer can contact the entire circumference of an o-ring, which cushions impact force.

Open cylindrical housing 60, as seen in this detailed drawing, is split and includes separable lower and upper sections 93 and 93'. The sections are bonded together to capture washer 88, and the lower end of section 93 is bonded to plate 50. Housing sections 93 and 93' are non-ferromagnetic to avoid diverting flux from the axial gaps. The dashed line at 94 indicates an optional flexible diaphragm to bridge the top of the gap between 60 and 61 and keep dust and especially ferrous particles away from the magnetic gaps.

The leakage flux from the driver/mass assembly will be a steady dipole field and, primarily, a quadrupole AC signal field. The AC component of the field travels radially in the washer and splits roughly symmetrically to travel up and down to cups 61 and 84. Since quadrupole fields lose strength rapidly with distance, unwanted AC magnetic signal couplings are minimized. Washer 88 can be made relatively thin, within minimum stiffness constraints, without causing magnetic saturation, since only signal fields and not the large permanent polarizing field pass radially through the flat plane of the washer disk. For small motions, electro-mechanical efficiency is very high, with a high ratio of response force to input wattage determined by the relatively large available winding volume and the strong polarizing fields in the gaps. The symmetry of the structure minimizes second-order distortion responses. Most of the mass of the assembly is concentrated in the moving element, which includes the permanent magnet, most of the silicon steel and the windings. This transducer is useful for driving high mechanical impedances and for minimizing the mass of one moving part by concentrating the mass in the oppositely-moving part.

OPERATING PRINCIPLES OF A SYSTEMIC ARTERIAL PRESSURE EMBODIMENT

The Fundamental Pressure-Determining Steps

A preferred set of procedural steps for determining time-varying absolute systemic arterial blood pressure follows:
(1) Vibrate the skin surface to excite the underlying artery at multiple frequencies.
(2) Assure, by design and operational adjustment, that vibrational symmetry is maintained for a length of the arterial axis, so that energy relations along a given surface length correlate with energy relations along a corresponding parallel length of underlying artery.
(3) Measure the vibrational force applied along that given surface length, and resolve that force, over brief time windows (e.g. 50 milliseconds), into sinusoidal phase and amplitude components at the multiple frequencies of vibrational excitation.

(4) Measure the vibrational velocity whose product with the force measured in step 3 equals the instant-by-instant power transfer into the given surface length paralleling the artery. As with the force, resolve the velocity, over brief time windows, into sinusoidal phase and amplitude components.

(5) Resolve the ultrasound wall echo depth data into rates-of-change, i.e. vibrational velocities. As with the force and velocity measurements above, resolve the ultrasound velocity signals, over brief time windows, into sinusoidal phase and amplitude components. For each resolved set of vibrational velocity components at each excitation frequency, reduce the data into vibrational phases and amplitudes of significant low-order components of vibration mode shape.

(6) Network Algorithm-For each pressure-sensitive vibration mode shape, as resolved into phase/amplitude components for a given frequency and two distinct time windows, determine the vibrational force-/velocity transfer factor that relates measured surface force to measured mode velocity. Where only a single mode shape is significant and change in artery diameter with pressure change is negligible, this transfer factor equals the ratio of pressure-induced changes, from one time window to the other, in surface force and mode velocity. Where two or more pressure-sensitive vibration modes are significant or where arterial diameter changes significantly with pressure, the force/velocity transfer factors for each mode must be determined from simultaneous solution of the network algorithm with a simulation algorithm (below). Because of a necessary symmetry of vibrational energy transfer, each transfer factor thus determined equals the ratio of unknown surface force to known vibration-mode velocity. Finally, the unknown vibration force distribution(s) driving the significant mode shape(s) is (are) determined.

(7) Using the results from 6, compute the arterial vibrational impedance for each significant pressure-sensitive mode, i.e. compute the effective net force correlated with a given mode shape distribution, and divide that force by the measured mode-shape velocity response to obtain impedance. The division uses complex arithmetic, since both force and velocity are sinusoids having amplitude and phase. For a given mode, impedance variation over tim is a strong indicator of blood pressure variation.

(8) Through repetitions of the above steps for different frequencies, establish the lowest-order arterial vibration-mode impedance as a function of frequency for a single value of blood pressure (typically for a single sample time window as described above).

(9a) Analytic Function Fit Algorithm-Because of changes in artery wall properties over time, it may be feasible to establish two distinct data sets, from two sampling time windows, such that pressures differ but arterial diameters match. In this case, solution for arterial vibrational impedance versus frequency is possible in one step. Then, using known general characteristics of arterial impedance as a function of frequency, use a complex analytic function-fit to the above impedance-versus-frequency data at constant pressure to establish the dominant low-frequency limit term of the impedance function. This limit term establishes an absolute blood pressure, with possible additive wall-stiffness artifacts.

(9b) Simulation Algorithm-Where data sets at differing blood pressures and equal artery diameters cannot be obtained, or where a more accurate result is needed, a generalized vibration simulation model is fitted to measured data. In this case, initial network algorithm solution for arterial impedance (step 7) is approximate, and simulation results based on this impedance solution are fed back to correct the impedance determination. Hence, the best-fit parameters of the simulation model are determined iteratively, correcting the artery impedance estimates on each iteration.

(10) (Optional) Repeat step 9a for the same reference pressure and a different vibration mode, establishing a second value for absolute blood pressure. This value will differ from the value of step 9a in direct proportion to wall stiffness. A proportion of the difference between these two results is subtracted from the reference pressure of step 9a to give baseline fluid pressure, now independent of wall stiffness. In the more generalized simulation approach of step 9b, data on both observed vibration modes are used to constrain a simulation model whose parameters represent blood pressure and artery wall properties.

(11) Repeating steps 1 through 9, establish a table of pressures and associated vibration parameters as functions of radius, for a single frequency. With this table calibrated to the sensor/patient linkage, real-time pressure tracking is accomplished by table lookup and network algorithm correction to current pressure, using current vibration parameters. Real-time pressure update computations are much simpler than the initial absolute pressure determinations.

In deriving detailed operating algorithms, we first concentrate on a common situation in which only one pressure-sensitive vibration mode is measurably excited, specifically the ellipse-mode vibration illustrated in FIG. 3. Where modes of higher order than the ellipse-mode cannot be resolved, it is impossible to complete step 10, and consequently it is difficult to determine wall stiffness artifacts accurately. Real-time pressure may then be computed with an estimated additive wall-stiffness error. Except in patients with advanced arteriosclerosis, this wall-stiffness error is small.

Pressure and Frequency Baselines

By analogy to vision, the system gains "parallax" on the measured quatities, to gain "perspective" into the underlying mechanics, through "movement" along either of two separate baselines-blood pressure difference and frequency difference. The blood pressure difference baseline is established over time as blood pressure changes. Commonly only two points along this baseline are needed, one for a high pressure sampled just after the systolic rise, and another for a low pressure sampled shortly before a systolic rise. The frequency difference baseline is typically established for each of the pressure baseline points by frequency analysis of the data in the two time samples.

If everything remains constant except for pressures and frequencies, then solution for pressure is relatively straightforward. Artery radius variation (or organ radius variation in a more general context) generally enters in as a third significant baseline to complicate matters, however. A goal in data collection, not always achievable, is to wait for or try to induce changes in muscle tonus of the artery or organ wall. This muscular variability in the measured system can offset undesired correlation between pressure and radius. For example, if the smooth muscles in an artery under observation tighten during a monitoring period, then a given monitored radius will occur at a higher pressure than previously, and this will provide a pair of time samples at differing pressures and matched arterial dimensions. The muscular change can be encouraged, in some instances, by applying finger pressure to the artery to force an alteration in flow, inducing compensatory wall-muscle activity. The detailed discussion to follow deals primarily with this simplifying situation of time samples with pressure difference and constant geometry.

Where time sample pairs at differing pressures cannot be found at matched radius, a generalized simulation algorithm is needed for complete solution. Approaches useful for such simulations will be mentioned briefly at the conclusion of this writeup. A more comprehensive writeup is necessarily lengthy and appropriate for a selected audience of mathematicians. This writeup concentrates on what the simulations do and how they contribute to the function of the invention.

Properties of Impedance Phases

Engineering practice usually defines inertial velocity impedance as having a phase angle of +90°, which leads approximately, but not exactly, to a linear frequency dependence. Because of the frequency-dependent influence of viscous shear forces on vibration field geometry, the effective moving mass of a vibration mode is frequency-dependent. Extra mass is entrained by shear forces at low frequencies. Hence, inertial velocity impedance does not decline as fast as the first power of frequency at low frequencies.

Restoring velocity impedance has a phase angle of −90° and varies almost exactly as the reciprocal of frequency. The reciprocal relationship is substantially exact for blood pressure and less exact for stiffness pressure, which may decline slightly at low frequencies due to visco-elastic creep. Since stiffness pressure is usually a small correction term, its gradual frequency dependence can usually be ignored. Because of its reciprocal-frequency dependence, restoring impedance dominates overall impedance in the low-frequency limit. Determination of a mode-shape restoring force coefficient (per unit length) to match arterial impedance in a low-frequency limit constitutes determination of blood pressure plus a possible additive wall-stiffness term. Since inertial and restoring impedances together determine net 90° impedance, determination of blood pressure amounts to determining and subtracting out the inertial impedance term from the 90° impedance data, revealing the pressure term.

Damping velocity impedance is zero-phase impedance. Because of the phase, this impedance is measured independent of inertial and stiffness impedances. This does not make damping impedance irrelevant to separating inertial and stiffness impedances. Rather, changes in damping impedance are correlated with changes in inertial impedance, since both relate to common underlying changes in vibration-mode geometry with changing frequency. Damping impedance tends to increase weakly with frequency as shear boundary layers become thinner and shear-gradients correspondingly steeper, leveling off at high audio frequencies as boundary layer thicknesses approach the pressure-containing arterial wall thickness. For the purposes of this analysis, mode-shape coefficients for restoring-constant, velocity-damping and mass (all per-unit-length) may be approximated to approach definite high- and low-frequency limits. Though this is not rigorously true (e.g. compressibility effects invalidate this model above the audo frequency range), the approximation leads to an analytic model that is useful over a wide frequency range and reveals parameters of effective moving mass and total elastic restoration (from blood pressure plus tissue elasticity).

The connection between damping and inertial impedances transcends particular models of vibration geometry and can be described in terms of the fundamental properties of complex analytic functions. (A complex function is defined to be analytic if it has a unique complex derivative.) The 0° component of a real-world impedance function correlates with the real part of an analytic function. The 90° component similarly correlates with the imaginary part. Frequency corresponds to an imaginary argument of the analytic function. The real and imaginary parts of analytic transfer functions are interdependent, and the same interdependence is observed between the 0° and 90° components of real-world impedances. Consequently, in attempting to extrapolate real impedance data to discover the limiting behavior of the 90° component, it is effective to fit both phase components of impedance to a complex analytic function. Such a function fit utilizes more good data than a real-valued function fitted solely to the 90° component of arterial impedance.

Inertial and restoring impedances cancel at a resonant frequency, leaving a pure damping impedance. Artery vibration mode measurements are typically only accurate in the broad vicinity of this resonant frequency. Very far from resonance, excitation of an arterial vibration mode becomes vanishingly small. It is not feasible to measure arterial impedance so far below resonance that the measurement is totally dominated by the pressure-revealing restoring impedance term. Hence, the goal of the frequency-baseline determination is to observe the behavior of arterial impedance at a fixed pressure, over the usable range of measurement frequencies, and to establish a rational analytic function fit to these data. The correct general form of the transfer function has already been defined, to a great extent, by the physical arguments given above concerning the high- and low-frequency limits of effective restoring constant, damping and inertia terms. Using an approximate fit based on a finite number of measurements and a finite number of analytic function coefficients, the low-frequency limit of the curve is established. The accuracy of this fit depends not so much on the numbers of measurements and function-fit terms as on the linearity of the measurements, on the signal-to-noise ratio of measurements (which can be improved by averaging of many measurements), and on the accurate fulfillment of the symmetry conditions demanded in step 2 and described earlier, in relation to the shape and alignment of assembly 1 in FIGS. 1, 2 and 3. It is noted here that substantial parallelism of tissues along the arterial symmetry axis is needed for high accuracy. If arterial vibrations are monitored where a bone or tendon crosses very near the artery at a sharp angle, symmetry will be compromised. Even with total tissue parallelism along the arterial axis, a sharp departure from radial symmetry very near the artery wall (e.g., from a tendon lying very close alongside the artery) will couple significant energy into high-order vibration modes, causing errors in a system of measurements and analysis based on insignificant energy beyond three-lobed mode shapes.

Data Sampling Principles

In the aspect of the invention being described, the driver waveform is made periodic, for computational convenience, and typically carries six harmonic sinusoidal components. For example, an excitation periodicity of 50 Hz with sinusoid components at 50, 100, 150, 200, 300 and 400 Hz is a waveform that, sampled at 1200 Hz, causes each period at each harmonic frequency to be evenly subdivided-3 samples per period at 400 Hz, 4 per period at 300 Hz, etc., which simplifies digital frequency analysis. The driver is therefore excited with such a waveform. Returning data samples are 0.02 seconds each (in this example), giving one sample per complete period at the fundamental frequency. For frequency analysis, however, samples are grouped in threes, i.e., samples 1,2,3 as a group, samples 2,3,4 as a group, samples 3,4,5, etc. The groups obviously overlap. Each group is 0.06 seconds long and contains 72 time samples. These samples are weighted by a symmetric function that is maximum in the middle and tapers to zero at the first and last samples, e.g. a Hanning window, which has the shape of one period of the function $(1+\sin(f^*t))/2$ for time t and angular frequency=$2\text{-}pi^*50/3$ radians per second, giving a 0.06 second period. This windowed sample is then subjected to twelve fourier sums over the 72 weighted samples, six sine sums and six cosine sums, at the six driver frequencies. This yields six frequency component pairs with 90° relative phases. The reasoning behind this digital filtering process is explained, e.g., in the book *Digital Signal Analysis*, published by Bruel and Kjaer Company of Naerum, Denmark, dated August, 1981.

The above is but an example of how time samples can be frequency-analyzed. Alternatively, it is possible to obtain frequency baseline data through use of non-periodic or random signals, or through modulating or switching the frequency of the driver sinusiod over time. Best results are obtained when data at several frequencies can be resolved over a brief enough time period that blood pressure changes negligibly. It is useful to choose, for intensive analysis, time windows from smooth portions of the diastolic blood pressure curve, near the maximum and near the minimum. Once the parameters of the patient-instrument coupling are established through multiple-frequency analysis of a few time-selected data samples, simplified analysis is used for subsequent update computations in pressure tracking over time.

Arterial Vibration Modes

The vibration mode shapes illustrated in FIG. 5 are the lowest terms in an infinite series of shapes that can be used to analyze any arbitrary radial vibrational perturbation in a medium that is radially symmetric and unchanging along the third axis, i.e. the axis perpendicular to the cross-sectional plane of the diagram. For each radial mode illustrated in FIG. 5, there is an analogous tangential mode. Blood pressure interacts directly only with radial components of mode shape, though simulation analysis generally takes account of tangential motions. Tangential vibration components are not observable to the ultrasound system described for this aspect of the invention. Mode shape analysis can be applied, with added complexity, where radial symmetry is broken severely, e.g. where a tendon parallels an artery in close proximity. Since the analysis is two-dimensional, it is valid only where the vibrational perturbation is unchanging along the third axis. In the absence of severe violations of radial symmetry, these vibration modes are substantially orthogonal, meaning that there are amplitude-squared terms for power-dissipation and energy of individual modes, but negligible power or energy associated with products of amplitudes of differing modes. Thus the different modes do not interact significantly, but simply coexist superimposed on each other. Modes can therefore be analyzed separately.

The terms in the cylinder mode shape analysis correspond directly to the terms in a Fourier series for a periodic function. The lowest term in a Fourier series is the zero-frequency term, a constant, corresponding to Mode 0 of FIG. 5. We see that radius is changed by a constant amount, independent of angle, from solid contour 100 to dashed contour 101 (FIG. 5a). Since we are discussing vibrations whose acoustic wavelengths typically exceed arterial dimensions by a factor greater than 100, compressibility effects are negligible. Since Mode 0 represents a net change in cross-section, it can only be observed in the present context of incompressible motions if there is axial vibrational movement, so that cross-section areas change differently at other axial locations. This property is reflected by contours 102 and 103 (FIG. 5b), corresponding to contours 100 and 101 and illustrating the same cylinder viewed from the side. The dashed vertical line indicates where the upper cross-sections are taken. To the extent that the desired vibrational symmetry is maintained, Mode 0 excitation should be negligible. Thus, Mode 0 is not a significant vibration mode in the context of the measurements and computations of the systemic arterial pressure-measuring embodiment of this invention. The tangential Mode 0 is a vibrational rotation, uniform at all angles, and is insignificant in the present context.

Mode 1 is a rigid-body vibration of the cylinder between coutours 104 and 105 (FIG. 5c). An energetically orthogonal component of Mode 1 is illustrated in contours 106 and 107 (FIG. 5d), where the motion is at right angles to the upper illustration. Mode 1 vibrations are not sensitive to blood pressure. The vibrations can be affected by pulsating arterial cross-sectional area, but the effect is very weak since it depends primarily on the small difference between blood density and artery-surround density.

Mode 2 and all higher modes are "shape" modes, sensitive both to blood pressure and arterial wall stiffness. They may be influenced to a lesser extent by stiffness in tissues outside the arterial wall, although this effect is very small. Contours 108 and 109 (FIG. 5e) illustrate one axis of excitation of Mode 2, while contours 110 and 111 (FIG. 5f) illustrate a second axis, displaced by a 45° angle. The modes for the two axes are energetically orthogonal.

Mode 3 has a three-lobed symmetry, with one excitation axis illustrated by contours 112 and 113 (FIG. 5g) and a second axis illustrated by contours 114 and 115 (FIG. 5h). This second, energetically orthogonal vibration axis is displaced from the first axis by 30°.

If the vibration driver is directly above the artery and if tissues are symmetric on the left and right sides of the artery, then the excited vibration axes will be vertical, as in the top-row figures for Modes 1, 2 and 3. This left-right symmetry will be violated, for example, if a vein or tendon parallels the artery nearby and to the left or right of the central vertical axis down from driver/sensor assembly 1 (recalling FIGS. 1-3). The differing axis excitations may not be in the same vibration phase, since the symmetry-perturbing object will have its own vibrational phase response to the applied excitation. Circularly-polarized vibrations are possible, in which the shape perturbation appears to rotate rather than vibrate. This arises from the superposition of excitations along energy-orthogonal mode axes and differing in phase by 90°.

High-order vibration mode shapes are excited only by high-order geometric derivatives of pressure and stress in the medium. If the medium is relatively homogeneous, high-order derivatives attenuate very rapidly with depth below the vibration driver. Hence, for deep arteries in relatively homogeneous surroundings, vibration mode excitations above Mode 2 are negligible. Measurable Mode 3 excitation is achieved in shallow arteries or arteries lying next to an impedance discontinuity. Excitation of Mode 3 in shallow arteries can be reduced by using a relatively wide vibration driver, which generates a "smoother" vibration field. Even with a wide driver, however, Mode 3 excitation in the common carotids arises from the proximity of stiff tendons and larynx cartilage and the soft jugular vein. Carotid vibration mode axes may not line up with the vibration driver, and excitation phases may depend significantly on local surroundings.

Significant excitation of arterial vibrations above Mode 3 is difficult to achieve without direct contact between the vibration driver and the artery. For blood pressure determination, high-order mode excitation is undesirable, since it complicates the analysis and since more than three ultrasound angles across the artery are required to separately distinguish higher modes.

The Single-Mode Network Algorithm

The network algorithm for pure Mode 2 vibration relates pressure-induced changes in vibration measurements at constant frequency to the coupling between vibrator and artery and to mechanical impedance of the artery itself. The algorithm is based on generalized linear network theorems, particularly the Theorem of Reciprocity, which states in effect that energy must be able to pass through a passive linear network or medium between two objects with equal efficiency in either direction. Here, the medium is the tissue between the vibration driver surface and the artery. Because the energy flow takes the form of vibrations of very small amplitude, non-linear fluid and elastic behaviors of the medium are not elicited. In effect, any smooth function (in this case a mechanical stress as a function of the excitatory vibrational velocity field) appears to be linear if only a very short segment of the function is viewed, e.g. here, a very small vibrational velocity and amplitude.

We have seen how vibration-mode analysis is simplified where there is two-dimensional field symmetry in the arterial cross-section plane over the axial length under study, here the length of driver/sensor segment 52 (FIGS. 2 and 3). Symmetry should cause the measured force for segment 52 to correspond to the transmitted force driving an equal length of the artery below. For a constant-width vibration driver, end-effects cause the artery-driving vibration field to weaken moving off-center. To offset this, the ends of the driver are broadened.

We seek to define a two-dimensional force, i.e. force per unit of axial length, exerted on the artery, simplifying the effects of distributed pressure and shear stress into a single number. We use the approach of generalized coordinate analysis, e.g. as explained in Symon, *Mechanics,* ch. 9, Addison Wesley, 1960. The sought-after definition is possible only for a specified vibration mode undergoing a specified motion when force is evaluated. With a defined mode shape, we can use a single length-coordinate to describe motion. For mode shapes like those illustrated in FIG. 5, we describe mode shape changes in terms of changes in length of the radius vector to the cylinder surface along an axis of maximum length-change. If during the vibration cycle we perturb this radius by a very small increment, this perturbation (and the simultaneous radius perturbations at other angles to preserve the mode shape) requires a net increment in work on the vibrating cylinder. The resulting ratio of work increment to length increment defines an effective force for the specified mode shape, according to Eq. 1:

FOR A SPECIFIED MODE SHAPE:

$$F = \text{(work increment)}/\text{(length increment)} \qquad [1]$$

We understand that "F" and "work increment" in Eq. 1 are both quantities per-unit-length in the direction perpendicular to the cross-section of analysis. We can use an analogous force definition in three-dimensional contexts by omitting the implicit "per-unit-length" qualification. Given a principal vibrational axis for a single mode, we use the term "semi-axis length" to describe the radius along that axis, i.e., the length used to define force. For a Mode 2 vibration, assuming that the ultrasound depth measurements are parallel to the principal vibrational axis, the increment in semi-axis length amounts to half the change in ultrasound-measured diameter. For a Mode 1 or a Mode 3 vibration, ultrasound measurements resolved parallel to a principal vibration axis show a constant diameter but a changing average depth of the near and far artery walls (correcting for ultrasound transducer motion). This changing average depth, or common-mode depth signal, is the change in semi-axis length used in the force definition.

If we consider an entire vibrational cycle, we find that the "work-slope" force defined by Eq. 1 describes a sinusoid having an amplitude and phase. Extending from the definition of incremental, instantaneous force, we define vibrational force $F_n$, for Mode n at a specified angular frequency f, as a complex phaser quantity having the amplitude and phase of the instantaneous force signal just defined:

$$F_n = \text{Complex Fourier Component of } F, \text{ Mode } n \qquad [2]$$

For a multi-mode vibration, we describe force as a multi-dimensional quantity extending along as many complex axes as there are excited modes.

Mechanical vibrational impedance (per-unit-length) is defined according to normal engineering practice, as complex vibrational force divided by complex vibrational velocity. This definition is readily extended to mode shapes using definitions 1 and 2, above. (Recall that the amplitude of a complex quotient is the numerator amplitude divided by the denominator amplitude, and the quotient phase is the numerator phase minus the denominator phase. Similarly, the amplitude of a complex product is the product of the amplitudes of the terms, and the product phase is the sum of the phases of the terms.)

These definitions can be used to apply results of discrete network theory to the continuum measurements of this system. With the symmetries, measurements and definitions outlined here, the passive tissue "network" in question can be modeled in the same fashion as a two-port electrical network, such as is described in electrical engineering and physics texts, e.g. Scott, *The Physics of Electricity and Magnetism*, 2nd ed., 1966, John Wiley & Sons, Inc., New York, p. 500. We consider a black box with two connection terminals, 1 and 2. We know only that the box is passive, containing no internal energy sources, and that its responses are linear. Though this box is usually described as an electrical network, the physical principles apply equally to mechanical systems. The electrical-to-mechanical analogy is as follows. There is a known input electrical current analog, here a vibrational velocity V1 (terminal 1, Mode not applicable); a known input voltage analog, here a vibrational force F1 (terminal 1, Mode not applicable); a known output current analog, here velocity-of-change of the arterial semi-axis length, V22 (terminal 2, Mode 2); and an unknown output voltage analog, here the force F22 (terminal 2, Mode 2) driving the vibration mode. These forces and velocities are related by simultaneous equations 3 and 4, with four velocity-impedance coefficients. (In electrical networks, these are usually stated as admittance coefficients, although the equations are easily rewritten in equivalent form using impedance coefficients.)

$$V1 \cdot Z1 + V22 \cdot Zt2 = F1 \quad [3]$$

$$V1 \cdot Zt2 + V22 \cdot Z22 = F22 \quad [4]$$

The Theorem of Reciprocity proves that two of these Z-coefficients are equal. They are both designated Zt2, for transfer impedance, Mode 2. Zt2 and the input and output impedance Z1 and Z22 are unknowns to be determined. Observe that the total "surface mechanical impedance" experienced by the vibration driver is the complex ratio F1/V1, not to be confused with Z1 of Eq. 3. The measured surface mechanical impedance is influenced by arterial velocity V22 via transfer impedance Zt2.

We designate a further arterial impedance, Za2, attributed to the vibrating pressurized blood inside the artery. The force F22 is exerted entirely to overcome impedance Za2 and excite velocity V22 in the cylinder of blood. There is no active source of vibration in the artery to affect the measurements. (Noise from blood flow is present, but is uncorrelated with the vibration driver sinusoid, and thus causes no average error in the demodulated vibration signals.) Hence, we may represent F22 as $-V22 \cdot Za2$. The minus sign arises from the defined direction of F22 relative to V22. We may thus rewrite Eq. 4 as Eq. 5, in terms of the combined tissue-plus-artery impedance, (Z22+Za2), reducing by one the number of complex unknowns.

$$V1 \cdot Zt2 + V22 \cdot (Z22 + Za2) = 0 \quad [5]$$

If blood pressure changes, this alters the sum (Z22+Za2). Designating the altered values at the new blood pressure with an apostrophe ('), for prime, then we obtain a second set of measurements represented in Eqs. 6 and 7, where V1', F1', and V22' are measured and the Z-coefficients are presumed to be unchanged.

$$V1' \cdot Z1 + V22' \cdot Zt2 = F1' \quad [6]$$

$$V1' \cdot Zt2 + V22' \cdot (Z22 + Za2)' = 0 \quad [7]$$

Eqs. 3 and 6 can now be solved simultaneously, yielding Z1 and Zt2. Substitution into Eq. 5 yields (Z22+Za2), and into Eq. 7 yields (Z22+Za2)'. In Eq. 4, the force F22, representing $-V22 \cdot Za2$, is still unknown, as is Z22.

This solution relies on a change in pressure that alters the vibration measurements to an extent resolvable to useful accuracy. The pressure change need not be known. The system reveals its properties when blood pressure varies, because the phase and amplitude of arterial vibrational motion are altered, and because the effect of this alteration on driver velocity and on driver force is measured, revealing the precise effect of the coupling between the vibration driver and the artery.

To illustrate the parallax increment argument given above, subtraction of Eq. 3 from Eq. 6 yields an equation with the increment terms $V1'-V1$, $V22'-V22$, and $F1'-F1$. Solving simultaneously with Eq. 3 yields the same result as solution of Eqs. 3 and 6 directly. The vibrational change induced by blood pressure can be regarded as an independent vibration signal, generated within the artery, measured by the ultrasound system, and felt as the effects propagate to the surface sensors. Combining the data on this parallax signal with the Eq. 3 data on the baseline signal yields the critical transfer-impedance coefficient, Zt2, permitting subsequent solution for the inaccessible impedances (Z22+Za2) and (Z22+Za2)'.

For simplicity, the geometry of the system has been implicitly presumed constant through the change in blood pressure. Arterial radius is different at different pressures most of the time, but not at every instant. The most accurate analysis relies on extracting data sets for which equal radii are observed at differing pressures, as evidenced by differing vibration measurements. Pulmonary artery radius waveforms have been observed to lag behind corresponding internal pressure waveforms, apparently because of visco-elastic behavior of the arterial wall. In peripheral arteries, averaging over several heartbeats, radius has been observed to correlate better with average flow rate than with average pressure, apparently because of active regulation of the smooth sphincter muscles in the artery walls. Whatever the cause of poor pressure/radius correlation, the phenomenon is useful for the current invention because it allows the system to obtain matched-radius data pairs with pressure separation. The network algorithm can then be applied without correction for differing geometry.

In situations where the data fail to yield useful pressure separation for equal-radius data points, the network algorithm must be corrected for change in artery radius, or else the network algorithm must be solved in conjunction with a simulation algorithm, in which case the data in the network algorithm are corrected to a constant radius outside the artery wall. The two approaches are outlined briefly.

The single-mode solution just illustrated is based on unchanging values for driver self-impedance, Z1, and driver-artery transfer-impedance, Zt2. The combined artery-plus-surround self-impedance, Z22+Za2, is affected by changes in both pressure and radius, but for the moment, the two sources of change need not be distinguished. Z1 is substantially unaffected by arterial radius change. This leaves Zt2, which is significantly altered by radius change. Where the data for Eqs. 6 and 7 are for a different radius than for Eqs. 3 and 5, it is necessary to rewrite Zt2 to analyze radius-change sensitivity.

An expression is derived for the complex ratio Zt2'/Zt2, where Zt2 applies to Eqs. 3 and 5, and Zt2' applies to radius-altered Eqs. 6 and 7. This expression permits solution of the network algorithm where there is radius change. This ratio is determined iteratively, proceeding from an estimated Zt2'/Zt2 ratio to solve the network algorithm, then using the approximate network results to improve the estimate of Zt2'/Zt2, then using this ratio to re-solve the network algorithm, etc. Zt2=2·Vt2·Z22, approximately. Here, "Vt2" represents the velocity transfer coefficient for Mode 2. To understand the physical significance of Vt2, imagine that the artery has been removed and replaced by a uniform tissue whose mechanical properties match the average properties of tissues immediately surrounding the artery. Under these conditions, Za2=Z22, and Vt2=V22/V1. The vibration field in the vicinity of an organ or artery can usually be approximated as a potential field under this hypothetical condition of tissue uniformity. For a two-dimensional potential field, it is easily shown that Vt2 varies linearly with radius, r (or more generally, Vtn varies as $r^{n-1}$). Assuming that the effects of tissue elastic modulus are small (a good approximation at the frequencies used to probe a systemic artery), the phase angle of Vt2 is a simple function of the phase angle of Z1, and the magnitude of Vt2 equals radius multiplied by a function of artery center-depth. The real part of Z22 varies in proportion to $r^2$, while the imaginary part varies as a power law of r that is a function of the phase angle of Z22. A Z22 phase angle approaching zero implies a zero-power law, $r^0$, while a phase angle approaching +90° implies a first-power law, $r^1$. The two functions of phase angle just described are derivable using simulation algorithm techniques. With the approach shown here, it is possible to solve the network algorithm for measurements at different radii. Solution at a number of frequencies reveals the frequency dependence of Z1, Zt2 and (Z22+Za2). This information can be used in more sophisticated corrections for arterial radius, in a procedure where network solutions are improved iteratively, based on simulation algorithm evaluation of the frequency dependences of network parameters.

The other approach is to solve the network algorithm not in relation to raw data, but in relation to simulated data based on raw data and a simulation algorithm whose parameters are adjusted iteratively to fit actual measurements. It is noted that the simulation applies only to the artery and its immediate surround, in a context of radial symmetry. The network algorithm links this relatively simple simulation to the much more complicated geometry linking the vibration driver to the artery. In the simulation, a radius is chosen outside the artery wall in a hypothetical uniform surround-medium of the artery. The simulated artery is driven, mathematically, to match the vibrational mode velocity observed by ultrasound at a given frequency. The vibration velocity at the computational reference radius is then solved, in relation to the simulation. This computed velocity is used for V22 in the network algorithm. For a second blood pressure, ultrasound data indicate an altered artery radius and altered mode vibrations. The simulation is adjusted to the new artery radius and driven to match the altered mode vibrations observed, and the vibrational velocity is again computed for the fixed computational reference radius. This gives a new parameter, V22', which is used to complete the network solution. Other relevant modes are treated in similar fashion, possibly in an expanded version of the network algorithm. Network solutions at various frequencies yield values for the sum (Z22+Za2), which apply now not to the actual artery but to the hypothetical vibrating cylinder of fixed reference radius, containing the changing artery. The simulation model implies another set of values of (Z22+Za2), for the two artery pressure and radius conditions and at the frequencies of analysis. The differences between the network solutions and the simulation values for (Z22+Za2) constitute an error vector. The goal of the simulation algorithm is to drive all the components of this error vector to zero, simultaneously, by adjusting variable parameters of the simulation model. The simulation must be tied to other observables. For example, the elasticity parameters of the simulated wall must be consistent not only with vibration data, but also with the observed short-term changes in artery radius with changes in computed pressure.

It can be shown that the mechanical impedance associated with blood pressure as it restores an artery to roundness in a particular vibration mode shape is directly proportional to blood pressure, inversely proportional to frequency, and independent of arterial diameter, tissue properties, etc. As shown in Eq. 8, pressure impedance Zpn for vibration Mode n is imaginary, containing the imaginary unit "j" in the denominator, multiplied by angular frequency "f" in radians/second.

$$Zpn = (n^2 - 1) \cdot pi \cdot P/j \cdot f \quad \text{for } n > 0 \qquad [8]$$

The Mode n=2 and n=3 cases are especially important:

$$Zp2 = 3 \cdot pi \cdot P/j \cdot f \qquad [9]$$

$$Zp3 = 8 \cdot pi \cdot P/j \cdot f \qquad [10]$$

Where a relatively pure Mode n=2 vibration is obtained and analyzed by the network algorithm for constant radius r and frequency f, then changes in impedance (Z22+Za2) are simply the changes in Zp2. Hence, we can solve for changes in pressure P. When the vibrations are analyzed for differing radii as well as differing pressures, then a complete simulation result is needed to determine both pressure change and absolute pressure.

Wall Stiffness Impedance

Arterial wall stiffness causes a velocity impedance having a similar form to Eq. 8, but independent of pressure and having a fourth-power dependence on Mode number n. If arterial wall thickness is approximated as constant during the course of a vibration cycle, then Eq. 11 describes the mechanical impedance Zwn due to wall stiffness.

$$Zwn = \text{const.} \cdot (n^4/j \cdot f) \qquad [11]$$

For the important Mode n=2 and n=3 cases, we write:

$$Zw2 = \text{const.} \cdot (16/j \cdot f) \qquad [12]$$

$$Zw3 = \text{const.} \cdot (81/j \cdot f) \qquad [13]$$

$$(Zw3/Zw2)/(Zp3/Zp2) = (81/16)/(8/3) = 1.8984. \qquad [14]$$

Eq. 14 expresses the important difference in proportions between wall stiffness impedance and pressure impedance for Modes 2 and 3. When net effective pressure is computed, separately, for the two modes, the difference in results will represent 0.8984 times the Mode 2 wall stiffness pressure.

The approximation that artery wall thickness does not vary at the vibration frequency, as needed for Eqs. 11-14, is valid if the thickness of the arterial wall is not too large a fraction of radius and if the wall material is much stiffer than adjacent tissue. Under these conditions, the "thin" wall can be bent significantly, but the relatively weak tangential shear forces from adjacent tissues will not cause significant tangential stretch displacements. If the wall is healthy and compliant, there may be significant tangential stretch displacements, but in that case, stiffness impedance Zw is small and unimportant.

These arguments apply approximately for constant arterial radius. When radius changes, stiffness parameters must be adjusted for changing artery size and wall thickness. This is best dealt with in a comprehensive simulation model.

Absolute Pressure From A Simplified Simulation

To solve mathematically for absolute blood pressure, we must determine the detailed makeup of the term (Z22+Za2). To a first approximation, the imaginary part of (Z22+Za2) is composed partly of the restoring impedance (Zp2+Zw2), and partly of an inertial impedance dependent on the mode shape, the arterial diameter and the average density of blood and surrounding tissues.

There are several ways to evaluate the inertial impedance and extract approximations of blood pressure. One way, as previewed earlier, is to fit a rational analytic function to the measured data and extract the coefficient corresponding to pressure. This approach is quite abstract. What is needed are simple models that indicate the kind of signal to expect and how to design equipment to receive such a signal. This and more sophisticated models tied to the details or arterial structure become valuable in the broadened context where we wish not only to find blood pressure, but to interpret measured impedance data and gain information on the behavior or the artery itself. This kind of question becomes central in the whole-organ embodiment, where evaluation of tissue responses is a primary goal.

From potential flow theory, applying the force definitions of Eqs. 1 and 2, it can be shown that Eq. 15 gives non-viscous inertial mass impedance Zm, as a function of frequency f (multiplied by the imaginary unit j), average density ρ, artery radius a, and Mode number n:

$$Zm = j \cdot f \cdot \rho \cdot 2 \cdot pi \cdot a^2 / n \qquad [15]$$

Zm is an impedance per-unit-length. Half of Zm is attributed to exterior moving mass (e.g. a part of Z22 in the Mode 2 case), and the remaining half is attributed to interior moving mass (e.g. a part of Za2 in the Mode 2 case). Notice the special n=1 case of rigid cylinder motion. In this case, halving Zm, we recognize the formula for mass per-unit-length of a cylinder, multiplied by the ratio of acceleration to velocity, j·f. The other half of Zm is attributed to surrounding fluid. For higher n, the inertia decreases as the field of motion becomes increasingly localized to the immediate vicinity of the vibrating cylinder surface.

Combining Eq. 15 with Eq. 8 gives the Mode n resonant frequency, frn, where pressure and inertial impedances cancel, leaving only a damping impedance. We can expect the imaginary part of the network impedance term (Z2n+Zan) to pass through zero in the vicinity of frn:

$$frn = (SORT(n(n^2-1)P/2\rho))/r \quad \text{forn} > 1 \qquad [16]$$

The mode n=2 and n=3 cases are the most useful:

$$fr2 = (SORT(3P/\rho))/r \qquad [17]$$

$$fr3 = 2(SORT(3P/\rho))/r \qquad [18]$$

To correlate these formulas with a real artery, set r to the estimated radius in the artery wall where pressure has fallen halfway from internal blood pressure to ambient pressure. To obtain an effective weighted-average density, ρ, weight estimated arterial wall density by n multiplied by (wall-thickness/radius), and for the remainder of the average give equal weightings to estimated blood density and surrounding tissue density. Thus, if wall thickness is 9% of r, then effective average density for n=2 is 2×9%=18% of wall tissue density, plus 41%, each, of blood density and surrounding tissue density, to give a 100% total weighting. For n=3, the weighting factors become 27%, 36.5% and 36.5%. Note that the three densities entering the weighted average will not differ greatly unless calcification has increased wall density, or unless the material around the artery is very fatty and therefore less dense. A better corrected-density estimate, still based on the simplifying assumption of non-viscous fluid flow, takes into account the effective thickness over which blood pressure drop takes place.

The vicinity of fr2 provides the greatest sensitivity of vibration measurements to pressure change. For normal blood pressure and typical carotid artery dimensions, the radian-frequency fr2 translates to about 300 Hz. Because the resonant quality factor, or Q-factor, of arterial vibrations is typically less than 1.0, the usable Mode 2 measurement frequency region typically extends from 50 to 600 Hz. Since resonant frequency varies only as the square root of blood pressure, good signals can be obtained continuously at around 300 Hz without varying frequency over time to track changing frequency fr2.

The most sensitive data on Mode 3 vibrations are obtained at fr3, which is twice as high as fr2 in Eq. 17, and possibly more than twice as high when the large Mode 3 contribution to P from wall stiffness is considered.

Analytic Function Fit Algorithm

The most recent analysis provides a sense of the nature and magnitudes of the significant terms in arterial vibration dynamics. A general equation for the impedance associated with vibration Mode n expresses this understanding:

$$Zn = (n^2-1) \cdot pi \cdot P/j \cdot f + D(f) + j \cdot f \cdot M(f) \qquad [19]$$

For n=2, Z2 corresponds to (Z22+Za2) of network algorithm Eq. 5, or to the corresponding primed quantity of Eq. 7. Where an artery is shallow enough to obtain good Mode 3 excitation, and where the three-angle ultrasound system resolves the modes, Z3 may also be determined by a network algorithm. Hence, we analyze the frequency-dependence of Zn, normally for n=2 or 3, deriving data on Zn from multiple applications of a network algorithm using both pressure-baseline and frequency-baseline data. From this analysis, we distinguish the effect of pressure from other overlapping effects.

It is realized that a wall stiffness error may reside in the term, P. The damping and mass terms, D and M, are functions of frequency f. From Eq. 15, we know that $M(f)$ approaches $(\rho \cdot 2 \cdot pi \cdot a^2/n)$ in the high-frequency limit, where viscous shear ceases to entrain extra mass. M is greater than this high-frequency value as f approaches 0. $D(f)$ goes in the opposite direction, from a low-frequency minimum where viscous and shear forces control the flow pattern and prevent steep shear velocity gradients, up to a high-frequency maximum where shear gradients are quite steep, being confined to the arterial wall thickness over which pressure drops from blood pressure to ambient pressure. Define Mode n resonant frequency, frn, as the frequency where complex impedance Zn is real-valued. The relationship of frn to P is shown in Eq. 20:

$$(n^2-1) \cdot pi \cdot P = frn^2 \cdot IM(dZn/df) \cdot (2 + d(\ln(M))/d(\ln(f))) \quad [20]$$

Pressure P is nearly computable from known data, given the tools of network analysis. Where Mode n=2 is dominant, we can easily measure zero-phase frequency frn, here fr2. In the vicinity of fr2, we can evaluate the imaginary part, IM, of the frequency slope of impedance Zn. Relatively simple simulation models tell us how the log-log slope, $d(\ln(M))/d(\ln(f))$, typically varies as a function of the non-dimensional quality factor, Q, defined by Eq. 21:

$$Q = fr2 \cdot IM(dZ2/df)/Z2 \quad [21]$$

At resonant frequency fr2, denominator Z2 is real by definition. If D and M were constants, defining a simple second-order system, then Eq. 21 would give the actual resonant quality factor Q, and the log-log slope of Eq. 20 would be zero. For the more complex viscous flow problem being considered here, absolute pressure can be computed from Eqs. 20 and 21 plus an empirical expression for the log-log slope of Eq. 20 as a function of Q. This empirical function is derivable from computer simulation studies, with possible refinement based on animal studies and clinical studies of patients who require arterial catheterization.

Eqs. 22–24 provide a basis for a function-fit approach to determine pressure P, using more computation time but achieving better accuracy:

$$Zn = \frac{A0 + A1 \cdot S + A2 \cdot S^2 + \ldots + Am \cdot S^n + Am+1 \cdot S^{n+1}}{S + B2 \cdot S^2 + \ldots + Bm \cdot S^n} \quad [22]$$

$$A0 = (n^2-1) \cdot pi \cdot P \quad [23]$$

$$s = j \cdot f \quad [24]$$

As Eq. 24 suggests, the measured complex function Zn of the imaginary argument $j \cdot f$ can be expressed as a part of the encompassing complex function Zn of the arbitrary complex variables, i.e., as part of Zn(s). As long as Zn arises from a casual linear network ("casual" networks are mathematically defined as responsive only to past and present input, and not to inputs that have not yet arrived), this extension to a complex function is valid and, for most applications of importance to this invention, uniquely defined. Furthermore, Zn(s) is an analytic function, i.e. it has a unique complex derivative and desirable extrapolation properties. Both the real and imaginary parts of the measured responses bear on the extrapolation of the imaginary part of the function towards zero frequency, to determine pressure-dominated response in a frequency range where measurement accuracy deteriorates. For insight into the connection between imaginary parts and real parts of measured, causal response functions, both in the time and frequency domains, see "The Hilbert Transform", by N. Thrane, Ph.D., in *Technical Review* No. 3-1984 by Bruel and Kjaer Instruments, Inc., 185 Forest Street, Marlborough, MA 01752.

A useful form for an analytic function that can be fitted to a finite number of empirical data points is the ratio of two complex polynomials. The polynomial coefficients must be real numbers, since non-zero imaginary parts of the coefficients would lead to assymmetry of Zn for positive and negative frequencies, unlike real-world impedances. Finally, the expression should fit the behavior of Eq. 19, where the real-valued functions $D(f)$ and $M(f)$ approach finite limits as frequency f goes to zero and to infinity. This is accomplished by starting the denominator polynomial with a first-order term in s and terminating it at order m, while extending the order of the numerator by one at either end, from a zero order starting term to an m+1 order final term. These criteria are all incorporated into Eq. 22. The first-order denominator coefficient "B1" can always be simplified to "1" by dividing the value of B1 through both the numerator and denominator coefficients.

Clearly, coefficients A0, A1 and A2 of Eq. 22 correspond to the low-frequency limit values $(n^2-1) \cdot pi \cdot P$, D(0) and F(0). In the high-frequency limit, where the highest-order terms dominate, the pressure-related, damping and mass terms of Eq. 19 correspond to Am−1/Bm, Am/Bm and Am+1/Bm, respectively. The Am−1/Bm ratio is not reliably correlated with real pressure or stiffness, however, since pressure and stiffness effects are swamped in the high-frequency data by damping and inertial effects. Physical significance may be attributed to the high-frequency damping and mass terms of the polynomial expression. By comparing the empirical mass term, Am+1/Bm, with the value derived for Eq. 15 using the effective radius and density procedures described, it is possible to seek density anomalies due, for example, to artery wall calcification. Recall that Eq. 15 is valid in a high-frequency limit, where damping forces cease to perturb vibrational geometry. The high-frequency damping coefficient, Am/Bm, may carry physical significance, although it may not accurately reflect the infinite-frequency limit behavior of the artery, depending on the quality and frequency range of the data.

The Ai and Bi coefficients are real values to be determined from data. Multiplying through by the denominator of Eq. 22 and collecting terms gives:

$$\sum_{i=0}^{m+1} (Ai \cdot s^i) - \sum_{i=2}^{m} (Bi \cdot s^i \cdot Zn) = s \cdot Zn \quad [25]$$

Eq. 25 splits into two real-number equations if the real and imaginary parts are equated separately. Both equations are linear in Ai and Bi and are defined completely by one impedance Zn at one frequency, i.e., one s. Determinations of Zn at m+1 separate frequencies and a fixed pressure give 2m+2 equations to solve for the combined total of 2m+1 Ai and Bi coefficients. One excess equation may be dropped. Additional frequency determination of Zn permit a least-squares regression to obtain a statistically better fit for a given order, m. Once we have solved for coefficient A0, we can solve for pressure P using Eq. 23.

Setting m too high in Eqs. 22 and 25 is likely to cause increased function-fit errors, because the fitted function follows noise in the data. Using a given set of Zn versus s data and least-squares regressions, we start with a small m and determine pressure for successively higher m. Computed pressure will first settle with decreasing steps toward an apparent limit, but will then show increasing fluctuations as m becomes too high. A value of m is found for routine machine computations such that computed pressure is minimally sensitive to m.

Pressure could also be determined from a data fit by using a generalized simulation model for an artery, with undetermined physical parameters for stiffnesses viscosities, densities, radii and even possible coupling terms for nearby disturbing influences, e.g. tendons. The simulation approach is probably best for dealing with changing artery radius. The more abstract approach just shown is computationally simpler and is often useful.

Three-Axis Ultrasound Interpretation

The analysis shown so far is valid only to the extent that vibration-mode principal axes all lie parallel to an ultrasound axis, as with the single-axis variation of this systemic arterial pressure embodiment. If this symmetry criterion is met, then three-axis ultrasound measurements suffice to determine the separate Mode 1, Mode 2 and Mode 3 vibrational excitations. With these data, the two-mode network algorithm can be solved separately. Then, the analytic function fit algorithm need only be solved once for an absolute pressure.

If single-axis vibration symmetry is not assumed (the assumption is often inaccurate), then the network and simulation algorithms must be solved simultaneously, iteratively, even with three-axis ultrasound data.

To understand the data requirements for resolving simultaneously-excited vibration modes, consider Mode 1 for single-frequency excitation. Mode 1 is a simple translational motion in two dimensions. Whenever single-frequency sinusoidal motions along different axes in a plane are superimposed, the resulting trace is an ellipse (including the special cases of a circle and a line segment, which is a degenerate ellipse). To specify all the parameters of the trace, begin by specifying the two components of the major axis vector. Resolving the component of sinusoidal trace motion along the major axis, the third parameter is the phase of this major-axis sinusoid relative to a specified reference phase (e.g., vibration driver velocity V1). Rotating in space $+90°$ from the major-axis vector, the minor-axis amplitude is described as the fourth parameter. This amplitude is positive for counter-clockwise rotation, or otherwise negative. By choosing to measure along the major and minor axes, the phase of trace motion resolved along the minor axis is constrained to differ from the major-axis phase by 90°. Hence, four parameters completely specify the vibrational motion.

For single-frequency excitation of a higher-order shape mode, four parameters are again sufficient. Recalling the descriptions of Modes 2 and 3 in conjunction with FIG. 5, it is seen that two energetically-orthogonal shapes are separated by principal axis rotations of 45° for Mode 2 and 30° for Mode 3.

The three-axis ultrasound system resolves three common-mode and three differential-mode vibrational velocities. Each resolved velocity has 0° and 90° phase components. The resulting six differential-mode components are more than sufficient to determine the four parameters of the differential Mode 2 vibration. The six common-mode components are insufficient to determine the eight parameters needed to determine both Modes 1 and 3. To help resolve the uncertainty, Mode 1 excitation is not significantly affected by either pressure or radius changes in the artery, while pressure and radius sensitivities of higher modes have been described. This is useful for determining the Mode 3 velocity transfer ratio parameter, Vt3, which in this context is a four-parameter quantity, like the vibration modes, involving two energetically-orthogonal versions of the Mode 3 shape. Common-mode vibration changes directly reveal the major-axis direction and major/minor axis amplitude ratio for Vt3. Final resolution of the network algorithm uncertainty uses simultaneous solution of the network algorithm with the analytic function fit algorithm. The detailed solution process follows directly from the principles and procedures already described.

Electronic Signal Acquisition

The functions of the vibration drivers and sensing transducers of assembly 1 (FIGS. 1–3) have been described. We now described how electronic signals are processed in driver/sensor assembly 1 and after they pass via cable 2 between assembly 1 and computer/controller 3.

Electronic acquisition of low frequency data for pressure computation is diagrammed in FIG. 6. FIGS. 7, 8, 9 and 10 describe how ultrasound data are processed to generate the outputs of modules 150 and 151, which give three ultrasound diameters and three rates-of-change of diameter (150) and three depths and three rates-of-change of depth (151). At the center of all data gathering and processing is the Central Processing Unit, CPU module 152 (not to be confused with overall computer module 3 of FIG. 1, which encompasses CPU 152 and nearly all electronics not in the driver-sensor or video display units). The CPU interchanges digital data and addresses with a Low Frequency Analog/Digital-/Analog acquisition system. LF A/D/A module 153, via bidirectional data bus 172 and address bus 173 generally carrying data unidirectionally from 152 to 153. If CPU module 152 is e.g. an IBM PC-XT computer, then an appropriate LF A/D/A module is e.g. the Lab Master system from Scientific Solutions, Inc., Solon, OH. Module 153 needs to receive low-frequency analog data from several wires, sample it, digitize it, and make the data available to the CPU. The module also needs to receive digital data from the CPU, convert it to an analog signal (e.g. a voltage) and provide that signal as an output. To simplify software development and avoid timing problems, it helps if module 153 contains an independent clock and sequencing circuitry, so that analog input sampling and output value updating can follow a steady rhythm despite variations in main-computer processing speeds. Buffers and interrupts between modules 152 and 153 are used for managing data transfer.

A low frequency drive signal travels from 153 to low frequency power amplifier 154, whose output goes to interconnected vibration driver cores 59 and 61 ( FIG. 2), represented schematically here (in FIG. 6) by a single module, 155. The drive signal is a digitally-generated periodic waveform carrying the drive frequencies to be analyzed in the vibration data inputs returning to 153. Related to the drive output, two driver force signals and a driver velocity signal come back into 153, in addition to six ultrasound dimension signals and six corresponding rate-of-change signals. Each of arrows 175, 176, 177 and 178, carrying the respective diameter, diameter-change, depth and depth-change signals from the ultrasound assemblies to LF A/D/A module 153, represents three wires, one wire for out-and-back echo data for transducer assembly 62 (FIGS. 2 and 3), the second wire similarly for transducer assembly 65, and the third wire for transverse echo data, for combined 62-to-65 and 65-to-62 transverse echoes. The velocity signal is derived when piezoelectric ceramic accelerometer assembly 156, comprising strain gauge 55, post 57 and mass 56 of FIG. 2, gives a signal to charge amplifier 157 (contained physically in mass 56) and the resulting acceleration signal is AC-integrated by 158 to give velocity. AC integrators 158 and 159 give near-exact signal integration at the audio frequencies of interest, but include very-low-frequency AC coupling and DC feedback to reduce gain to zero at zero frequency, so that the integrator outputs give near-zero average output signals over long intervals. The total force signal represents the output generated when piezoelectric force transducer assembly 160, comprising strain gauge 53 and post 54 of FIG. 2, is coupled to charge amplifier 161 (contained physically in mass 56).

The remaining circuitry is devoted to generating the residual force signal. The force-transducer load approximates a series mass-spring-damper combination. Changes in blood pressure beneath the transducer produce small variations in the mechanical impedance loading the force transducer, causing small changes in the net force readings, from a few precent down to a small fraction of a percent of variation. To digitize the force variation data to high resolution, the system simulates the force of a mass-spring-damper series responding to the measured transducer velocity signal and substracts this simulated force signal from the measured net force signal to give the residual force signal. The mass-spring-damper parameters are adjusted to minimize the maximum residual force signal over the frequencies of the driver. High amplification and high-resolution digital conversion of the residual signal is then possible. Before the simulated mass-spring-damper parameters are adjusted for a small residual, overload of various equipment is avoided by reducing the amplitude of the low frequency drive signal from 153 to amp 154. Drive signal amplitude is then raised as a balance is achieved, by rewriting the function-generator memory that gives the audio output cycle with larger-magnitude waveform data.

The simulated mass-spring-damper force is a weighted sum of the acceleration, velocity and position signals of the driver. The acceleration signal from charge amp 157 is AC-integrated by 158 to give the driver velocity signal, as discussed, and this velocity signal is AC-integrated by 159 to give the driver position signal, valid over the spectrum of the low frequency drive signal. The acceleration, velocity and position signals are given variable amplification, respectively, by multiplying digital to analog converters 163, 164 and 165, which are typically field effect transistor devices accepting the acceleration, velocity and position signals at their reference inputs, providing gain control via digital inputs, and providing buffered analog outputs representing the analog inputs multiplied by the digital gain control inputs. The respective gain-control inputs are provided by the outputs of digital latches 166, 167 and 168, which are addressed from CPU module 152 via bus 170 and loaded with data via bus 171. Summing amplifier 162 adds the three multiplying D to A outputs and the total force signal from amp 161 together, with appropriate polarities of gain to give a small residual signal as the sum.

The functioning of the ultrasound system, ultimately making possible the outputs of modules 150 and 151 tracking appropriately-identified arterial boundaries is described with respect to FIGS. 7–10. In FIG. 7, computer module 152 controls counter 180, e.g. a 10 bit synchronous counter, via control bus 181. The counter includes an independent clock which can be turned on and off by 152 and which drives the counter to cycle continuously through its full count sequence and back to zero, once for each complete ultrasound cycle. For the complete two-transducer, three-axis ultrasound system, a complete ultrasound cycle includes a pulse transmission by transducer assembly 62 (FIGS. 2 and 3), a receive period for both transducer assemblies 62 and 65 (FIG. 3), a quiescent period for ultrasound echoes to die down, a pulse transmission by transducer assembly 65, a second receive period for 62 and 65, and a second quiescent period completing the cycle. Following the first pulse transmission, assembly 62 receives echoes from the pulse it transmitted while assembly 65 receives a transverse echo of the same pulse output, and similarly following the second pulse transmission, but with the out-back and transverse echo receivers reversed. The two transverse echoes are treated interchangeably since they are nearly identical, and a single ultrasound receiver amp and set of tracking circuits process the alternating transverse echo signals as if they were from a single transducer of doubled rep-rate relative to the overall ultrasound rep rate. Appropriate switching circuitry is provided for the sequencing of pulse transmissions and receptions just described.

FIGS. 7 and 8 describe only ultrasound depth and diameter acquisition for a single path, while FIGS. 9 and 10 show tracking only of ultrasound depth. Ways of expanding on these descriptions to include the three paths and diameter as well as depth can readily be worked out by those skilled in electronics.

The output of counter 180 sequences memory addresses via bus 182. That memory, at 183, is divided into sequence-control bits and data bits relating to analog output and input information. As diagrammed, 1024 words of 8 bits are devoted to analog data, while 1024 words of 4 bits are devoted to sequence-control. Of the four bits, only three are used for the functions being described, although a complete three-axis ultrasound data acquisition system will require the remaining data line and additional lines as well. For writing to or reading from memory 183, computer 152 stops the clock sequencing the counter in 180 and accesses the memory via interface logic module 195, which is connected to computer 152 via a bidirectional data bus and an address bus from the computer. Another bidirectional data bus connects 195 to memory 183, while an address bus goes from 195 to 183.

The four control bits of 183 are coupled via bus 185 to 4-bit latch 186, whose outputs 187, 188, 189 and 190 are labeled, respectively, send/receive, preset1, preset2 and unused. The send/receive output controls the state of switches that select for transmitting an ultrasound pulse of receiving an echo. The preset1 bit provides a waveform for initializing the depth tracking circuitry for the near artery wall to a selected depth before releasing the circuitry to lock onto and track a nearby waveform zero-crossing. Preset1 also controls integrator initialization and sample&hold operating modes, as is shown later. The preset2 bit provides a similar initialization waveform for capturing an echo of the far artery wall, and carries similar control information to preset 1. The unused output finds application for three-path ultrasound electronics, and in fact, more control memory and latching is required.

The low addresses in memory 183 are loaded with a digitized ultrasound pulse waveform for transmission. During transmit time, the memory is read sequentially into latch 196 via bus 197, and the latched bits are coupled to D to A converter 198 via bus 199. The output of 198 is an analog waveform which is applied to ultrasound driver amplifier 200, which also functions as a lowpass filter and whose output through wire 206 drives the ultrasound transducer selected for output. When send/receive line 187 goes low, the transmit signal is isolated from the transducers and a received ultrasound signal comes back into flash A to D converter 201 via wire 211. The digitized output of 201 travels via bus 202 to latch 203, which buffers the data for coupling via bus 204 back into memory 183, which is written with the data. For loading received-waveform data back into computer 152, it is necessary in the design being shown (but not with feasible alternative aspects of the invention) to arrest the ultrasound sequencing temporarily while transferring memory address control from clock-counter 180 to interface logic module 195. In this way, a sampled echo waveform may be displayed on video display monitor 6 (also in FIG. 1). However, once desired waveform features have been selected and locked onto for tracking, direct digital acquisition of the received ultrasound signal by computer 152 is not needed, and waveform tracking may proceed uninterrupted. The ongoing ultrasound data needed by the system is preprocessed to yield low frequency analog signals for digital acquisition as shown in FIG. 6 and in more detail in FIGS. 8, 9 and 10. Note that oscilloscope display 4 (FIG. 1), which provides ultrasound waveform monitoring without interrupting digital data acquisition, is not absolutely necessary to system utilization, if the operator is willing to make use of occasional digitized waveform displays while the tracking function is interrupted.

The ultrasound tracking function is described in more detail in relation to FIG. 8. The transmit signal from D/A module 198 via buffer amplifier 200 and wire 206 enters electronic switch 210, which is closed when the send/receive control input on wire 187 is high and open when 187 is low. The waveform is coupled to a selected transducer via wire 211 and switching electronics not shown. Wire 211 also goes to a second electronic switch, 212, which is also controlled by send-receive wire 187 and configured to close when 187 is high (i.e. when switch 210 is open) and to open when 187 is low (i.e. when switch 210 is closed). When 212 is closed, the ultrasound signal couples from wire 211 to wire 220 and to gain module 213, a low-noise wideband preamplifier. The signal subsequently travels to matching filer 214, whose bandwidth matches or is slightly greater than the bandwidth of the ulrasound transducer system, so that unnecessary broadband noise is suppressed with a minimum sacrifice of overall bandwidth. The filter output goes to gain module 215, whose gain is selected to give a desired strength to the ultrasound signal for input to phase-shifter 210. 210 consists of a pair of filter networks and two signal inverters. The filter networks are designed to give complementary outputs differing in phase by nearly 90° over the ultrasound frequency passband. One of these outputs is called the 0° reference, on output wire 211, while the other output has 90° relative phase, on wire 212. The two inverters flip the 0° output to give 180° on wire 213, and flip the 90° output to give 270° on wire 214. The 0° reference signal on 211 couples back into flash A/D converter 201 (FIG. 7) for digitization, computer acquisition and subsequent display, initialization and compensation functions. The four phase signals are coupled to dual 4 to 1 multiplexer 224, which selects one of the four phase inputs for buffered output on wire 221 and one of the same four inputs for buffered output on wire 222. The outputs on 221 and 222 may be the same or differing phases, as determined by computer control of the multiplexer. Phase output 222 is coupled to depth tracker 225, which is one of the group of trackers numbered 151 in FIG. 6. Phase output 221 is coupled to diameter tracker 226, which is one of the group of trackers numbered 150 in FIG. 6. The signal on 222 is tracked for depth of the near artery wall, giving rise to a low-frequency analog depth output and depth rate-of-change output. The signal on 221 is tracked for depth of the far wall of the artery. Near-wall depth-tracking data travels from 225 to 226 on bus 227, providing a reference against which the signal on 221 is used to generate low-frequency analog signals representing artery diameter and rate-of-change of diameter. Since the vibrational changes in the depth and diameter signals are typically very small fractions of the total signals, the rate-of-change outputs are useful for emphasizing small motions and providing vibration data appropriate for digital conversion. The send/receive signal on 187 is needed by both trackers 225 and 226, as well as other sequencing data shown in following figures. The preset1 signal on 188 is needed to initialize depth tracker 225, and the preset2 signal on 189 is needed to initialize diameter tracker 226. Signals 187, 188 and 189 are coupled to trackers 225 and 226 as shown.

The ultrasound tracking function is explained in more detail with reference to the partial electronic schematic diagram of FIG. 9, the associated timing waveform diagram of FIG. 10, and Table 1, a state table that functionally describes the logic circuitry needed to complete the ultrasound tracker.

Referring first to FIG. 10, transmit waveform 206a is so designated because it represents a signal waveform carried by wire 206, FIGS. 7 and 8. Receive trace 222a represents the signal on wire 222 of FIG. 8. Trace 222a could correspond to either trace 13 or 14 illustrated on oscilloscope display 4 of FIG. 1. Observe that 206a is an irregular shape while trace 222a shows a pair of symmetric waveforms, representing compensated echo responses from an idealized thin-walled artery (e.g. in practice for setting up and testing the system before clinical use, a cellophane-tube "artery" whose fluid content differs in acoustic impedance from surrounding fluid). If transmit trace 206a were a simple pulse, then phase and amplitude distortions in the ultrasound system, especially in the complex transducer apparatus, would cause a somewhat irregular echo response waveform even for the simplest sound reflector, a flat interface. It will be noted in FIG. 7 that an arbitrary transmit-pulse waveform can be stored at low waveform addresses of memory 183 for analog reproduction as trace 206a. Furthermore, the echo-response waveform 222a from a simple reference reflector is easily recovered into high waveform addresses of memory 183 for subsequent transfer into CPU 152. With this capability plus appropriate analytic software, it is possible to design a digital transmit-pulse waveform embodying pre-compensation for the phase and amplitude distortions of the ultrasound system, so that the received waveform from a reference reflector will have desirable characteristics of symmetry and a minimum time duration consistent with the bandwidth capabilities of the ulrasound system.

Describing a method of deriving precompensated transmit waveform 206a in more detail, one preferred approach is to begin by loading an output pulse of minimum duration into the transmit-pulse portion of memory 183, e.g., a single number representing a positive peak with all other numbers representing a baseline or reference-zero signal. This pulse is converted and sent out through the ultrasound system, and a simple reference target, e.g. the flat surface of a block of steel oriented across and perpendicular to the ultrasound beam under water, is used to obtain an isolated reponse waveform for sampling. The response waveform is sampled, windowed (i.e. separated from other echo waveforms and transients of electronic origin) and Fourier-transformed. If g(t) represents the pulse response function g of time t, then G(f) can represent the complex Fourier transform of g with respect to frequency f. It is useful to define the time scale of t for Fourier transformation such that t=0 somewhere in the vicinity of the largest peak amplitude of the g(t) waveform. Then the magnitude ABS(G(f)) is examined as a function of f to ascertain the useful bandwidth of response amplitude with no severe minima. A desired pulse response waveform is then constructed, of comparable bandwidth. Start in the frequency domain and describe a smooth amplitude envelope that peaks at the center of the ABS(G(f)) band and becomes very flat as it goes to zero. Consider e.g. the amplitude function A(f) of Eq. 26:

$$A(f) = (1 - [(f - f0)/f1]^2)^3 \text{ for } (f0 - f1) < f < (f0 + f1) \quad [26]$$
$$= 0 \text{ outside the } (f0 - f1) < f < (f0 + f1) \text{ window}$$

This function peaks at center-frequency f0 and goes to zero at a distance f1 to either side of f0, where normally f1>f0. Set f0 at the center of the ABS(G(f)) function, and choose f1 as large as possible within the constraint e.g. that any bands where ABS(G(f))/A(F)<1 are no wider than than the minimum value of f1*[ABS(G(f))/A(f)]$^2$ in that band. What this states, in effect, is that the desired pulse response amplitude should remain smaller than the impulse amplitude response envelope except for narrow bands whose (power-gain)*(bandwidth) product is less than half the total bandwidth. If this criterion is not satisfied, then the frequency window of A(f) should be narrowed to exclude problematical regions of weak response of G(f), or at least to place such regions well out in the skirts of A(f) where the goal amplitude is low. If this or a comparable criterion is violated severely, then the pre-compensated pulse waveform will be dominated by ringing in frequency bands where ultrasound system response is weak, and this ringing will mean that the pre-compensated pulse has significant amplitude for an excessive time duration and cannot be fitted into a reasonable pulse-transmit time window. Having ascertained the widest practical amplitude window for the desired pulse response in the frequency domain, A(f), we define the Fourier transform H(f) of the desired pulse in one of two ways, depending on whether even or odd symmetry is desired:

(a) $Re(H(f))=A(f)$ and $Im(H(f))=0$ for even symmetry, or (b) $Im(H(f))=A(f)$ and $Re(H(f))=0$ for odd symmetry.

The choice here is of relatively little importance, since the 90° network of module 210 (FIG. 8) will provide the opposite-symmetry waveform. The time-domain desired-response waveform is then h(t), the inverse Fourier transform of H(f). Finally, to design a precompensated pulse waveform w(t) that results in the wave shape h(t) from simple reflectors, set the frequency-domain function W(f) according to Eq. 27:

$$W(f)=H(f)/G(f) \text{ for } f>0 \quad [27]$$

A definition of W(f) may be needed for negative frequencies, depending on the definition used for the complex Fourier transform and its inverse, and one may want $W(-f)=W(f)$ or $W=(f)=-W(f)$, depending on symmetries of the transform. The mathematician wishing more background on this and related choice for implementing the precompensated pulse waveform is referred to the Bruel and Kjaer *Technical Review* No. 1-1983, "System Analysis and Time Delay Spectrometry (Part 1)", by H. Biering and O. Z. Pedersen. With the appropriate definition of W(f), the function w(t) is determined by inverse Fourier transformation. This shape is the precompensated pulse waveform, which should typically extend to either side of t=0 as derived, but should go nearly to zero outside a reasonably short time window. The position along the time axis of w(t) is adjusted suitably, relative to the definition of time for the memory addresses that hold the transmit pulse. Amplitude of w(t) is also scaled suitably for the representation in digital memory as recalled for conversion by D/A converter 198. Minor adjustments may be needed in this procedure to fit time widow, peak amplitude, peak slew rate and similar constraints of the hardware system. Such adjustments will be manageable and clear to mathematicians of appropriate background.

It will be seen that other procedures will result in successful construction of a precompensated transmit pulse waveform leading to desirable characteristics in the receive pulse from a reference reflector. In general, the hardware for such a system must include means for digitally storing a programmable transmit-pulse waveform; means for retrieving the digital samples of the transmit-pulse waveform and converting the retrieved samples to analog signals in a repeatable time sequence; means for filtering and amplifying that analog signal sequence to produce an analog waveform appropriate for driving a transmitting ultrasound transducer; means for generating a reference pulse output of known characteristics and for recovering a resultant response waveform from a receiving ultrasound transducer (which may be the same as the transmitting transducer) and converting samples of that waveform into a sequence of digital words or numbers representing the values of the analog samples; and means for storing and analyzing those analog samples as derived from a reference ultrasound target in order to design a pre-compensated digital transmit-pulse waveform than lends desirable characteristics to the resulting received echo waveform from simple echo-producing reflectors. A method for making a digital pulse-precompensation system work is to use appropriate hardware to transmit a reference pulse of known, broadband characteristics; receive and digitize the resulting ultrasound echo response from a desired reference target; use the relationship between output waveform shape and the resulting received echo waveform shape to solve for a precompensated waveform shape that will lend desirable characteristics to resulting received echo waveform shapes; and finally to convert the computed precompensated waveform shape into a transmit-pulse signal over time, for application to the appropriate ultrasound transducer system.

Continuing with the ultrasound hardware, the send-/receive, preset1 and preset2 waveforms of wires 187, 188 and 189, FIG. 7, are represented as traces 187a, 188a and 189a in FIG. 10. These waveforms, programmed into memory 183 for sequential readout to latch 186, are part of the definitions for state Table 1, below. The analog-converted portion of transmit-pulse 206a is constrained to fall within the time boundaries of the high state of send/receive trace 187a. Depth of the near artery wall from the ultrasound transducer correlates with the delay time from the fall of trace 187a to a selected and tracked zero-crossing on receive trace 222a, which is a selected phase output on output wire 222 from multiplexer 224 (FIG. 8). This delay time corresponds to the durations of States 3, 4 and 5 as shown on the "State" axis across the bottom of FIG. 10.

Once initialized and tracking below slew rate, the ultrasound tracker functions as follows. In FIG. 9, a corrective feedback loop is formed of inverting integrator 250, non-inverting sample/hold amplifier 267, inverting integrator 252, comparator 255 receiving signals from 250 and 252, and logic that couples the output of comparator 255 to current-source 258 feeding the input of integrator 250. This current source is capable of being switched on and off and, in the on state, capable of having its current output polarity switched. Logic circuitry drives signal 268, "INT-ZERO", resetting the output of integrator 250 to zero in each cycle. The negative feedback loop just outlined follows a positive-going zero-crossing in the ultrasound signal on wire 222 from phase-selector switch 224 (FIG. 8), the output being converted to a positive-going logic transition by ground-referenced comparator 270. The output of 270 on wire 271 and trace 271a (FIG. 10) appears at interconnect circle 272, "ultra cmp", an input to the logic "state machine" described functionally by Table 1 (below). In more detail, integrator 1, designated 250 in FIG. 9, generates on wire 254 a dual-slope V-shaped waveform, 254a in FIG 10, that is used to compare the depth delay time with the magnitude of analog voltage −Vref, which appears at wire 253, the output of integrator 252. The magnitude of −Vref controls the time duration of States 3 and 4. State 3 begins when send-/receive signal 187a falls low, which triggers current enable signal "I-EN" at 265 to go high, switching on current-source 258 and causing integrator 250 to ramp negatively from zero volts. The State goes from 3 to 4 when the integrator output voltage on 254 crosses −Vref and causes a transition in the state of comparator 3, designated 255, whose output terminal is designated 256, "CMP3". The inputs of comparator 3 are wire 254 from integrator 250 (inverting) and wire 253 from integrator 252 (non-inverting). In response the comparator 3 transition, which is coupled to state-machine input 256, "CMP3", current-direction signal "I-DIR" at 257 changes, reversing the direction of the output of current-source 258 and reversing the slope of 254a. The State goes from 4 to 5 when voltage 254a ramps up across negative reference 260, "−int. thresh.", causing a positive transition in output 276, "CMP1", of comparator 1 at 261. The non-inverting input of comparator 1 is integrator output 254 and the inverting input is the negative reference potential of 260. During the time interval in which trace 254a would be ramping between the symmetric limits "−int. thresh." and "int. thresh." in tracking mode, a positive-going zero-crossing of selected-phase ultrasound signal 222 from multiplexer 224 (FIG. 8) will cause trace 254a to stop ramping and hold a constant value. The positive ultrasound signal transition drives the logic output of comparator 270 high. This logic transition appears on comparator output wire 271, trace 271a from State 5 to State 6, and on interconnect circle 272 labeled "ultra cmp". It will be seen that reducing the delay of the receive signal will cause an earlier transition on 271a, leaving a more negative value stored on trace 254a, in States 6 and 7 and the subsequent State 0 (beyond the right edge of FIG. 10—a negative stored value is illustrated) while increasing the delay will cause a more positive value to be stored on 254a. The logic prevents the stored value from dropping below "−int. thresh." or rising much above "int. thresh.". The latter logic-prevention is caused when the integrator-1 signal on 254 to the non-inverting input of comparator 2 at 278 crosses "int. thresh." at 277, applied to the inverting input of comparator 2. The output of 278 is coupled to state-machine input 280, "CMP2", and a positive transition at 280 drives "I-EN" at 265 low (if it is not already low), shutting off current source 258. With 258 shut off, the constant output held on integrator 2 (250, trace 254a) is transferred to output 275 of sample/hold amplifier 267 when control voltage 266, "S/H", goes high. The sample/hold output on wire 275, shown as signal trace 275a, couples to the input of integrator 252 and sets the negative of the output slope on wire 253, trace 253a, called −Vref. This signal is also labeled "−Pos. Out" at 285, since the signal represents the negative of tracked position, or depth. Similarly, the signal at the input of integrator 252 on wire 275 is labeled "Vel. Out" at 286, since the signal represents the velocity associated with changing "−Pos. Out". These position and velocity signals are coupled back to low-frequency analog acquisition module 153 (FIG. 6) as "depth" and "change" signals. Noise minimization in the velocity signal is especially critical, so normaly "Vel. Out" is lowpass-filtered before sampling. Computer algorithms for processing time-sampled phase-component data at the excitation frequencies include corrections for the predictable phase and amplitude alterations caused by such filters in the analog system. While the dot-dash lines near traces 254a and 275a represent zero reference potentials for those traces, the dashed line near 253a is a fixed-voltage reference line to sake the slope of 253a easier to see. In fact, trace 253a is always negative, its magnitude representing tracked depth, and the fractional change in 253 over a single ultrasound cycle never exceeds a small fraction of a percent. Trace 253a is greatly magnified in FIG. 10 to illustrate the change. Note that on the left of FIG. 10, trace 254a is a positive value retained from the previous cycle and held on sample/hold amplifier 267 as trace 275a from the beginning of State 0 to the beginning of State 7, when the new negative value held on integrator 250 (trace 254a) transfers to the sample/hold output. This sign transition reverses the slope of 253a, the output of integrator 2 on 253. The small adjustments in −Vref, on 253, alter the time needed for trace 254a to ramp down to −Vref and return to the vicinity of zero.

The logic machine needed to complete the ultrasound depth tracker is specified functionally by Table 1:

to a positive transition time of "preset1". In initialize mode, "TRACK" is low, and a high level on "preset1" will then bring on State 6, stopping the ramp. If "preset1" is already high upon entering State 5, the machine goes immediately to State 6 and the ramp is stopped at "−int. thresh.". This is a slew-rate condition to shorter delay. If "preset1" goes high after the machine enters State 5 but before trace 254a crosses the positive "int. thresh.", then the transition time of preset1 will control the level held on 254a, resulting in a self-correcting feedback to an equilibrium "−Vref". If trace 254a crosses "int. thresh." before "preset1" goes high, this transition drive comparator 2 and CMP2 high, which is seen in the table to be the third path of transition to State 6. The ramp will retain approximately the positive "int. thresh." value, and the time delay loop will be TABLE 1
State Table

| STATE | | INPUTS | | | | | | | NEXT STATE | OUTPUTS | | | |
|---|---|---|---|---|---|---|---|---|---|---|---|---|---|
| GRAY CODE | DEC | SEND /R | PRE- SET1 | CMP1 | CMP2 | CMP3 | TRACK | ULTRA CMP | (DEC) | I-EN | I-DIR | S/H | INT- ZERO |
| 000 | 0 |   | 1 |   |   |   |   |   | 1 | 0 | x | 0 | 0 |
| 001 | 1 |   | 0 |   |   |   |   |   | 2 | 0 | x | 0 | 1 |
| 011 | 2 | 0 |   |   |   |   |   |   | 3 | 0 | x | 0 | 0 |
| 010 | 3 |   |   |   |   | 1 |   |   | 4 | 1 | 1 | 0 | 0 |
| 110 | 4 |   |   | 1 |   |   |   |   | 5 | 1 | 0 | 0 | 0 |
| 111 | 5 |   | 1 |   |   |   | 0 |   | 6 | 1 | 0 | 0 | 0 |
| 111 | 5 |   |   |   |   |   | 1 | 1 | 6 | 1 | 0 | 0 | 0 |
| 111 | 5 |   |   |   | 1 |   |   |   | 6 | 1 | 0 | 0 | 0 |
| 101 | 6 |   | 0 |   |   |   |   |   | 7 | 0 | x | 0 | 0 |
| 100 | 7 | 1 |   |   |   |   |   |   | 0 | 0 | x | 1 | 0 |

NOTE: There are three conditions for going from State 5 to State 6

There are numerous circuit implementations of a State Machine obeying FIG. 1, e.g. a programmable array logic chip with appropriate interconnections. In a given state, the machine must give the specified outputs, and any of the specified combinations of inputs to a given state will result in a transition to the next state of the machine. In most cases, there is only one such input combination, but in the case of State 5, any of three input conditions will bring about State 6.

Referring to Table 1 and FIGS. 9 and 10, the system is tripped to State 0 from state 7 when send/receive (abbreviated SEND/R) line 187 and trace 187a from latch 186 goes high. In State 0, sample/hold amplifier 267 goes into hold mode, retaining the most recent input that was being held on integrator 250. A high state on preset1, line 188 and trace 188a from latch 186, triggers State 1, in which integrator 1 at 250 is reset to zero output on 254 and trace 254a. The fall of preset1 to zero bring State 2, with integrator 250 ready to ramp. The fall of send/receive line 187 and trace 187a to low brings State 3, in which a combination of a high current-enable (I-EN) on 265 and a high current-direction (I-DIR) on 257 activate current source 258 to cause a negative-going ramp on integrator 250, as seen on trace 254a. When the ramp crosses −Vref and causes a high output on comparator 3 (CMP3), State 4 begins and the current-direction signal (I-DIR) switches, causing the slope of ramp 245a to reverse. (The magnitudes of positive and negative slopes of the ramp need not match.) State 4 persists until 254a crosses −int. thresh., causing comparator one at 261 (CMP1) to give a high output, bringing on State 5. From this state the machine is ready to stop the ramp of 254a and hold a value for sampling and input to integrator 2.

A signal "TRACK" interfaced from CPU 152 via interface logic and a latch determines whether the tracker is following a zero-crossing or being initialized slewing to longer intervals.

Once initialization is accomplished with "preset1", the control line "TRACK" typically goes high to initiate tracking of a positive transition of the ultrasound comparator output, trace 271a. With TRACK=1, Table 1 shows that "ULTRA CMP" performs the same control function as "preset1" in the TRACK=0 state. Positive and negative slewing conditions are comparable, with stable tracking occurring when the positive transition of "ULTRA CMP" lands inside the time window where 254a is ramping from "−int. thresh." to "int. thresh.". For stability and noise rejection, the integration time constant of integrator 2 is made relatively long, so that this integration speed establishes a dominant effective pole in the tracking loop. This pole may be set in the vicinity of the upper band limit of the low-frequency vibration analysis system, e.g., around 1 KHz. The resulting effect of this pole on the important frequency behavior of "Vel. Out" on 286 must be incorporated in the digital compensation algorithms that infer true phases and amplitudes from filtered data inputs. The magnitude of the "int. thresh." window should be kept small, so that the upward range of 254a is stopped within plus or minus one-half ultrasound cycle of its zero crossing, or less. This tight slew-rate limiting avoids loss of phase lock from short bursts of electronic interference that might affect the ultrasound receiver. Slew rate need only be high enough for linear tracking of small vibrations and of pulsatile depth changes as the pressure fluctuations stretch the artery.

Once tracking of an ultrasound zero-crossing is established, the tracking point can be shifted forward or backward by 90° increments in the phase of the receive signal, by switching in 90° increments the phase signal selected by multiplexer 224 (FIG. 8) for output on wire 222 to the depth tracker. Hence, what appears as tracking of a positive-going zero crossing of the signal on 222 may appear as tracking of a positive or negative zero-crossing or peak on the reference-phase signal output 211.

The description has so far detailed only the tracking of depth of a single ultrasound feature, typically associated with the near wall of an artery. Diameter tracker 226 (FIG. 8) functions similarly to depth tracker 225 except that the dual-slope ramp corresponding to trace 254a begins its downward excursion at the transition from State 5 to State 6 of the depth tracker. Using a similar circuit, the ramp hits a negative reference threshold from a second integrator, turns around, and is stopped by an ultrasound comparator transition driven by the signal on multiplexer output 221 (FIG. 8). The diameter tracker initialization is on a positive transition of "preset2" and stabilizes when the depth tracker is stabilized to give a consistent near-boundary reference. The diameter signal tracks the time-differential between two variable events, the transitions of two ultrasound comparators. The diameter signal gives good rejection of common-mode depth signals, which may be many times larger than the diameter variation signal. It is clear that comparable depth and diameter tracker circuits can be dedicated to different ultrasound paths, using appropriate ultrasound signal-path selection. Such paths include the two out-and-back ultrasound paths and the transverse ultrasound path described above for the artery-tracking aspect of the invention.

Calibration Cuff Function

Sphygmomanometer cuff 11 (FIG. 1) is used optionally to reduce the pressure differential across the wall of the artery segment-under-test (e.g. part of carotid artery 40) by a known, time varying amount, normally below diastolic pressure so that the artery does not collapse. Cuff pressure change should be slow enough to permit axial blood flow to and from the cuff region, with resulting artery diameter change and pressure-differential equilibration. Cuff pressure is varied in a pattern, e.g. sinusiodal, designed to minimize the correlation between cuff and blood pressure changes. Cuff pressure change and vibration-determined blood pressure change can be correlated over unequal numbers of complete cuff and cardiac cycles (e.g. 10 full cuff cycles and a simultaneous 15 full cardiac cycles). The unequal rhythms minimize unwanted correlations of the cuff rhythm with all harmonics of the cardiac rhythm. Departure of the correlation slope from unity indicates an error in vibration-determined pressure change, leading to a calibration correction.

DESCRIPTION OF A WHOLE-ORGAN EMBODIMENT

Figure 11A:
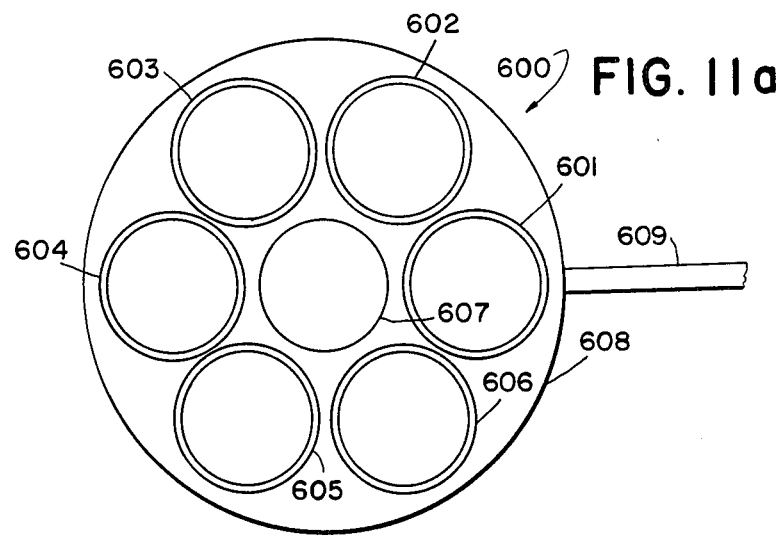
Figure 11B:
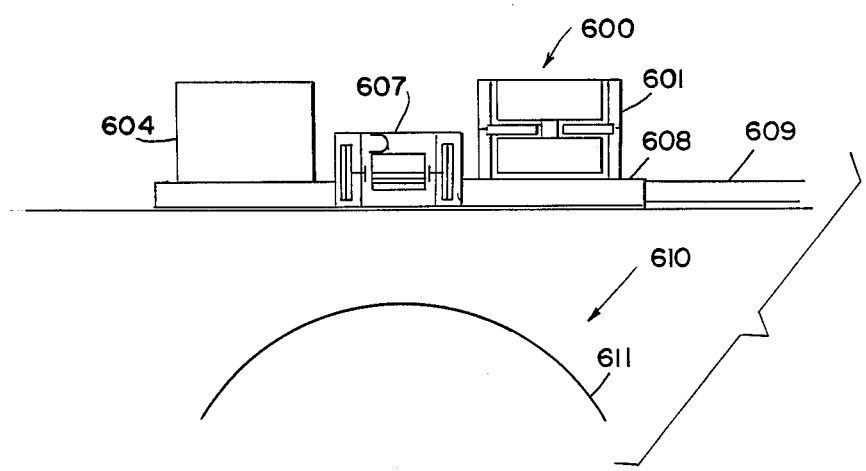
FIG. 11b is a side section view.

A variation of the invention is adapted e.g. for measuring mechanical properties of whole organs and internal pressures in fluid-filled organs, e.g. urinary bladder, or edematous organs. FIGS. 11a and 11b show that driver/sensor assembly 600 is a round disc with six driver assemblies, 601 through 606, arrayed hexagonally around the perimeter, and with single ultrasound assembly 607 in the middle. The six matched driver assemblies are each like the assembly of housing 60 and central moving element 61 of FIGS. 2 and 4. The description accompanying FIG. 4 applies to these driver assemblies as well. All six assemblies are wired electrically in parallel and generate parallel vibrational forces against disk 608, to which they are affixed. Driver/sensor assembly 601 is shown in simplified cross-sectional view in FIG. 11b, to clarify the orientation and relationship to the cross section of FIG. 4. Ultrasound assembly 607 (shown in FIG. 11b in simplified cross-section, to clarify orientation in the larger assembly) lies in the center of disk 600. The same cross section appears in more detail in FIG. 11. Interconnection to a computer/controller is provided by cable 609 (FIGS. 11a, 11b). FIG. 11b shows assembly 600 lying on the surface of tissue 610, with contour 611 indicating the upper boundary of an underlying organ.

In operation, assembly 600 is a three-dimensional-measurements counterpart to assembly 1 of FIGS. 1, 2 and 3. Assembly 600 is capable of sensing its vibrational velocity and the total vibrational force exerted on underlying tissure. The force measurement differs from assembly 1, which measures applied force only over a central transducer segment. The single ultrasound assembly of 600, lacking an acoustic lens, generates a roughly columnar beam, with the only significant divergence with depth arising from aperture diffraction. The beam has two-axis steering, which is servo-controlled to lock onto and track an ultrasound echo source over time.

An objective of the whole-organ embodiment is to induce vibrations in an underlying organ, and then to measure, over a range of frequencies, the surface mechanical impedance and the transfer ratios from surface driver velocity to velocities of various internal organ surfaces. The spectrum of responses is analyzed using simulation algorithms, as described below. The simulation outcome is a mathematical model of the vibrating system, with its coefficients adjusted so computed responses match observed responses. The adjusted model coefficients indicate the vibrational parameters of the organ tissue, including density, viscosity and shear modulus, and possibly including the frequency-dependences of viscosity and shear modulus, as these parameters may be influenced by visco-elastic creep. These parameters can be correlated with normal or pathological tissue conditions, e.g. the changes associated with scirrosis of the liver or with cystic kidney disease.

A further use of the whole-organ embodiment of the invention is to determine internal pressure in an organ, whether that pressure be attributed to free liquid or semiliquid contents, e.g. in the urinary bladder or the eye, or to abnormal fluid retention in cells or in the interstices between cells. The elasticity associated with a fluid pressure differential, whether abrupt across a thin organ wall, or graduated from the center to the surface of an edematous organ, gives a different series of vibration-mode resonant frequencies than is associated with an elastic modulus. This difference was discussed above in a cylindrical context for distinguishing blood pressure from arterial wall stiffness in the systemic artery pressure embodiment. Analogous differences exist for other organ shapes. The measurements and analysis taught here provide means for distinguishing fluid-pressure-related and elastic-modulus-related elasticities, even in heavily over-damped situations. Note that pressure-induced restoring impedance in a roughly spherical organ varies as the product of radius times pressure, whereas restoring impedance per-unit-length in a cylindrical organ or vessel varies as pressure alone, independent of radius.

Where fluid pressure effects vary over time between vibrational measurements, even slowly over hours or days, the change can provide pressure-baseline data, opening the way to the powerful network algorithm, for determining organ mechanical impedance. The three-dimensional network algorithm differs from the two-dimensional cross-sectional network algorithm primarily in depending on total surface-driver vibrational force, as opposed to a representative force per-unit-length. This difference accounts for the dissimilarities in the force measurement methods of this whole-organ embodiment versus the systemic artery pressure embodiment.

We now examine the steerable ultrasound assembly 607, shown from above in FIG. 12a, and from the side in FIG. 12c. Two possible magnetic field patterns for the perspective of FIG. 12a are illustrated schematically, side by side, in FIG. 12b. In FIG. 12a, we see a torroidal magnetic field generator surrounding a gimbaled center assembly. The field generator consists of four curved magnetic core elements 621 through 624, each mostly covered by curved winding segments 625 through 628. Each core element is a 90° segment of a torroid, and the wound elements abut to form a complete torroidal core. Opposite windings are joined electrically as pairs. Thus, windings 626 and 628 are wired to give a magnetic field across the torroid center, sloping from upper right to lower left, as illustrated on the left in FIG. 12b. Similarly, windings 625 and 627 are wired for a field from upper left to lower right, as on the right in FIG. 12b. Current reversals change the field directions. Within saturation, power and bandwidth limits, field strength and direction across the torroidal center can be controlled continuously by controlling currents in the two winding pairs.

Upper layer 630 of the gimbaled center assembly is an axially-poled, disk-shaped permanent magnet. Magnetic fields from the torroidal wound core generate torsional moments on the magnet, tending to align the magnet axis to the cross-plane field. The gimbal consists of jewel needles 631 and 632 (FIGS. 12a and 12c), extending inward from the torroidal core on the left and right; ring 633, seen from above (FIG. 12a) and in section (FIG. 12c), with bearing cups for needles 631 and 631; needles 634 and 635 (FIG. 12a only), extending inward from ring 633 above and below; and bearing cups for needles 634 and 635 in magnet 630. The gimbal permits the magnet to tilt in response to the driving magnetic field. Five thin, u-shaped spring wires restore the magnet to axial alignment, so that the equilibrium deflection angle is a function of applied field strength, and of temperature, which affects the magnetic moment of the permanent magnet. Of these five, wire 636 is illustrated in FIG. 12c. The five wires are arrayed with the openings of the u-shapes pointing radially outward to the vertices of an imaginary regular pentagon. Each wire is affixed to top assembly cover 640 and to magnet 630. These spring wires provide four signal leads for four 90° metallization sectors of piezoelectric ultrasound disk 641, plus a common ground lead. The sector metallizations are numbered 642 through 645 as they are exposed in the central cross-sectional view of FIG. 12a. These metallizations are on the top of ultrasound transducer disk 641, where the disk is affixed to magnet 630. The common ground metallization covers the entire lower surface of disk 641, which is bonded to quartz acoustic interface layer 650. This interface is in turn bonded to acrylic plastic acoustic interface layer 651, whose lower surface contacts fluid that envelops the gimbaled assembly. The fluid is contained in an envelope whose top surface is cover 640 and whose bottom surface is cover 652. Cover 652 forms the center of the lower surface of disk 608 (FIGS. 11a and 11b), and contacts the patient. The ultrasound impedance of the cover is close to that of the ultrasound-transmitting fluid and of human tissue, to minimize ultrasound reflections.

The ultrasound assembly is aimed using digital control. Algorithms regulate magnetic-drive field currents to produce desired aiming motions, taking into account magnetic torques, restoring torques, inertia and fluid-damping forces. The aiming mechanism as described here operates open-loop, to the extent that magnet angular position is calculated but not actually measured. Absolute angular accuracy of the device is not critical. Angle-correcting feedback comes when a desired ultrasound target is computer-identified and tracked, using circuitry like that shown earlier in the application.

Angular error signals for alignment to center an ultrasound echo source are generated from the phase differentials of echo arrival at the four sectors of the ultrasound disk. Sectors closer to the echo source will give phase-leading echo responses, relative to sectors farther from the echo source. The disk is aligned when the four phases of the tracked signal match.

Circuitry to detect ultrasound phase error signals is outlined as follows. The same ultrasound drive pulse voltage is applied to all four sectors of disk 641. The return echo signal is received on two separate channels, split between either left versus right sectors, or up versus down sectors, depending on solid state switch settings. The split alternates left-right and up-down on alternate pulses. The two amplified channel outputs are summed to a common-mode channel, which is processed like any of the ultrasound channels of the systemic artery pressure embodiment, to permit tracking of a zero-crossing. The left-right and up-down differential signals are processed separately and sampled as the tracked ultrasound zero-crossing of the average ultrasound signal is detected. At the moment of sampling, the tracked ultrasound signal is changing rapidly, so that slight phase differentials between the left versus right or up versus down regions of the ulrasound disk result in significant signal differentials, which are sampled. These samples are roughly proportional to ultrasound signal strength multiplied by phase differential. The samples are filered to give a narrower band signal, which is sampled and digitized by the computer for servoing the aim of the ultrasound disk to straight-on. Thus, an alignment lock can be established as soon as a zero-crossing phase lock to an ultrasound feature is established.

The ultrasound system can scan its accessible angular sector and a prescribed depth range, recording the approximate three-dimensional locations of strong echo responses. Vibration responses are also noted. The array of responses is studied, possibly by human operators as well as the computer, and echoes representing desired vibration-tracking targets are identified. Those targets are subsequently re-located and tracked while driver frequency is varied. The vibration data for each target consist of target velocity and driver force, each resolved into 0° and 90° phase components relative to driver velocity. These parameters are typically expressed as ratios to driver velocity amplitude. The data are collected over an array of frequencies.

Force and velocity measurement for the whole-organ embodiment is different from the systemic artery pressure embodiment. Since total driver force is to be measured, rather than force from a portion of the driver, it is possible to infer force from the electrical responses of the electromagnetic vibration drivers, without using separate force and acceleration transducers. Velocity can be inferred similarly. The inference is based on the driver coil voltage developed in response to element motion. When a driver reaction-mass element moves relative to the housing and driver plate, the magnetic fluxes linking the coils are altered. A fixed, rigid reference element, similar to the six driver elements, uses a secondary coil current to cause the same flux change that is induced by the average axial motion in the six driver elements. The secondary current necessary to balance the reference-element primary voltage against the voltage across the six drivers is a measure of displacement response. This measure is used to determine velocity and force response.

Figure 13:
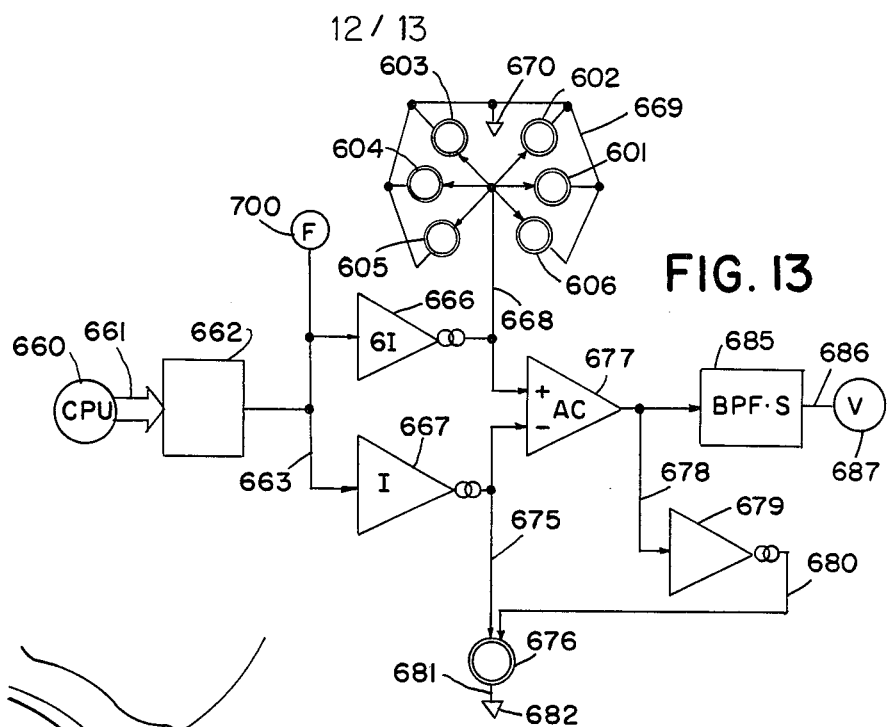
FIG. 13 is a block flow diagram of vibration-driver velocity measurement for the drivers of FIG. 11.

Implementation of this displacement-response measurement is detailed in the circuit diagram of FIG. 13. From interconnect circle 660, labeled "CPU" (computer), multiwire bus 661 carries control signals and data to digital function generator 662, which stores one or more waveform periods and plays them out cyclically onto wire 663 and interconnect circle 700, labeled "F" (force). Wire 663 couples to current amplifiers 666 and 667. The output of amplifier 666 is six times the current output of amplifier 667, and drives the six parallel-connected electromagnetic drivers, 601 through 606, as joined together and to amplifier 666 by wire 668. The opposite ends of the driver windings connect to wire 669, which is grounded at 670. The lower current of amplifier 667 is coupled via wire 675 to reference electromagnetic driver 676. This reference driver matches the other six except that the housing and central moving element are locked to fixed relative positions. The space occupied by o-rings in the other six drivers is occupied by a secondary winding in the reference driver. The difference between the reference-driver primary voltage and the voltage across the six parallel drivers is the voltage difference between wires 668 and 675. Wire 668 connects to the "+" input of high-gain AC differential amplifier 677, while wire 675 connects to the "−" input of the same amplifier. This amplifier includes high-pass input filtering and feedback to nullify DC input offsets while leaving operation at oscillator frequencies virtually unaffected. The greatly-amplified AC difference signal is coupled from 677 via output wire 678 to the input of current amplifier 679. The resulting current output is coupled via wire 680 to the secondary coil in reference-driver 676. Both primary and secondary windings in 676 have their opposite ends connected to ground wire 681, which is grounded at 682.

The function of the feedback loop through the secondary winding in the reference driver is to determine the average vibrational change in position of the magnet-plus-coil elements in the six parallel drivers, relative to the housings and center-washers. Position changes divert magnetic flux, inducing primary winding voltages proportional to rates-of-change of flux. The feedback loop through the reference secondary winding provides a secondary current such that the AC magnetic flux imbalance in the reference drier almost exactly matches the average of the motion-induced flux imbalances in the six matched drivers. The secondary current needed to accomplish the primary voltage balance is an accurate measure of average relative position changes of the six moving driver elements. The close flux matching achieved between the reference driver and the average of the six moving drivers causes matched magnetic non-linearities and matched parasitic eddy currents, so that these artifacts are minimized in the feedback signal developed on wire 678.

The voltage on wire 678, representing vibrational position change, is coupled to the input of filter 685, labeled "BPF.s" (bandpass filtering combined with time differentiation, the latter indicated by the operator ".s"). The output signal from filter 685 on wire 686 is coupled to interconnect circle 687, labeled "V" (velocity). This signal represents a relative average velocity of the driver housings and center elements. This signal is sampled, digitized and frequency-analyzed by the system computer as with the systemic arterial pressure embodiment. When the computer interprets the analog data, the velocity- and force-determining formula takes into account the known reaction masses of the six drivers and the restoring characteristics of the support o-rings in the drivers. There is also a temperature correction factor, based on the temperature-sensitivities of the permanent magnets in the six driver elements. Temperature of the reference element is relatively unimportant. A temperature sensor on plate 608 provides a signal that is digitized and fed into the computer. The coefficients in the algorithm to determine velocity and force are adjusted by a calibration procedure in which the driver plate is placed against loads of known mechanical impedance and electrical responses measured at various frequencies.

DESCRIPTION OF AN OPTHALMIC PRESSURE EMBODIMENT

Another variation of the invention measures intraocular pressure by inducing, measuring and analyzing vibration responses, and by measuring eyeball diameter. The system includes visual feedback from the patient to measure opthalmic vibrational motions. The computation system uses a simulation algorithm to interpret data. A network algorithm can also be applied under certain circumstances for refining and checking simulation results. Subsets of the data suffice to determine pressure with fair accuracy, but the combination of all the measurements taught here determine a more precise pressure.

Figure 14:
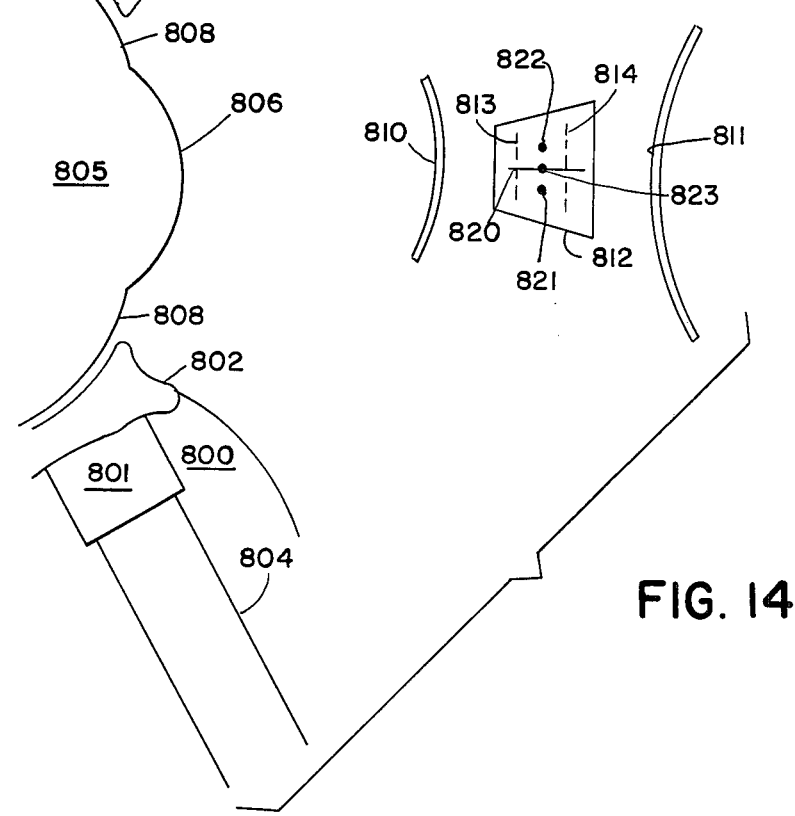
FIG. 14 is a diagrammatic representation of an intraocular pressure-measuring aspect of the invention.

Vibrational excitation plus surface-velocity and force sensing functions are combined in a single driver element. Vibration signal decoding electronics are very similar to the whole organ embodiment, as described with reference to FIG. 14. A single magnetic driver, 800 in FIG. 14, replaces the function of the six parallel-wired drivers 601 through 606 (FIG. 13). The reference driver is electrically matched to the moving driver, but locked against vibrational motion, as with the reference driver of the whole organ embodiment. The drivers are typically smaller than those used in the systemic artery pressure and whole organ embodiments, but are otherwise similar in design. Drive currents to the actual driver and reference driver are matched. Moving housing 801 of driver 800 makes direct contact with lower eyelid 802, inducing vibrations through the lid into the eye, shown generally at 805. The relatively heavy central winding and magnet structure is coupled to rigid supporting post 804. The post is anchored in an adjustable support structure for resting the chin and ocular orbits in a stable position. When the head is steadied, post 804 is extended manually to bring housing 801 into gentle contact with the lower eyelid of the open eye. Post 804 is then locked in place for measurements. Velocity and force responses in the eye are deduced from electrical responses of the coil in driver 800, using a circuit similar to the FIG. 13 circuit. A difference is that the amplitude of the digitally-controlled oscillator drive signal is computer-controlled, as well as the frequency.

A first estimate of intraocular pressure can be derived using the mechanical driver response alone. At vibration frequencies well below the lowest resonant frequency (typically 30 Hz) of the eyeball, measured mechanical impedance reflects primarily the effective moving mass of the eyeball, moving substantially as a rigid sphere partly surrounded by a soft semisolid characterized by an additional moving mass, a velocity damping coefficient and a restoring constant. The coupling is through the lower eyelid, which behaves primarily like a spring at low frequencies. To better characterize the effective eyelid spring constant, vibration measurements are taken at higher frequencies between opthalmic resonances, chosen such that the eyeball behaves as a comparatively rigid body. These measurements complete, the driver explores vibrational impedance responses in the vicinities of low-frequency opthalmic resonances. Interpretation of the data depends on eyeball diameter, on the effect of partly-surrounding tissue mass (which varies with eyeball protrusion from the head) and on an average tissue density that varies little and can be guessed. The measurements well below resonance assist in estimating the effective vibrating mass of the tissue that partly surrounds the eyeball.

Interpretation of the mechanical vibration data is improved by a measurement of opthalmic diameter. The curvature of sclera 808 (the white of the eye) is measured by observing the reflections of two lights on the sclera. Lights 810 and 811 appear as narrow, curved line-sources of illumination, oriented roughly vertically to either side of a display screen. (The lights must typically be spaced further than 45° from the eyeball-to-display center axis to make the sclera reflections visible to the patient.) The curvature of the lights is chosen to make the reflections on the sclera to the left and right of cornea 806 appear approximately as straight vertical lines. Tests are conducted in a dark-walled booth, to minimize other reflections from the sclera. Clear display screen 812, between the two lights, is temporarily backed by a mirror. Vertical cursors 813 and 814 are generated just in front of the reflective mirror surface, e.g. using light-emitting diodes and fiber optics. Switching of light-emitting diodes on different fiber optic elements moves the visible cursor positions by small increments. The positions are adjusted by the patient controling adjustment knobs, until the patient, looking in the mirror, sees the light reflections on the sclera aligned to the two cursors. The aligned cursor positions indicate the size of the eyeball. This size measurement refines the interpretation of the vibrational-impedance measurement, yielding an improved pressure estimate.

To obtain further vibration response data, the mirror surface on the back of screen 812 is replaced by a black surface. Lights 810 and 811 are switched off, as are the diodes illuminating cursor lines 813 and 814. The display now consists of strobed horizontal line 820, synchronously-strobed dots 821 and 822 above and below the center of line 820, and independently-strobed dot 823 in the middle of line 820. Peak strobe intensity must be fairly high, so that flesh tubes are typically used for this function instead of light-emitting diodes. Line 820 is strobed in two alternating colors, e.g. red and blue-green. The strobe flashes are synchronous with the vibration drive signal, with (e.g.) the red and blue-green strobe times separated by a 180° relative phase angle. As the eyeball vibrates, the cornea tilts and causes the image of the strobe display to move up and down on the retina. When the patient observes the red-strobed line converged with the blue-green-strobed line to form an apparent white line, this indicates that the moving line image on the retina is crossing the same position, moving in opposite directions, at the times of the strobe flashes. The phase of the red flash (and consequently of the opposite-phase blue-green flash) is computer-set to a specific timing angle relative to the force computed to be effectively driving the opthalmic vibration mode of interest. The patient adjusts a knob that controls driver frequency (via the computer), in order to converge the red and blue-green strobe lines. Convergence indicates that the zero-crossings of the vibrational displacement of the cornea and lens are in-phase with the computer-controlled strobe-timing phase. By repeatedly resetting the strobe phase angle relative to computed vibrational force and allowing the patient to adjust frequency to reconverge the lines, the computer determines values for the opthalmic vibrational phase response angle as a function of frequency.

Dot 821 flashes blue-green with the blue-green flash of line 820, while dot 822 flashes red with the red flash of line 820. The apparent visual positions of dots 821 and 822 are not perturbed by vibrational motion when the colors of line 820 are converged. To measure angular response amplitude of the cornea and lens, dot 823 is strobed alternately red and blue-green 90° out-of-phase with the respective blue-green and red flashes of line 120 and single-color dots 821 and 822. When the phase adjustment has converged the center line, the two color images of dot 823 appear to have a maximum vibration-induced angular separation. The user adjusts the vibration driver amplitude, thereby adjusting the perceived dot separation to converge the red flash of dot 823 with the blue-green flash of dot 821, and the blue-green flash of dot 823 with the red flash of dot 822, to form two white dots. To the extent that angular image response of the eye depends on angular deflection of corneal surface 806 and on the well-known refractive index of the cornea (or of the type of contact lens resting on the cornea, which must be provided as computer input), this amplitude adjustment step tells the computer the excitation required to achieve a reference angular tilt response amplitude of the cornea. The amplitude response scaling equation is adjusted for the typical effect of lens vibrational movement on the observed angular response. Given the opthalmic radius-curvature, these angular response sensitivity measurements may be converted to displacement amplitude/responses elsewhere on the eye. The resulting data tell the computer substantially the same thing that ultrasound data tell the computer in the whole organ embodiment, namely, the amplitudes and phases of organ vibration velocities associated with surface-measured forces and velocities at a number of frequencies. (As mentioned, a miniature variant of the whole-organ embodiment can determine intraocular pressure using ultrasound instead of visual measurements.)

A final refinement permits application of the network algorithm to intraocular pressure determination. Applicability of this refinement depends on a combination of pulsatile pressure-change amplitude in the eye, patient visual acuity, and the maximum opthalmic vibration amplitude determined to be safe. Since intraocular pressure pulsates somewhat with blood pressure, convergence of line 820 will not be steady. The patient is asked to adjust frequency until line convergence is achieved at one peak of the opthalmic pressure waveform, with the red line moving above the blue-green line at other times. The patient is then asked to adjust frequency for convergence at the opposite extreme of the pressure waveform, with the red line moving below the blue-green line at other times. This frequency-separation at constant phase is easily translated into phase-separation at constant frequency, given the results of other measurements. Finally, the patient is asked to adjust the angular separation of dots 821 and 822 (e.g. by mechanical adjustment of the strobe optics) to match the peak separation observed from pressure-induced variation in convergence of line 820. This adjusted spacing, measured and digitally-interfaced, tells the computer the amplitude of the pulsatile response-variation measurement. This completes the data collection needed for applying the network algorithm, thus further refining the pressure determination.

The vibration amplitudes and energy levels allowable in this embodiment must be restricted for safety reasons, particularly to avoid risk of retinal detachment. For this reason, the visual display screen subtends a small visual angle and illumination is made quite bright, to maximize visual acuity for small-vibration observations. The vibration driver system can sense approximate response amplitudes and precise applied vibrations power levels without the benefit of visual observations. The system is designed both to monitor and restrict maximum excitation levels, and to be electrically incapable of delivering dangerous vibrational energy levels.

There are time-varying display alternatives to the stroboscopic display described above, e.g. an oscilloscope with horizontal sinusoidal beam deflection at the driver frequency. Vibrational response of the eyeball to the driver acting above or below the cornea will cause a vertical deflection of the perceived spot, resulting in a perceived lissajous ellipse or circle if the spot deflection frequency matches opthalmic excitation frequency. The appearance of a circle or ellipse with vertical and horizontal symmetry axes then indicates a + or −90° phase angle between spot deflection and opthalmic vibration response, while the appearance of a sloping line segment indicates a 0° or 180° phase angle. Many designs for variable displays synchronized to vibration driver excitations can produce perceived colors and geometric patterns indicative of opthalmic vibrations responses.

DESCRIPTION OF A PULMONARY ARTERY PRESSURE EMBODIMENT

Figure 15:
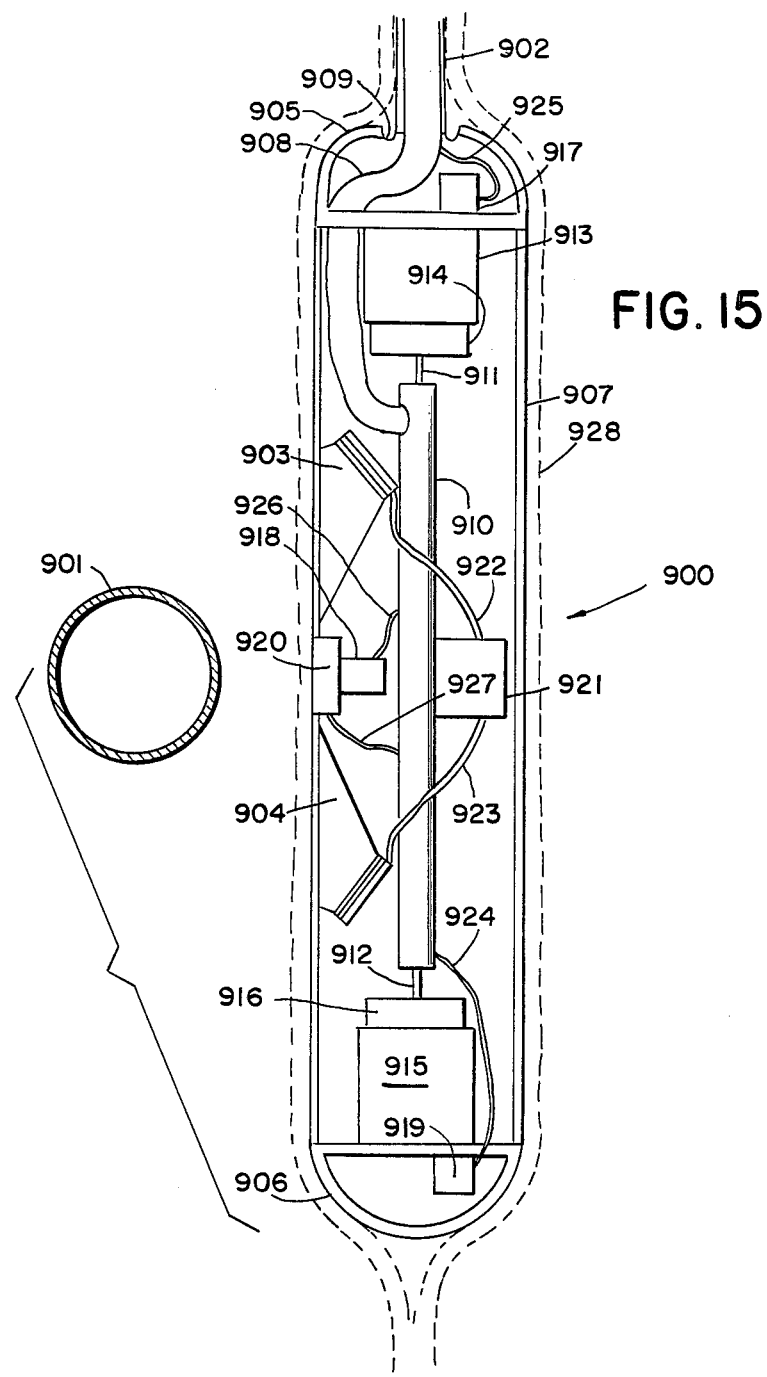
FIG. 15 is a diagrammatic cutaway view of the vibration driver and sensors in a pulmonary arterial pressure-measuring aspect of the invention.

Another variation of the invention is adapted for measuring blood pressure in the right pulmonary artery, in the vicinity where the artery crosses roughly horizontally at right angles to the esophagus. Vibration driver/sensor assembly 900 of FIG. 15 is swallowed and positioned partway down the esophagus, opposite pulmonary artery segment 901, shown in section. The esophageal wall is indicated by dashed line 928. The assembly is rotated and adjusted vertically via flexible cable 902.

The assembly, shown cut open, contains a pair of defocused ultrasound transducer assemblies, 903 and 904, which are very similar in construction, relative positioning and function to assemblies 62 and 65 of FIGS. 2 and 3, described in conjunction with the systemic artery pressure embodiment. By manual axial positioning of assembly 900, the operator matches the depths of two artery-wall echo traces on an oscilloscope, as with traces 13 and 14 of FIG. 1. Rotational alignment achieves maximum echo signal strength from the artery-wall target. This is accomplished in much the same way that the operator adjusts assembly 1 of the systemic artery pressure embodiment to align with the underlying artery, using a digital signal-strength readout.

Vibrational excitation is generated through length-change of assembly 900, as curved end caps 905 and 906 vibrate axially. Cylindrical housing 907 stretches to allow the relative motion of the end caps. This housing is a composite structure of compliant polymer (e.g. silicone rubber) with circumferential filaments (e.g. fiberglass) that minimize diameter changes but affect bending and length change minimally. Cable 902 emerges into curving segment 908 passing through cap 905 and into housing 907, providing vibration decoupling between external cable 902 and cap 905. Flexible membrane 909, bridging the circular gap between cable 902 and cap 905, is curved into 905 to roll with axial cap motion for vibration decoupling. Thrust between the end caps is supported by rigid tube 910, which terminates in end plugs from which emerge thin, short flexible rod segments 911 and 912, whose proportions give high bending compliance with low axial compliance and no buckling under working axial loads. Axial drive is provided by two magnetic driver assemblies consisting of housings 913 and 915, which move axially relative to their central magnet/winding assemblies terminating in pedestals 914 and 916. Rod segments 911 and 912 terminate in pedestals 914 and 916, transferring thrust from the pedestals to tube 922 while allowing limited bending of the housing and end caps. The driver housing and pedestal are analogous to housing 801 and pedestal 804 of FIG. 14, as described in relation to the opthalmic pressure embodiment. Detection of relative vibrational motion of the end caps is by analysis of driver electrical responses, using circuitry similar to that used in the whole organ and opthalmic pressure embodiments.

End-segment motion compresses and decompresses the gas (e.g. air) in housing 907 without significantly perturbing the housing diameter, so that vibrational excitation is analogous to an acoustic suspension loudspeaker with twin drivers at the ends of a closed cabinet of rigid diameter. A net volume-change vibration drive is desired, since this motion induces a vibration field that attenuates more gradually and smoothly over space than constant-volume vibration modes. The hoop stiffness of housing 907 prevents radius-change from offsetting volume changes caused by end-motion, while the high bending flexibility (within angular limits) prevents housing rigidity from interacting significantly with tissue vibrations that bend the housing.

As the relatively rigid and heavy spinal column lies immediately dorsal to assembly 900, on the right in FIG. 15, the tissue displacements off moving end caps 905 and 906 normally interact to produce significant lateral translational vibrations and bending vibrations in the assembly. Acceleration sensors 917, 918 and 919 detect left-right lateral vibrations near the top, center and bottom regions, respectively, of assembly 900, thus quantifying translational and bending motions in a plane substantially perpendicular to the axis of artery 901. The ultrasound-detected arterial motions are minimally affected by un-measured vibration components.

To provide still more data, fluid pressure sensor 920 is placed adjacent to acceleration sensor 918, on the assembly surface closest to artery 901. This sensor detects pressure exerted on the sensor assembly surface adjacent to the artery, responding from DC up through the vibration-frequency band of the drivers. Hence, the sensor can feel the low-frequency push as artery 901 expands with each heartbeat, and it can feel the effects of changing tissue stresses related to the diameter-change of the artery. In this way, the low-frequency pulsations of the artery itself are examined as a vibrational excitation that indicates properties of the artery and its near surroundings.

Cable 908 enters tube 910. The ultrasound coaxial cable travels via tube 910 to assembly 921, which contains broadband amplifiers transistor switched like those in assembly 56 of FIGS. 2 and 3, so that three-axis ultrasound resolution is achieved. Flexible wire braid 924, originating from cable 908 (which extends from cable 902), emerges from tube 910 to couple power and signals to and from acceleration transducer 919. Likewise braid 926, also originating from cable 908, emerges from tube 910 to couple power and signals to and from assembly 918, and similarly for braid 927 and assembly 920. Similar braid 925 emerges directly from cable 908 to couple to acceleration transducer 917.

The system gathers substantial data about the artery, including both frequency-baseline and pressure-baseline variations. Because of lag between pressure and diameter responses observed in the pulmonary artery (apparently caused by visco-elastic creep response in the artery wall), vibrations are sometimes measurable at equal radii and with sufficient pressure separation to permit solution of the network algorithm to useful accuracy. Preliminary to network solution, simulation algorithm techniques are applied to translate the three-dimensional vibration field problem into an equivalent two-dimensional problem, amenable to network techniques taught in conjunction with the systemic artery pressure embodiment.

Application of the simulation algorithm involves representing the system as interacting simple vibrating shapes. At a distance, the vibration fields from end caps 905 and 906 appear very similar to the fields of two spheres vibrating in the simplest volume-change mode. The spinal column to the right of assembly 900 in the diagram acts like a partial vibration mirror, creating the effect of a second image-pair of vibrating spheres. The field strength, phase and apparent distance (presumed directly to the right) of these image spheres from assembly 900 are inferred from the translational motions of acceleration sensors 918, 919 and 920. The resulting effective four-source field induces smoothly-tapering Mode 1 and Mode 2 excitations in the pulmonary artery, with minimal excitation of Mode 3 and above. Designing for the correct spacing between end caps 905 and 906 relative to their expected distance to the right of artery 901 helps to minimize average Mode 3 excitation. As there are pressure and stress variations axially along the artery, there is axial vibrational flow, resulting in net cross-section area change in the ultrasound plane. This appears as Mode 0 vibrational excitation in the ultrasound plane. The Mode 1 and Mode 2 vibrations vary slowly enough with respect to axial distance along the artery that axial motion associated with axial rate-of-change of these modes can be ignored. Hence, Mode 1 and Mode 2 excitations are treated as simple two-dimensional modes locally, anywhere along the artery length. The three-axis ultrasound system provides enough data to resolve Mode 0 from Mode 2 unambiguously in the ultrasound plane without symmetry assumptions (not the case with Mode 1 and Mode 3 excitation), since Mode 0 motion is described entirely by a single amplitude and a single phase (unlike Modes 1, 2 and 3, each of which can exhibit two amplitudes and two phases because of the possible differing-axis excitations).

The excitatory field of the four vibrating spheres can be resolved computationally, at any point along the artery length, into an axial translation, a transverse translation (observed as Mode 1), a transverse two-dimensional shear in the cross-sectional plane (observed as Mode 2), and a shear component associated with Mode 0 motion in the cross-sectional plane, accompanied by an axial velocity gradient. Of these vibration components, the transverse shear component associated with Mode 2 excitation accounts for most of the vibrational energy flow that is pressure-sensitive. Focusing on this component, a network algorithm solution is obtained, using pressure-baseline data at constant diameter. From the four-source vibration field model, the axial variation in Mode 2 excitation is estimated and an effective excited length calculated as follows. The Mode 2 excitation amplitude as a function of axial position is divided by the amplitude computed for the ultrasound-plane. This amplitude ratio is squared (giving an energy ratio) and integrated with respect to distance over the length of the pulmonary artery. The resulting integral is the effective excited length. For network algorithm solution, driver force and velocity may be interpreted as axial force and relative axial velocity of the end caps. Two-dimensional force associated with the ultrasound-measured vibrations is axial force divided by the effective excited length just described. The network algorithm is then solved by the methods shown in the context of the systemic artery pressure embodiment. (If the image-pair vibration is significantly phase-shifted from the primary pair, a more complicated network algorithm may be needed, taking into account differing effective excited arterial lengths for two different vibration phases.) Network solution data feed into the analytic function fit algorithm, yielding values for absolute pressure.

Further computational refinements provide a consistency check for the network solution, as well as an estimate for tissue elasticity around the pulmonary artery, which can mimic blood pressure significantly for the low pressure range of concern (typically below 30 mm Hg). The heart-rate pulsations sensed by surface-pressure sensor 910 help give an estimate of tissue elastic modulus near the artery. The measured pressure response is sensitive to tissue shear stresses acting normal to the sensor surface. Correlating these stresses with pulsating ultrasound-measured artery diameter and distance gives an indication of tissue elasticity.

The network solution gives an estimate of changing blood pressure that can be correlated with pulsatile diameter changes to estimate artery diameter elasticity. The four-source vibration simulation predicts Mode 0 excitation along the artery length. Combining this prediction with ultrasound-measured Mode 0 response and with an elastic tube vibration model (based on Fourier analysis and the elastic tube theory that has been used to study pulse wave propagation in arteries), an independent estimate of diameter elasticity is obtained. Comparing these two elasticity estimates gives a consistency check.

Since the network solution just described relies on data showing pressure differences at equal diameters, and since the lag between pressure and diameter changes can be small, the accuracy of the data for this simple network solution may be compromised. Better results then require diameter-corrections analogous to those described for the systemic artery pressure embodiment. Since Mode 0 vibrations are sensitive to diameter pulsations, Mode 0 energetics may need to be simulated and incorporated into a network algorithm with diameter-change correction. This simulation is approached using methods indicated above and under "Simulation Algorithms". Note that methods taught for applying a two-dimensional network algorithm to a three-dimensional flow situation are applicable e.g. in the systemic artery pressure embodiment, for correcting computations where flow does not accurately approximate a two-dimensional field.

SIMULATION ALGORITHMS

This section discusses mathematical simulations of vibrational flow in visco-elastic, incompressible tissues. At each point in the tissue, flow is a vector velocity, and each vector direction component is represented by a complex number, characterizing sinusoidal amplitude and phase. Reynolds numbers are vanishingly small, so that non-linear momentum transport terms are ignored and non-turbulent flow is assured. Motions are treated as infinitesimal, so that in certain mathematical contests a vibrating object is treated as having an unchanging shape over time, resulting in a system of linear differential equations. Flow solutions are obtained by adapting the Navier Stokes equations for viscous fluid flow, modifying them to apply to sinusoidal motions and replacing the shear viscosity coefficient with a complex viscosity coefficient incorporating shear elastic modulus. The equations, involving pressure gradients and shear stresses, are separable in homogeneous regions free from static pressure gradients into component equations involving pressure without shear effects and shear stresses without pressure effects. Although low Reynolds numbers are typically expected to lead to thick boundary layers, the rapid alternations of flow at frequencies of interest tend to accentuate inertia effects relative to shear stress effects, so that shear-stress-induced velocities tend to be confined to thin boundary layers. Thus, shear velocity fields can often be ignored at a distance from a vibrating object. The deeper-penetrating pressure fields are simpler to compute than shear fields, being subject to the methods of potential flow analysis. Excitatory vibration fields are treated computationally as if they were pure potential fields propagating through a hypothetical homogeneous medium surrounding an organ or vessel of perfect spherical or radial symmetry. Evaluation of spherical or radial harmonics in organ-centered coordinates (e.g. the mode shapes about the artery axis shown in FIG. 5) of excitatory vibration fields makes use of network algorithm techniques, which provide a link between the symmetric organ simulation and the unsymmetric measured system of linked organ and vibration driver. Iterative functional minimization procedures determine best-fit parameters of a simulated vibrating system, in order to match actual body vibration measurements with their simulated counterparts. The best-fit parameters reveal fluid pressures and the tissue properties of organs and blood vessels. Despite the approximations involved, this tractable analysis yields useful results when applied to analysis in the context of this invention.

Key Equations

A non-dimensional "viscosity radius", "R" is defined as actual radius "r" divided by a characteristic length where viscous and inertial effects are comparable at kinematic viscosity "nu" and angular frequency "f". "R" is analogous to the square root of steady-flow Reynolds Number.

$$R = r/SQRT(nu/f) \quad [36]$$

For sinusoidal solutions, complex kinematic visco-elasticity coefficient "MU" has real kinematic viscosity "mu" as its real part and shear elastic modulus "Y" entering the imaginary part as in Eq. 37. In general, both mu and Y may be frequency-dependent variables, made interdependent by the constraint that MU be an analytic function where imaginary frequency "j:f" is replaced by an arbitrary complex frequency parameter "s".

$$MU = mu + Y/j \cdot f \quad [37]$$

Complex kinematic viscosity "NU" is defined as absolute viscosity "MU" divided by density "$\rho$":

$$NU = MU/\rho \quad [38]$$

Generalizing Eq. 36 to apply where viscosity is complex-valued NU with real and imaginary parts NUx and NUy yiels Eq. 39:

$$R = r \cdot SQRT(f \cdot NUx/(NUx^2 + NUy^2)) \quad [39]$$

We further characterize the ratio of elastic to viscous components of complex NU by the ratio "q" of Eq. 40:

$$q = -NUy/NUx = Y/(f \cdot mu) \quad [40]$$

With these definitions, we can write the equations governing potential and shear flow for cylindrical and spherical geometries. We begin with the cylindrical case. If "u" is velocity in a radial direction and "v" is velocity in a tangential direction, associated with non-dimensional radius "R" and angle "$\theta$", then we have:

$$u = U \cdot \cos(n \cdot \theta) \cdot EXP(j \cdot f \cdot t) \quad [41]$$

$$v = V \cdot \sin(n \cdot \theta) \cdot EXP(j \cdot f \cdot t) \quad [42]$$

We have split u and v into radial complex amplitude functions, U and V, multiplied by circumferential sine and cosine functions for Mode n, and finally multiplied by the complex EXPonential function giving the dependence on frequency and time. Adding a real constant to the cosine and sine arguments rotates the mode shape in space. Vibrational phase shift and amplitude adjustment to satisfy boundary constraints is accomplished by multiplying U and V solutions by an appropriate complex scaling coefficient.

There are two types of U solutions, potential and shear solutions "Up" and "Us". These are solutions to the following equations:

$$\delta^2 Up/\delta R^2 = (-3/R)(\delta Up/\delta R) + ((n^2 - 1)/R^2) Up \quad [43]$$

$$\delta^2 Us/\delta R^2 = (-3/R)(\delta US/\delta R) + ((n^2-1)/R^2) - q + j)Us \qquad [44]$$

The difference between the potential and shear equations is the addition of the elasticity correction, q, and the imaginary unit, j, to the shear equation. The imaginary j-term in Eq. 44 causes the solutions to spiral in the complex plane about the R-axis. The potential flow equation contains no imaginary terms. The potential flow solution is real, exhibiting no "spiraling", i.e. no vibrational phase shifts with changing R. In fact, for any given Mode n, any potential solution can be expressed as a linear combination of exactly two potential flow functions (allowing for complex scaling coefficients), $R^{n-1}$ and $R^{-n-1}$.

Similarly, for a given Mode n and elasticity correction q, any shear solution can be expressed as a linear combination of a basis pair of shear flow functions, one converging to zero at the origin and diverging at infinity, and the other converging at infinity and diverging at the origin. For going from initial conditions at some R=R0 to solution at some nearby R=R1, the best approach is numerical integration. For larger intervals, it is useful to be able to evaluate the zero-converging and infinity-converging basis solutions separately. For relatively small R, power series solution from a recursion relation works in straightforward fashion to give the zero-converging solution, with series terms of the form $Ai \cdot R^i$ starting from an arbitrary choice of coefficient Ai at i=n−1. The recursion relation fits a second solution for series terms taking the form $(Ai+Bi \cdot LN(R)) \cdot R^i$, starting with an arbitrary Ai and Bi=0 for i=−n−1. A secondary arbitrary parameter choice arises from the recursion equations for Ai at i=−n−1. This choice amounts to choosing some component of the zero-converging solution. It is found that a correct choice of complex Ai, i=n−1, in the second series yields an infinity-converging solution, numerically useful up to R=8 to 10, beyond which numerical noise overtakes even double-precision arithmetic. The Ai choice is a function of the parameter "q". For R>8, roughly, a better numerical computation of the two basis solutions is obtained from an assymptotic series in positive powers of T, for T=1/R. This type series never converges perfectly and in fact begins to diverge with added terms after an optimum resolution, but the series gives excellent results with a few terms for large R (small T). The series is derived by reexpressing Eq. 44 in terms of the function $F=\delta LN(U)/\delta R$, and then substituting 1/T for R. The resulting differential equation is first-order and non-linear, with a quadratic term leading to strong convergence to one of two distinct solutions upon numerical integration, depending on initial conditions and whether integration is for increasing of decreasing T. The two solutions correspond to the zero-converging and infinity-converging basis solutions mentioned above. A somewhat unwieldy recursion formula yields very useful sets of power series coefficients for quick numerical evaluations. The series solution is for LN(Us), the complex natural log of the shear solution of Eq. 44, and integration of the series terms readily yields a solution for Us. For mathematicians skillful with differential equations, the approaches shown here lead readily to detailed mathematical procedures.

Because of desirable mathematical properties of the differential equations just given, the solutions are consistent with the continuity constraint, or incompressibility condition. The V-solution is obtained from any U-solution (either Up or Us) by applying the continuity constraint:

$$V = (-1/n)(U + R(\delta U/\delta R)) \qquad [45]$$

The equations governing vibrational flow for spherical symmetry with the vibration axis corresponding to the spherical axis are similar, but somewhat more involved. In place of the trigonometric functions "cos (n·θ)" and "sin (n·θ)" of Eqs. 41 and 42, we substitute functions designated, respectively, "C(θ)" and "S(θ)". The functions C and S are different for each Mode number n. These functions are solutions to Eqs. 46 and 47:

$$\delta^2 C/\delta\theta^2 + \cot(\theta) \cdot \delta C/\delta\theta + N \cdot C = 0 \qquad [46]$$

$$\delta S/\delta\theta + S \cdot \cot(\theta) = C(\theta) \qquad [47]$$

The number "N" must be chosen to give a functional periodicity of 2·pi, in order that C and S be single-valued for a given angular position. The eigenvalues of N that satisfy this closure condition correspond to Mode numbers n. Solutions for N, C and S as functions of n are given in Table 2 for n from 0 to 3.

TABLE 2

| | | Spherical Vibration Functions of Angle | |
|---|---|---|---|
| n | N | C | S |
| 0 | 0 | 1 | 0 |
| 1 | 2 | $\cos(\theta)$ | $\sin(\theta)$ |
| 2 | 6 | $\frac{1}{4} + (\frac{3}{4})\cos(2\theta)$ | $(\frac{1}{4})\sin(2\theta)$ |
| 3 | 12 | $(\frac{3}{8})\cos(\theta) + (\frac{5}{8})\cos(3\theta)$ | $(1/32)\sin(\theta) + (5/32)\sin(3\theta)$ |

The mode shapes are slightly distorted from the single-component sinusoids of the cylindrical solutions, although the mode shape graphs appear very similar to the drawings of FIG. 5. Given these angle functions, we now move on to the spherical radical functions U and V, keeping the same notation as for the analogous cylindrical equations above:

$$\delta^2 Up/\delta R^2 = (-4/R)(\delta Up/\delta R) + ((N-2)/R^2)Up \qquad [48]$$

$$\delta^2 Us/\delta R^2 = (-4/R)(\delta Us/\delta R) + (((N-2)/R^2) - q + j)Us \qquad [49]$$

As before, the shear equations differ from the potential equations only in the addition of the q-term and the imaginary unit, j. The functional behavior is quite similar to the cylindrical cases. For a given n and corresponding eigenvalue N, the two potential solutions are power-law functions of R, as is easily shown by substitution. The two shear solutions converge at zero and infinity, and they spiral about the R-axis in the complex plane.

As before, V comes from any U solution using the continuity equation. The solution shown is independent of Mode number n or the eigenvalue N, since these parameters are incorporated into the definition of the functions C and S. Hence, we have simply:

$$V = -R(\delta U/\delta R) - 2U \qquad [50]$$

For both cylindrical and spherical solutions, separability of the potential and shear equations holds only in homogeneous annular regions. At boundaries where simulated tissue properties change or where a static pressure differential is encountered, the combinations of two potential and two shear flow solutions allowed on either side of the boundary must obey four cross-boundary continuity constraints: (1) matched normal velocity; (2) matched tangential velocity; (3) matched normal stress; (4) matched tangential stress. Note that the stress acting normal across a circumferential boundary (i.e. radially) includes components of shear stress and pressure. Detailing of these constraints requires application of stress tensor analysis as described e.g. in Symon, *Mechanics,* Op. Cit. (for Eq. 1), Ch. 10.

Where a gradient in static pressure, e.g. blood pressure, extends over a significant thickness and it is desirable to handle the gradient with continuous differential equations rather than with multiple discontinuous pressure jumps between concentric layers, then potential and shear equations couple together and are solved as a simultaneous system. This coupled system is shown here for cylinders and radially-symmetric distributions of tissue and pressure. A comparable set applies in the spherical case.

$$\frac{\delta^2 U}{\delta r^2} + \frac{3}{r} \frac{\delta U}{\delta r} - \left( \frac{n^2 - 1}{r^2} + \frac{j\omega\rho}{M} \right) U - \frac{\Theta}{M} =$$

0: shear force & pressure gradient $$\frac{\delta\Theta}{\delta r} + \frac{\Theta}{r} - \frac{n^2}{r^2} \phi = 0 : \text{coupled LaPlace equation}$$

$$\frac{\delta\phi}{\delta r} =$$

$$\Theta + \frac{U}{j\omega} \left( \frac{n^2 - 1}{r} \right) \frac{\delta P}{\delta r} : \text{vib. pressure mod. by P-gradient}$$

In this system of equations, r is dimensional radius, U is complex velocity amplitude (as in Us and Up above), P is non-vibrational or static pressure, M is complex absolute viscosity, $\rho$ is density, $\Theta$ is vibration pressure and $\phi$ is vibration pressure as modified by a static pressure gradient

I claim:

1. A method for inducing vibrations in a selected element of the human body and detecting the nature of response for determining internal pressure of said selected element non-invasively, said method comprising steps of:
   inducing vibrations in a selected element of the body by use of a driver means, including vibrations at multiple frequencies below 20 KHz by operation of said driver means,
   determining a velocity parameter and a force parameter, said parameters being related in a manner whereby mechanical power flowing between a predetermined region of said driver means and said body, including power arising from operation of said driver means below 20 KHz, is a function of said velocity and force parameters,
   sensing time-variation of at least one dimension of said selected element, including in response to operation of said driver means below 20 KHz,
   determining, from said time-variation, at least one component of vibration mode shape,
   determining time-samples of said velocity parameter, said force parameter and said component of mode shape,
   processing said time-samples by time-windowing and correlation with sinusoids at multiple frequencies, to obtain time-frequency parameters of window-center-time and frequency for each said velocity parameter, force parameter and component of vibration mode shape, and including amplitude and phase information,
   determining changes in said time-frequency parameters from one said window-center-time to another caused at least in part by change in internal pressure of said selected element from one window-center-time to another,
   calculating, from said time-frequency parameters and changes, mechanical vibrational impedances of said selected element in its surroundings at more than one frequency, and
   computing, from said impedances, said internal pressure.

2. The method of claim 1 including the step of using said calculated impedances to determine mechanical characteristics of said body in addition to pressure.

3. The method of claim 1 including the steps of:
   using said changes in time-frequency parameters for determining a coefficient indicating the nature of vibrational coupling between said predetermined region of said driver means and said selected element, and
   using said coefficient for computing said mechanical vibrational impedances.

4. The method of claim 3 including the steps of:
   direct coupled measuring of at least one dimension of said selected element over time, including static and low frequency measuring at a rate below frequencies of operation of said driver means,
   evaluating the effect of said measured dimension and of said variation below said frequencies of operation upon said coefficient, for indication of the nature of vibrational coupling, and
   employing the result of evaluating the effect of said measured dimension and of said variation in computation of mechanical vibrational impedances.

5. The method of claim 4 wherein said steps of determining the effect of said measured dimension and of said variation and computing mechanical vibrational impedances is by simultaneous equations.

6. A non-invasive system for inducing vibration in a selected element of the body and detecting the nature of the response for determining internal pressure of said selected element,
   said system comprising:
   a driver means adapted for inducing vibrations, including vibrations below 20 KHz, in said selected element of the body,
   means for determining a velocity parameter and a force parameter related in a manner whereby mechanical power flowing between a predetermined region of said driver means and said body, including power arising from operation of said driver means below 20 KHz, is a function of said velocity and force parameters,
   means for sensing time-variation of at least one dimension of said selected element, including in response to operation of said driver means below 20 KHz, means for determining from said time-variation, at least one component of vibration mode shape, means for determining time-samples of said velocity parameter, said force parameter and said component of mode shape, means for processing said time-samples by time-windowing and correlation with sinusoids at multiple frequencies, to obtain time-frequency parameters of window-center-time and frequency for each said velocity parameter, force parameter and component of vibration mode shape, and including amplitude and phase information, means for determining changes in said time-frequency parameters from one said window-center-time to another caused at least in part by change in internal pressure of said selected element from one window-center-time to another, means for calculating, from said time-frequency parameters and changes, mechanical vibrational impedances of said selected element in its surroundings at more than one frequency, and computer means for computing, from said impedances, said internal pressure.

7. The system of claim 6 further comprising means for using said changes in time-frequency parameters for determining a coefficient indicating the nature of vibrational coupling between said predetermined region of said driver means and said selected element, and means for using said coefficient for computing said mechanical vibrational impedances.

8. The system of claim 7 further comprising means for direct coupled measuring of at least one dimension of said selected element over time, including static and low frequency measuring at a rate below frequencies of operation of said driver means, means for evaluating the effect of said measured dimension and of said variation below said frequencies of operation upon said coefficient for indication of the nature of vibrational coupling, and means for employing the result of evaluating the effect of said measured dimension and of said variation in computation of mechanical vibrational impedances.

* * * * *